US012472176B2

(12) United States Patent
Agrawal et al.

(10) Patent No.: US 12,472,176 B2
(45) Date of Patent: Nov. 18, 2025

(54) PHARMACEUTICAL COMPOSITIONS COMPRISING (S)-4-(4-(4-(((2-(2,6-DIOXOPIPERIDIN-3-YL)-1-OXOISOINDOLIN-4-YL)OXY)METHYL)BENZYL)PIPERAZIN-1-YL)-3-FLUOROBENZONITRILE AND METHODS OF USING THE SAME

(71) Applicant: Celgene Corporation, Summit, NJ (US)

(72) Inventors: Anjali Agrawal, Basking Ridge, NJ (US); Biplob K. Mitra, Basking Ridge, NJ (US); Prajwal Gunwanth Thool, Short Hills, NJ (US); Shannon Higgins-Gruber, Scotch Plains, NJ (US); Jennifer Almodovar Rodriguez, Cranford, NJ (US); Demin Liu, Berkeley Heights, NJ (US)

(73) Assignee: Celgene Corporation, Summit, NJ (US)

( * ) Notice: Subject to any disclaimer, the term of this patent is extended or adjusted under 35 U.S.C. 154(b) by 494 days.

(21) Appl. No.: 18/014,882

(22) PCT Filed: Jul. 6, 2021

(86) PCT No.: PCT/US2021/040452

§ 371 (c)(1),
(2) Date: Jan. 6, 2023

(87) PCT Pub. No.: WO2022/010854

PCT Pub. Date: Jan. 13, 2022

(65) Prior Publication Data

US 2023/0270742 A1 Aug. 31, 2023

Related U.S. Application Data

(60) Provisional application No. 63/048,998, filed on Jul. 7, 2020.

(51) Int. Cl.
*A61K 31/496* (2006.01)
*A61K 9/48* (2006.01)

(52) U.S. Cl.
CPC ............ *A61K 31/496* (2013.01); *A61K 9/485* (2013.01); *A61K 9/4858* (2013.01); *A61K 9/4866* (2013.01)

(58) Field of Classification Search
CPC ...... A61K 31/496; A61K 47/02; A61K 47/26; A61K 47/36; A61K 9/0053; A61K 9/4858; A61K 9/4866; A61K 47/12; A61K 47/24; A61P 35/00; C07D 401/04
See application file for complete search history.

(56) References Cited

U.S. PATENT DOCUMENTS

2004/0229930 A1 11/2004 Gatti
2012/0172427 A1 7/2012 Hauck
2013/0058876 A1 3/2013 Gururajan et al.
2017/0197933 A1 7/2017 Alexander et al.
2019/0008852 A1 1/2019 Alexander et al.
2019/0361005 A1 11/2019 Hansen et al.
2020/0215061 A1 7/2020 Agrawal et al.

FOREIGN PATENT DOCUMENTS

AU 2016213879 B2 9/2016
WO WO 2019/014100 A1 1/2019
WO WO 2019/223770 A1 11/2019
WO WO 2019/226761 A1 11/2019
WO WO 2020/146441 A1 7/2020

OTHER PUBLICATIONS

Hansen et al., "Discovery of CRBN E3 ligase modulator CC-92480 for the treatment of relapsed and refractory multiple myeloma," J. Med. Chem., 63(13):6648-6676 (2020), retrieved from the Internet: https://dk.doi.org/10.1021/acs.jmedchem.9b01928.
International Search Report and Written Opinion for International Application No. PCT/US2021/040452, mailed Nov. 29, 2021.
Liu et al., "Medicinal Polymer Materials," New Century 2nd Edition, China Traditional Medicine Press, pp. 92-93 (2017).

*Primary Examiner* — Clinton A Brooks
*Assistant Examiner* — Kyle Nottingham
(74) *Attorney, Agent, or Firm* — Jones Day

(57) ABSTRACT

Provided herein are pharmaceutical compositions (e.g., oral dosage formulations) comprising (S)-4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, mixture of enantiomers, tautomer, isotopolog, or pharmaceutically acceptable salt thereof, and a carrier or diluent. Also provided herein are methods of preparing and methods of using the pharmaceutical compositions.

22 Claims, 22 Drawing Sheets

XRPD of Form K of a Free Base of Compound 1

XRPD of Form K' of a Free Base of Compound 1

PHARMACEUTICAL COMPOSITIONS COMPRISING (S)-4-(4-(4-(((2-(2,6-DIOXOPIPERIDIN-3-YL)-1-OXOISOINDOLIN-4-YL)OXY)METHYL)BENZYL) PIPERAZIN-1-YL)-3-FLUOROBENZONITRILE AND METHODS OF USING THE SAME

This application is a U.S. National Stage Application of International Patent Application No. PCT/US2021/040452, filed Jul. 6, 2021, which claims priority to U.S. Provisional Application No. 63/048,998, filed on Jul. 7, 2020, the entirety of each of which is incorporated herein by reference.

2. FIELD

Provided herein are pharmaceutical compositions comprising (S)-4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, mixture of enantiomers, tautomer, isotopolog, or pharmaceutically acceptable salt thereof, and a carrier or diluent. Methods of use of such pharmaceutical compositions for treating, preventing, and managing various disorders are also provided herein.

3. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. (Rawstron et al., *Blood* 2015; 125(12):1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

The variety of possible pharmaceutical compositions (e.g., oral dosage formulations comprising different excipients) creates potential diversity in physical and chemical properties for a given pharmaceutical compound. The discovery and selection of pharmaceutical compositions are of great importance in the development of an effective, stable and marketable pharmaceutical product.

4. SUMMARY

Certain pharmaceutical compositions comprising Compound 1 are previously described in U.S. application Ser. No. 16/737,721, the entirety of which is incorporated herein by reference.

Provided herein are pharmaceutical compositions (e.g., oral dosage formulations) comprising 1) a hydrobromide salt of Compound 1:

1

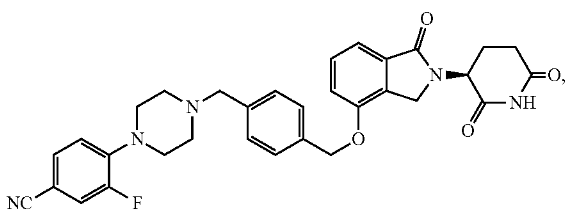

2) a mixture of mannitol and cellulose or a mixture of mannitol and starch, 3) hydroxypropyl methylcellulose (HPMC), 4) sodium starch glycolate (SSG), and 5) stearic acid.

Also provided herein are pharmaceutical compositions (e.g., oral dosage formulations) comprising 1) Compound 1:

1

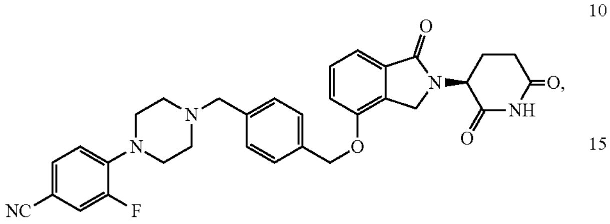

2) a mixture of mannitol and starch, 3) sodium stearyl fumarate, and 4) optionally fumaric acid.

Compound 1 has the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Also provided herein are methods of preparing the pharmaceutical compositions.

The pharmaceutical compositions provided herein are useful formulations for use in animals or humans. Thus, embodiments herein encompass the use of these pharmaceutical compositions as a final drug product. Certain embodiments provide pharmaceutical compositions useful in making final dosage forms with improved properties, e.g., powder flow properties, compaction properties, tableting properties, stability properties, and excipient compatibility properties, among others, that are needed for manufacturing, processing, formulation and/or storage of final drug products.

Also provided are pharmaceutical compositions formulated for administration by an appropriate route and means containing effective concentrations of Compound 1 provided herein. In one embodiment, the pharmaceutical compositions are oral dosage formulations. In one embodiment, the pharmaceutical compositions are immediate-release (IR) oral dosage formulations.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

In one embodiment, provided herein are methods of treating multiple myeloma comprising administering the pharmaceutical compositions provided herein. Also provided herein are combination therapies using the pharmaceutical compositions provided herein, in combination with a therapy, e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. BRIEF DESCRIPTION OF THE DRAWINGS

Figure 3A:
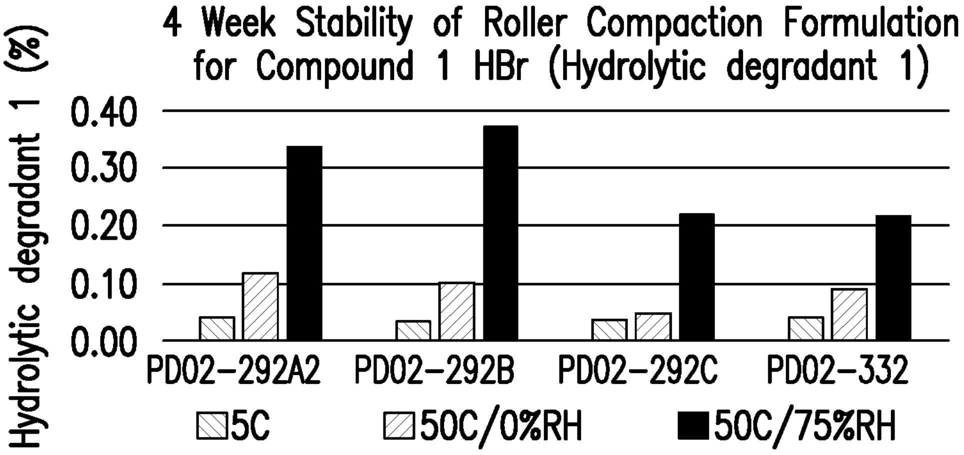
Figure 3B:
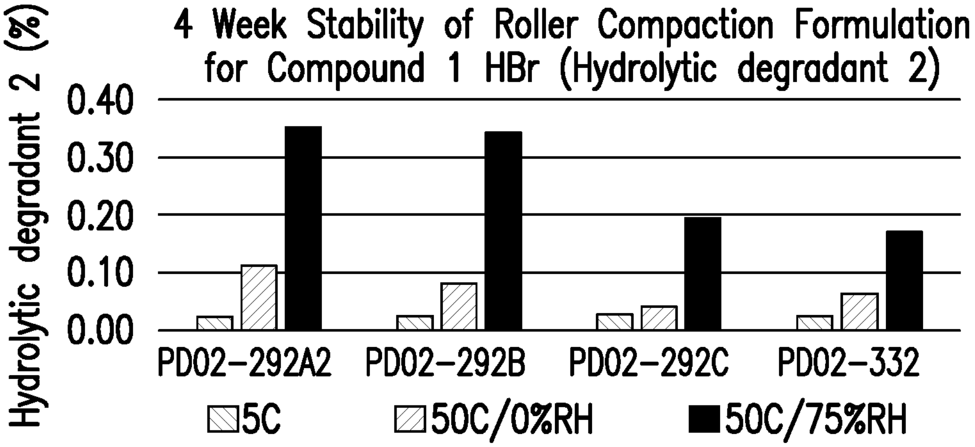
Figure 3C:
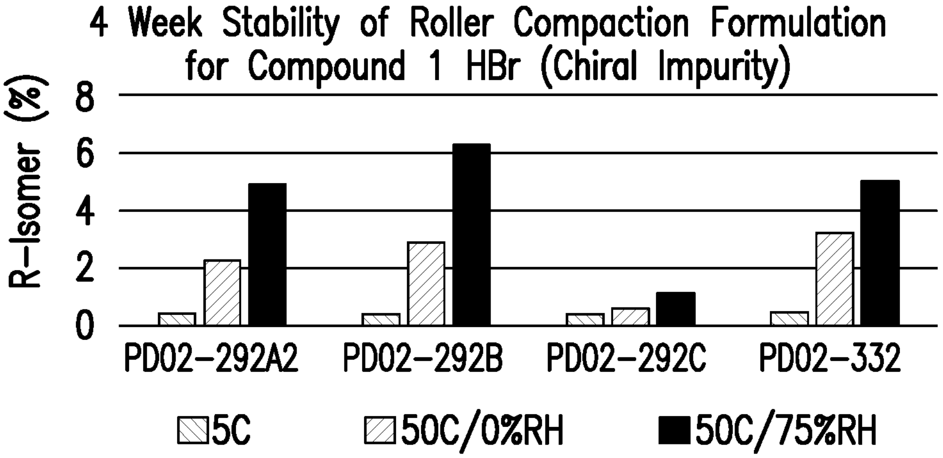

FIG. 3A, FIG. 3B, and FIG. 3C show the hydrolytic degradant No. 1, hydrolytic degradant No. 2, and chiral impurity levels for prototype formulations prepared by RC process, respectively.

Figure 4A:
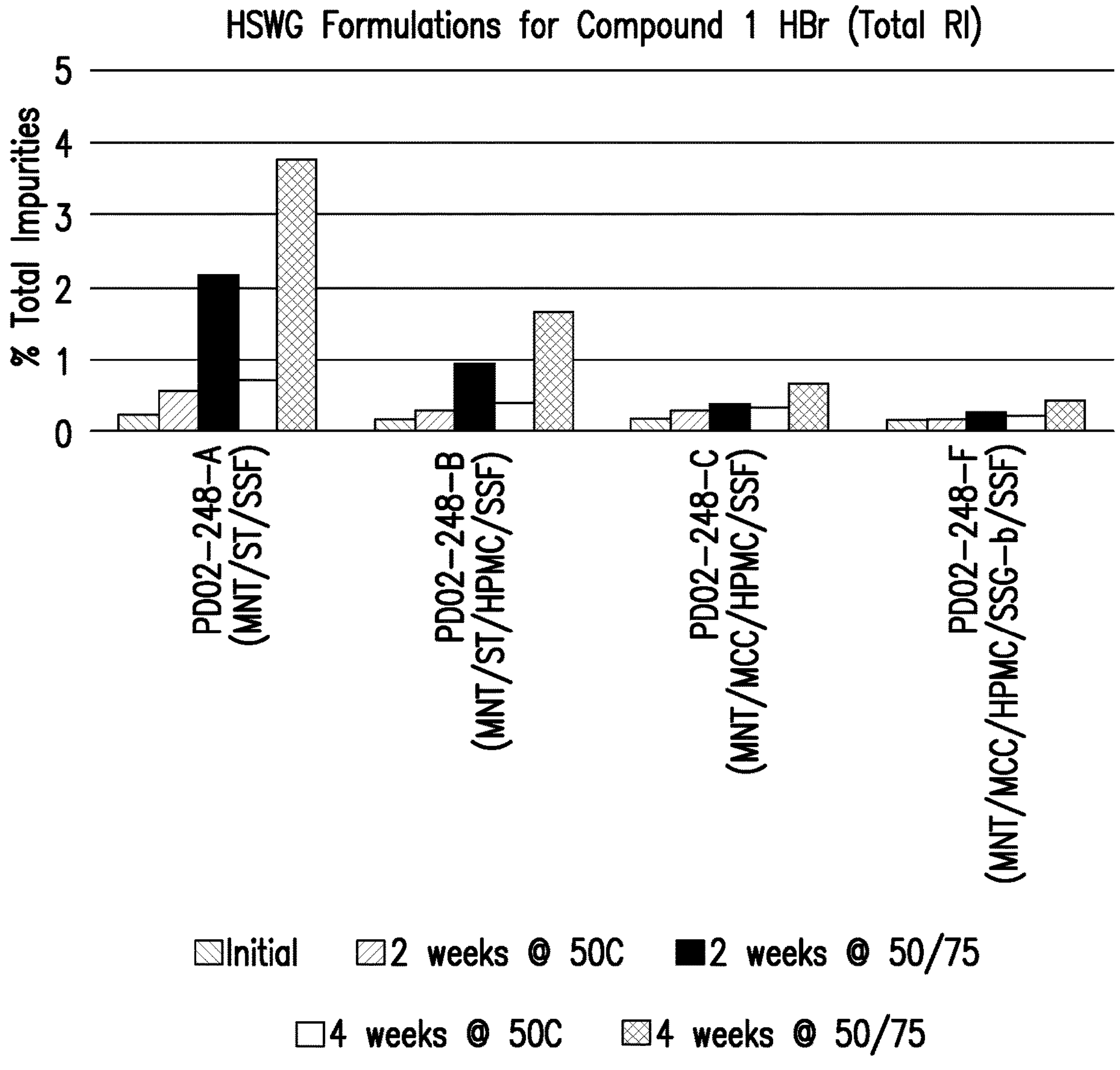
Figure 4B:
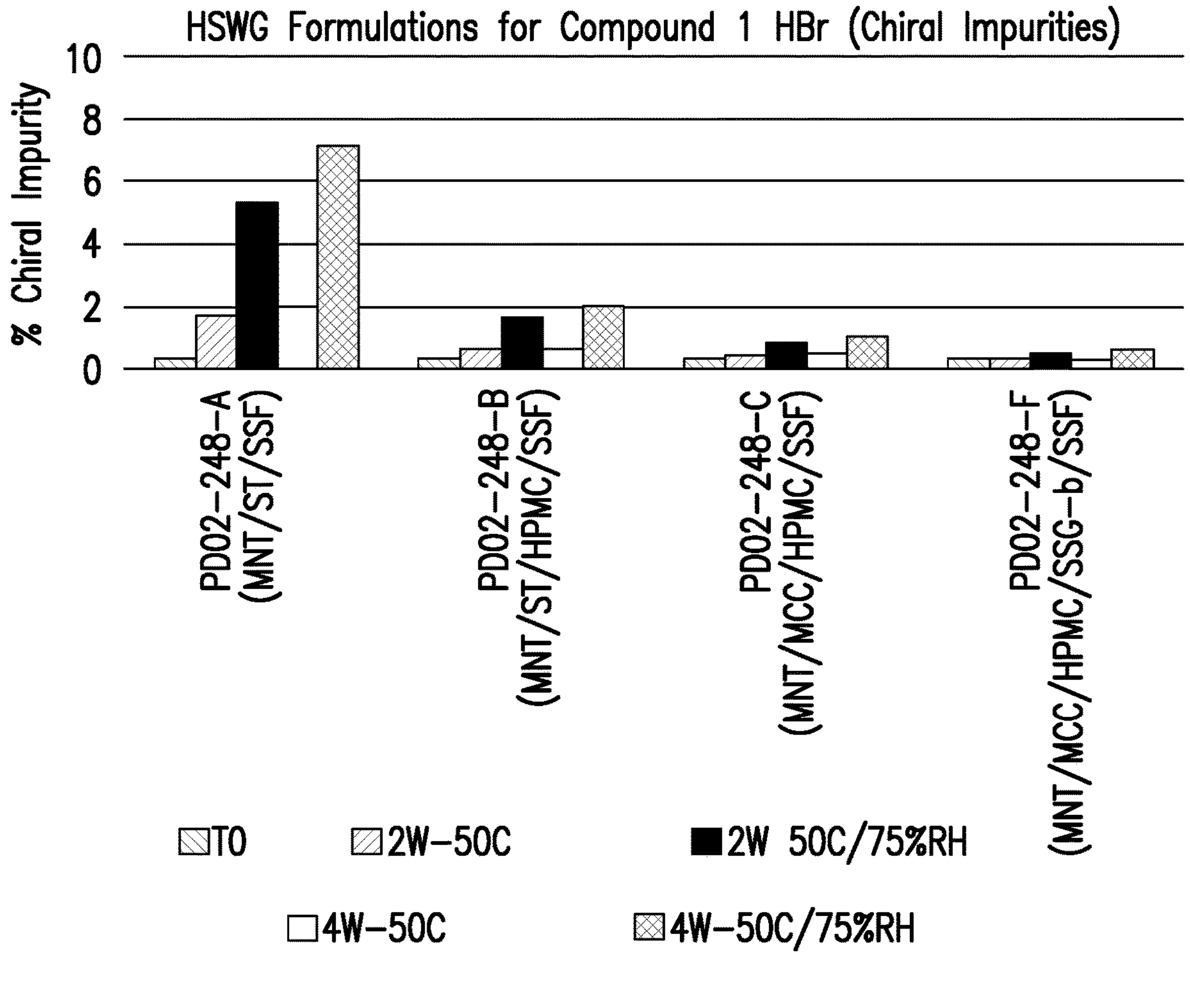

FIG. 4A and FIG. 4B show the total chemical impurities and chiral impurity levels for prototype formulations prepared by HSWG process, respectively.

Figure 5A:
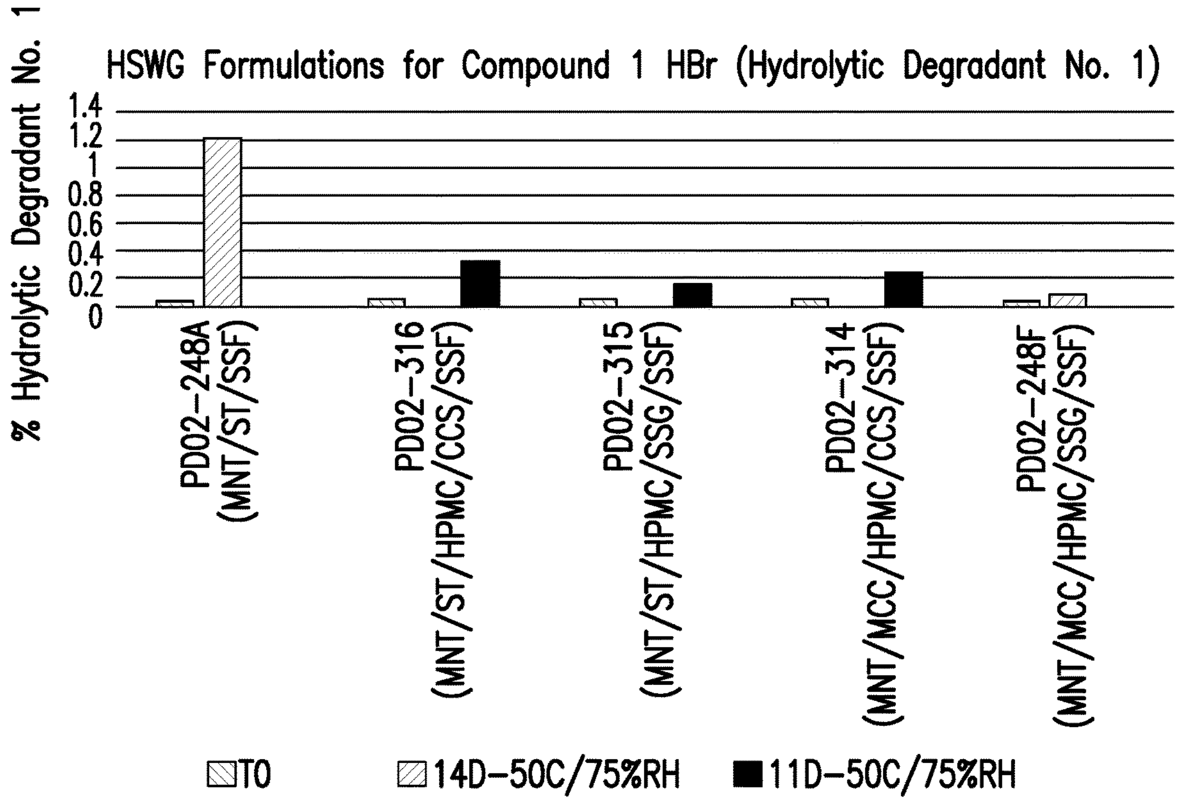
Figure 5B:
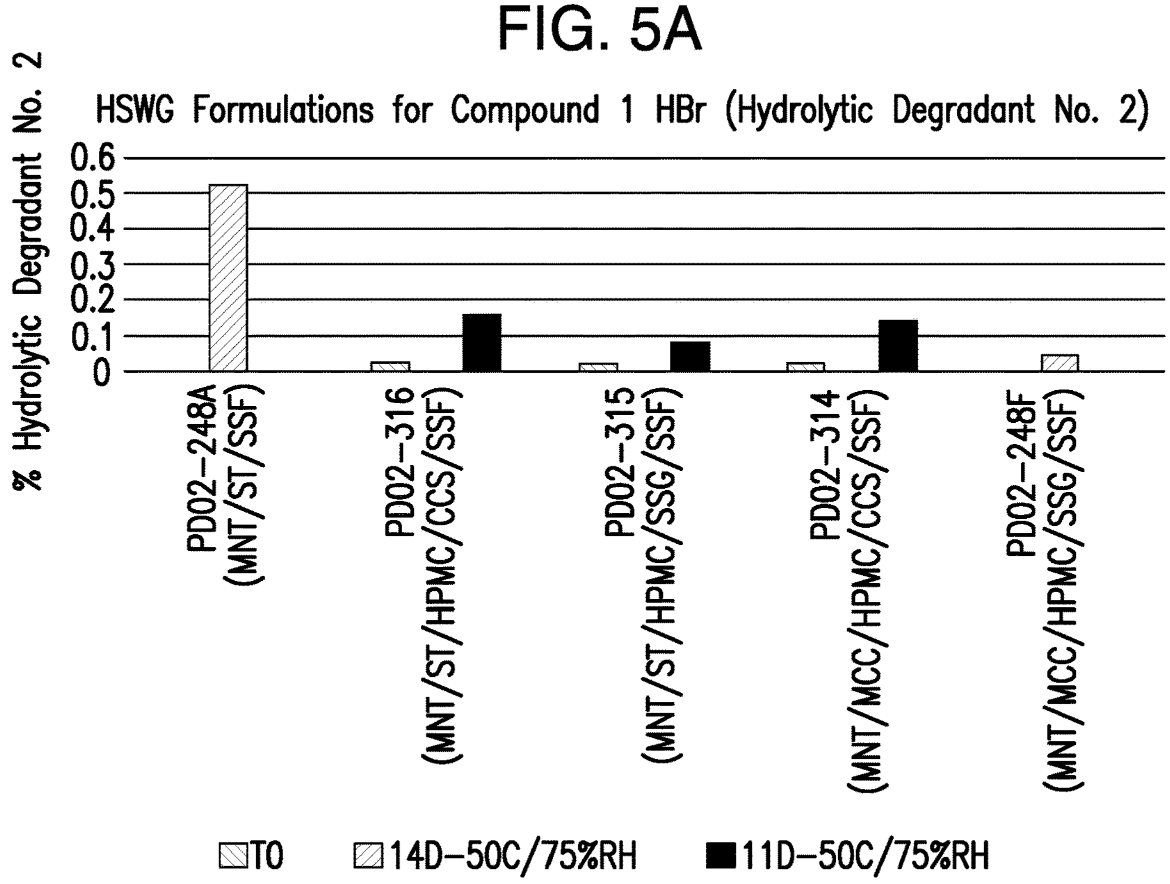
Figure 5C:
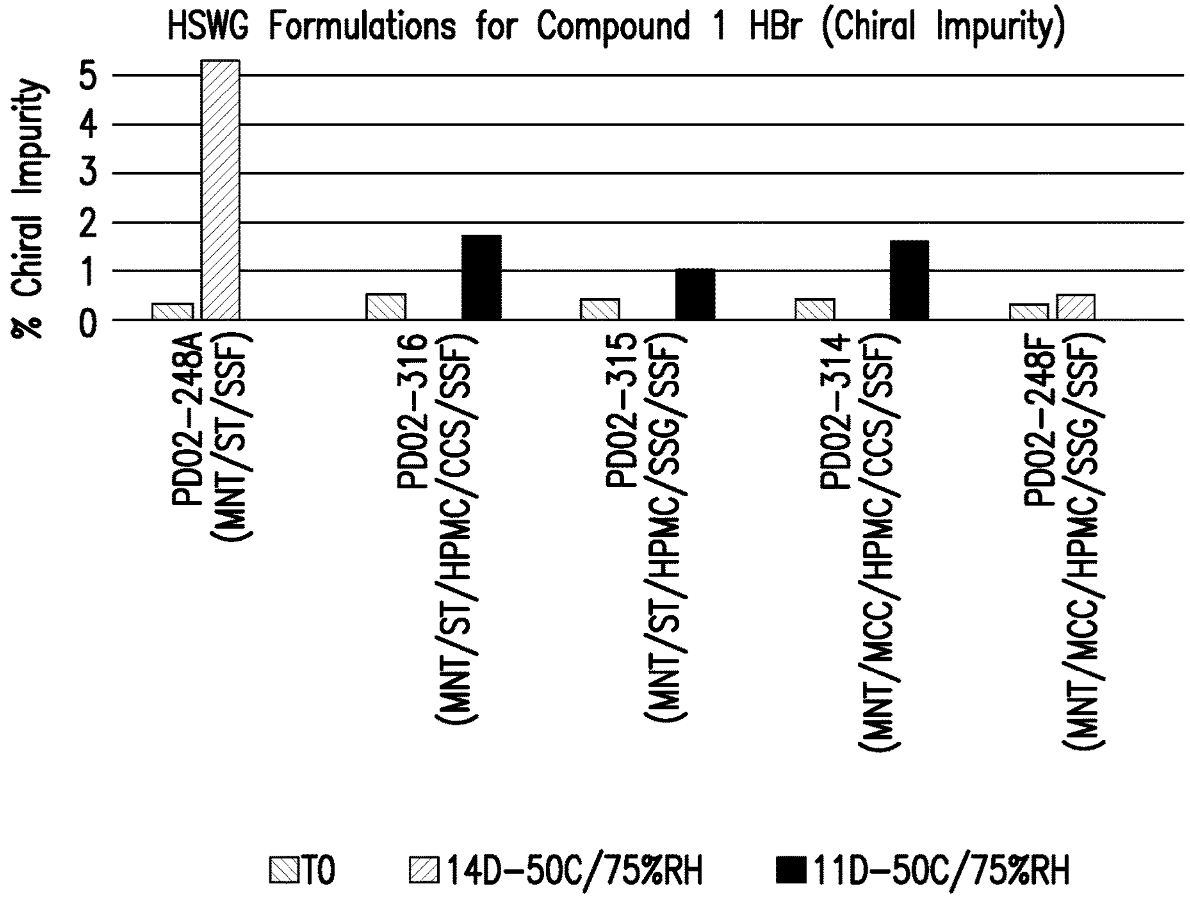

FIG. 5A, FIG. 5B, and FIG. 5C show the hydrolytic degradant No. 1, hydrolytic degradant No. 2, and chiral impurity levels for prototype formulations prepared by HSWG process, respectively.

Figure 6A:
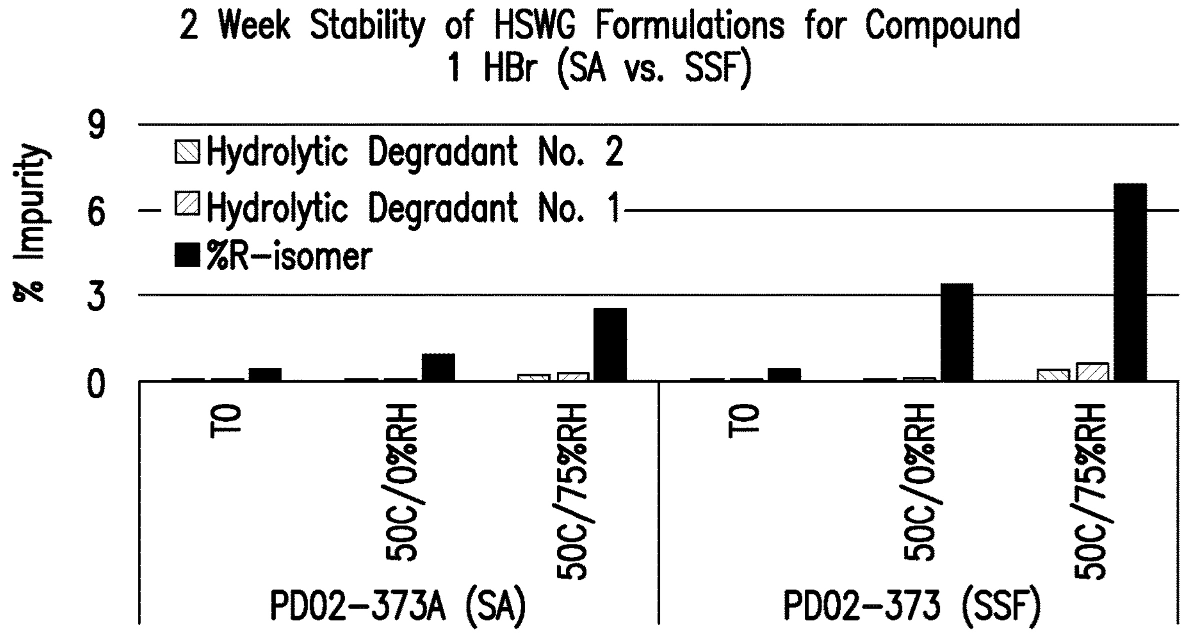
Figure 6B:
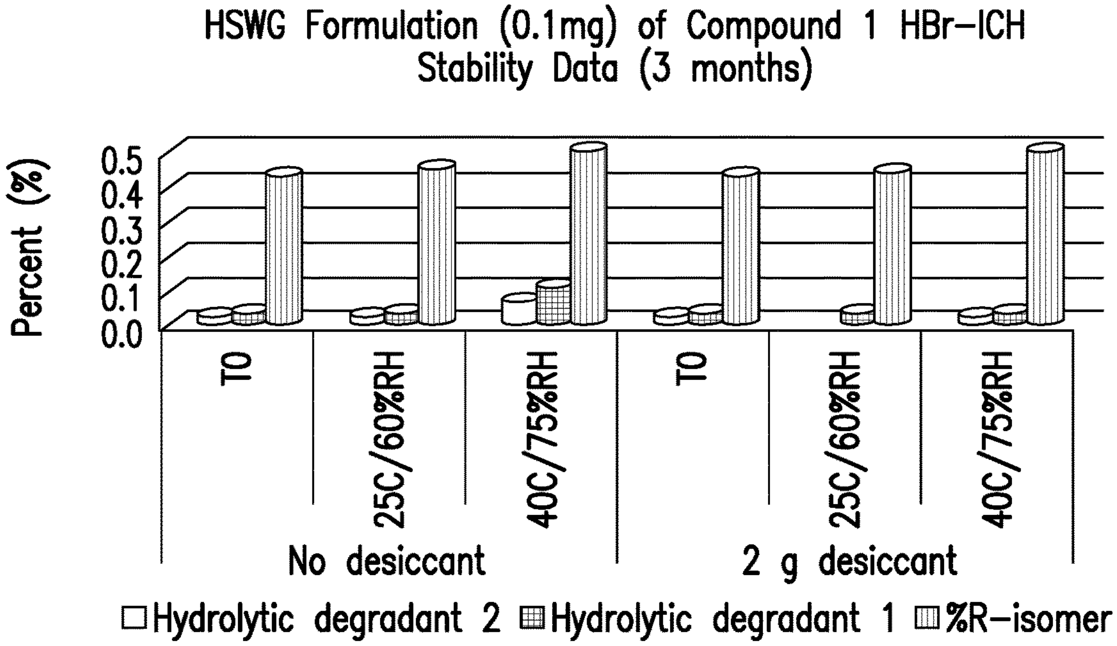

FIG. 6A and FIG. 6B show impact of stearic acid on chemical and chiral purities based on open dish and at storage conditions, respectively.

Figure 7:
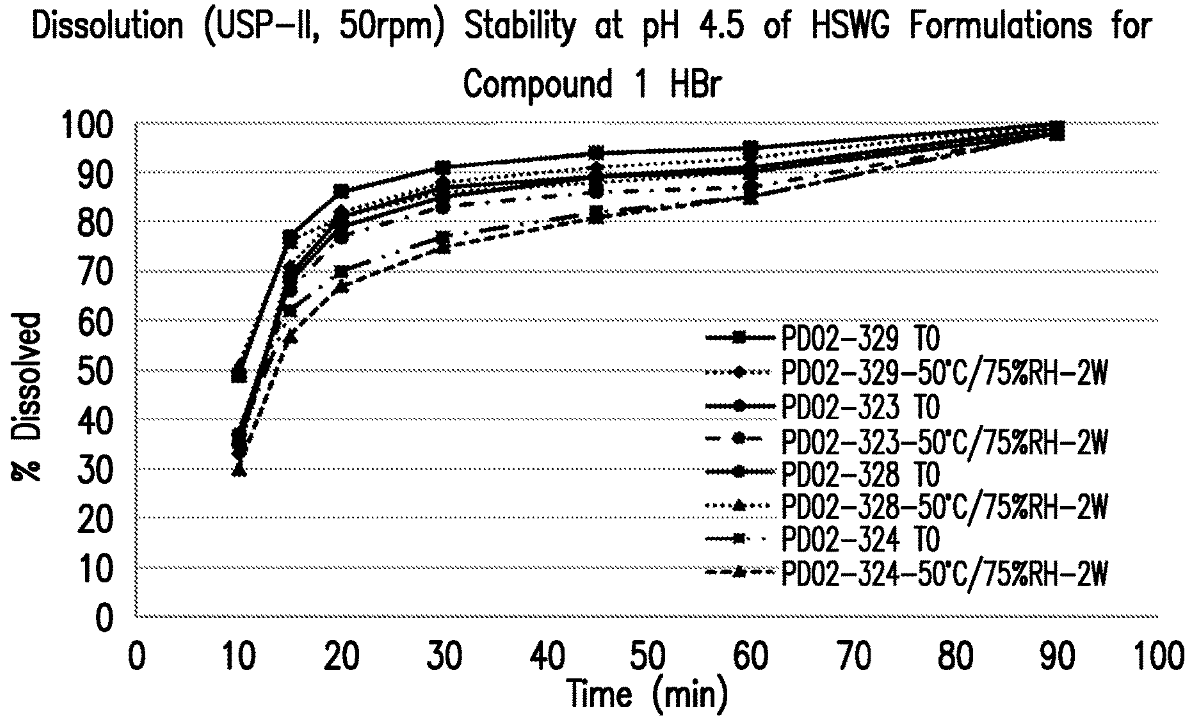

FIG. 7 shows dissolution profiles of prototype formulations prepared by HSWG process.

Figure 8:
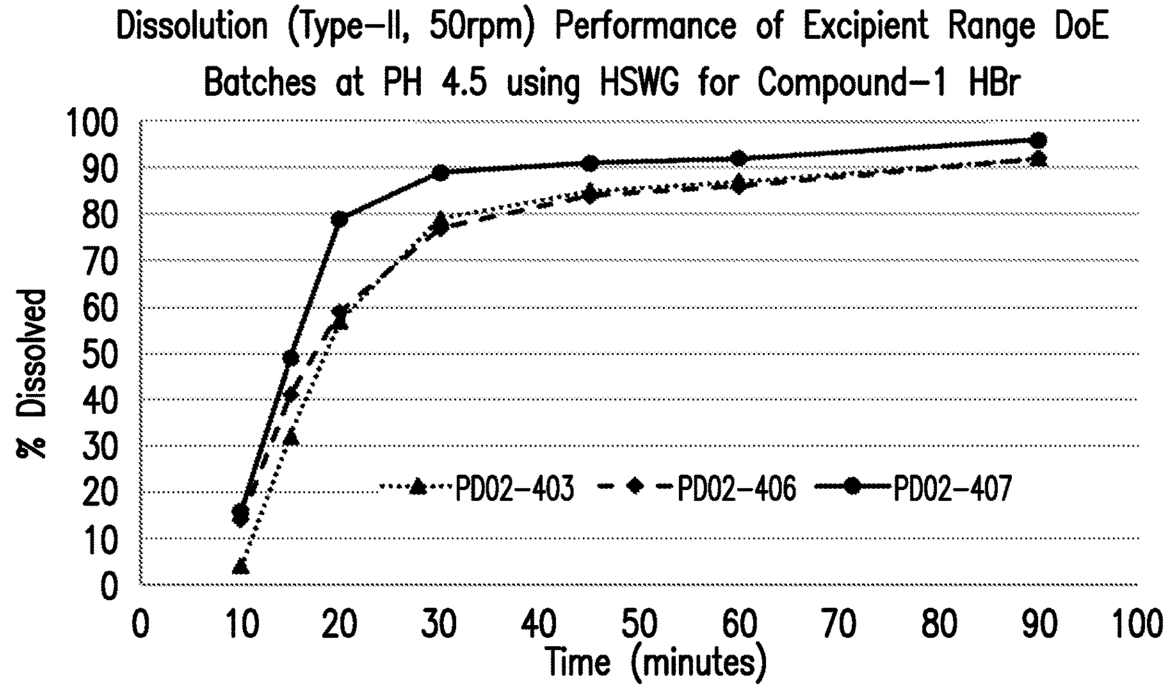

FIG. 8 shows dissolution release profiles of excipient range DoE batches at T=0 at pH 4.5.

Figure 9:
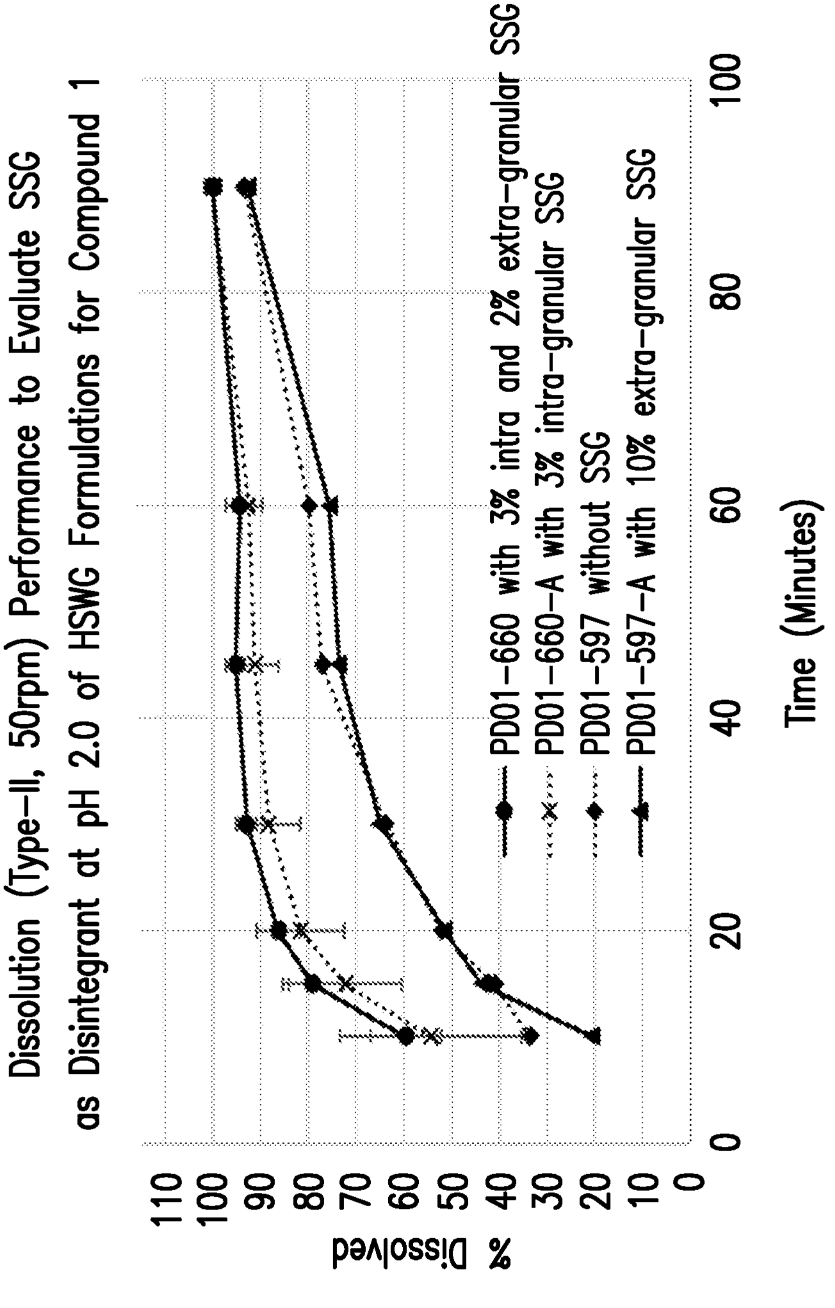

FIG. 9 shows Impact of SSG on Dissolution Performance using Prototype Formulations.

Figure 10A:
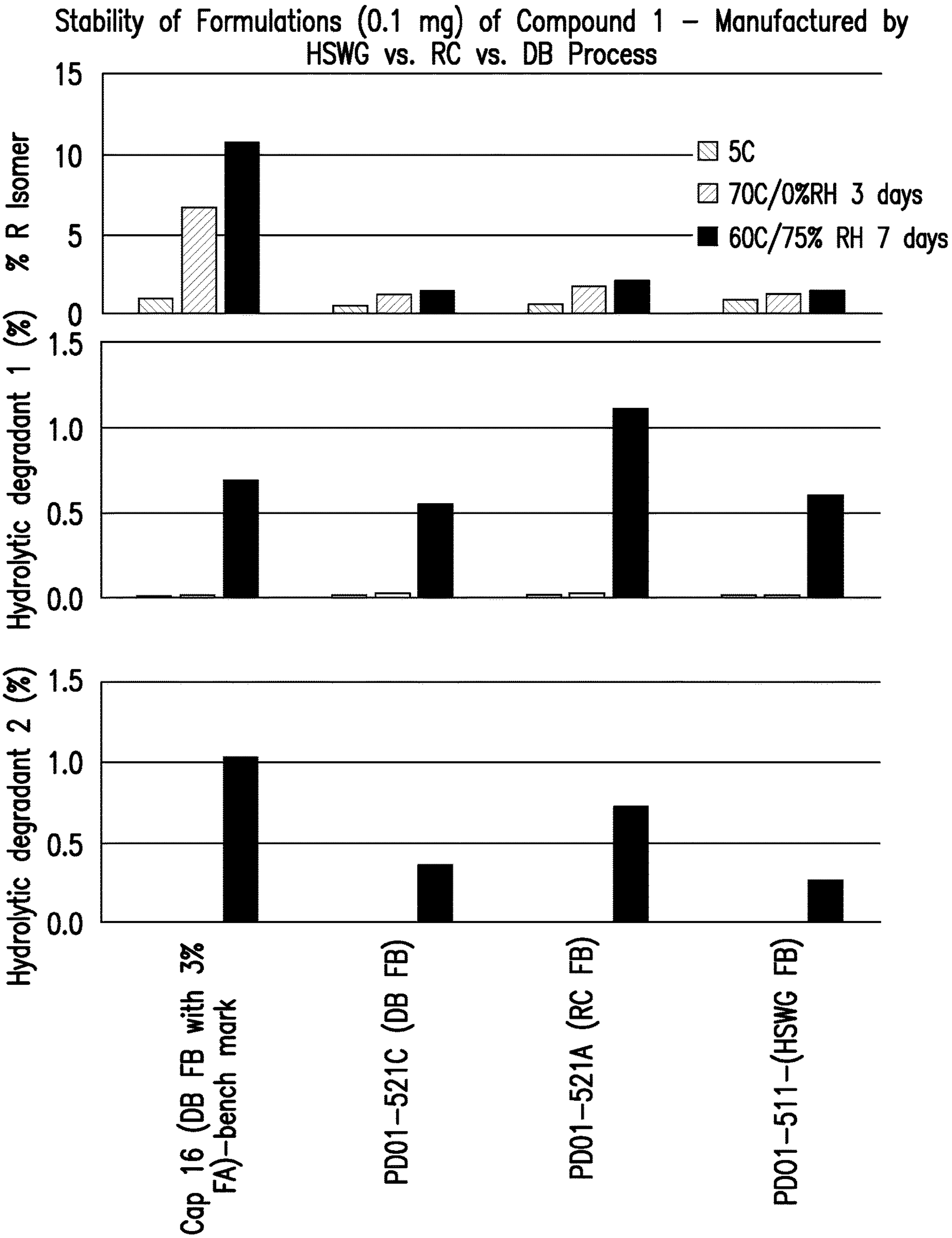
Figure 10B:
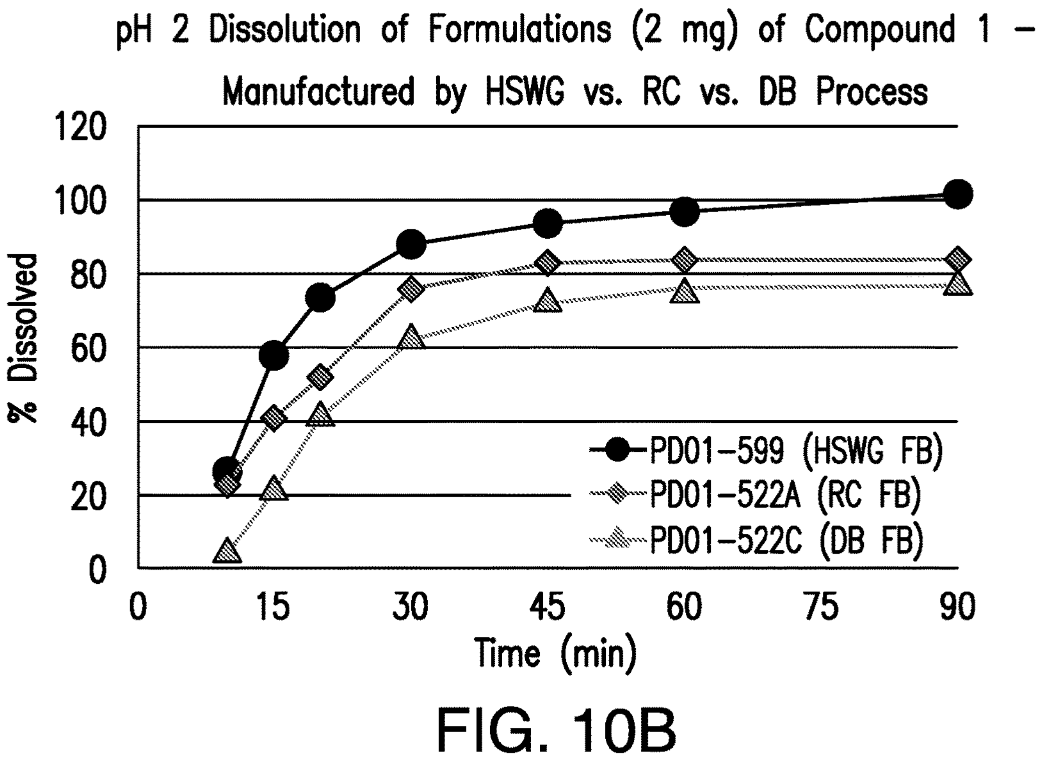

FIG. 10A shows comparative stability (chiral/chemical) profiles of the DP manufactured using various manufacturing processes (DB vs RC vs HSWG); FIG. 10B shows comparative dissolution profiles.

Figure 11:
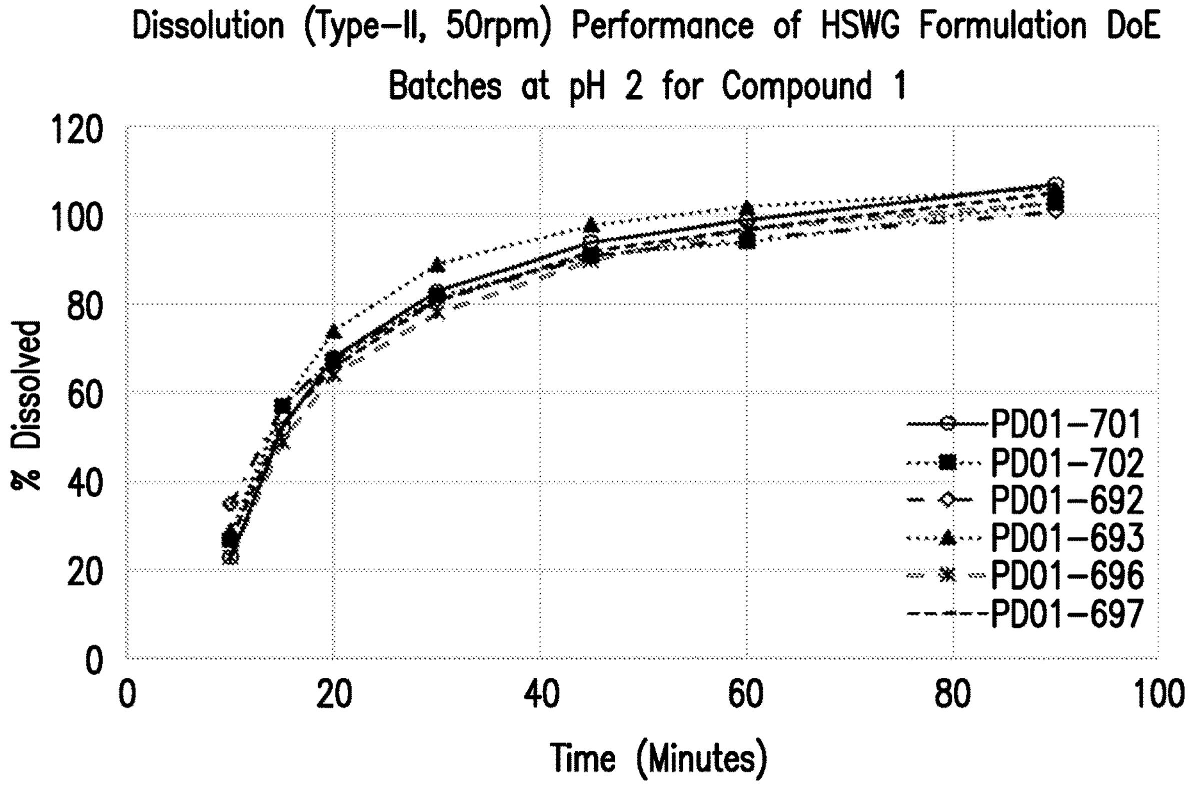

FIG. 11 shows dissolution release profiles of excipient range DoE batches (T=0) at pH 2.0.

Figure 12A:
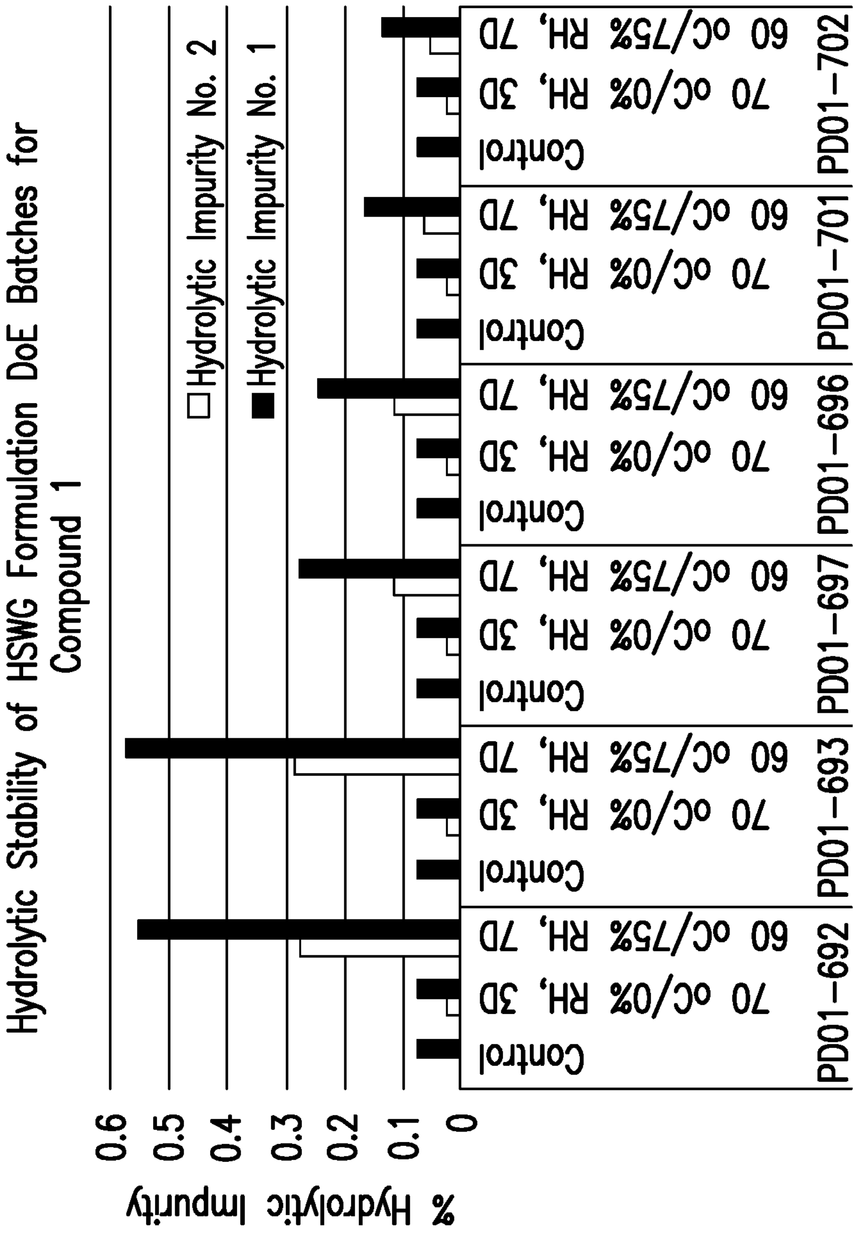
Figure 12B:
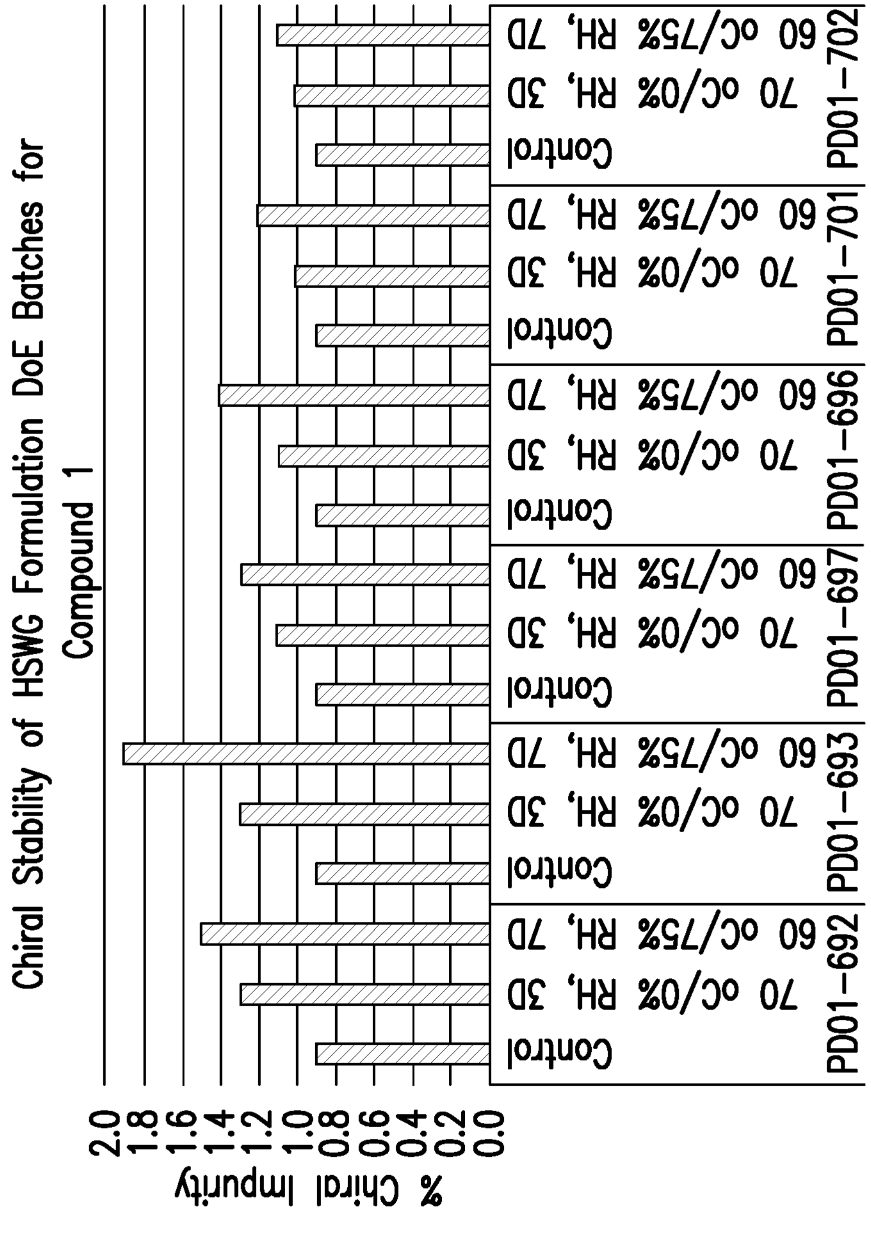

FIG. 12A and FIG. 12B show the related hydrolytic impurity and chiral impurity levels for excipient range DoE batch, respectively.

Figure 13:
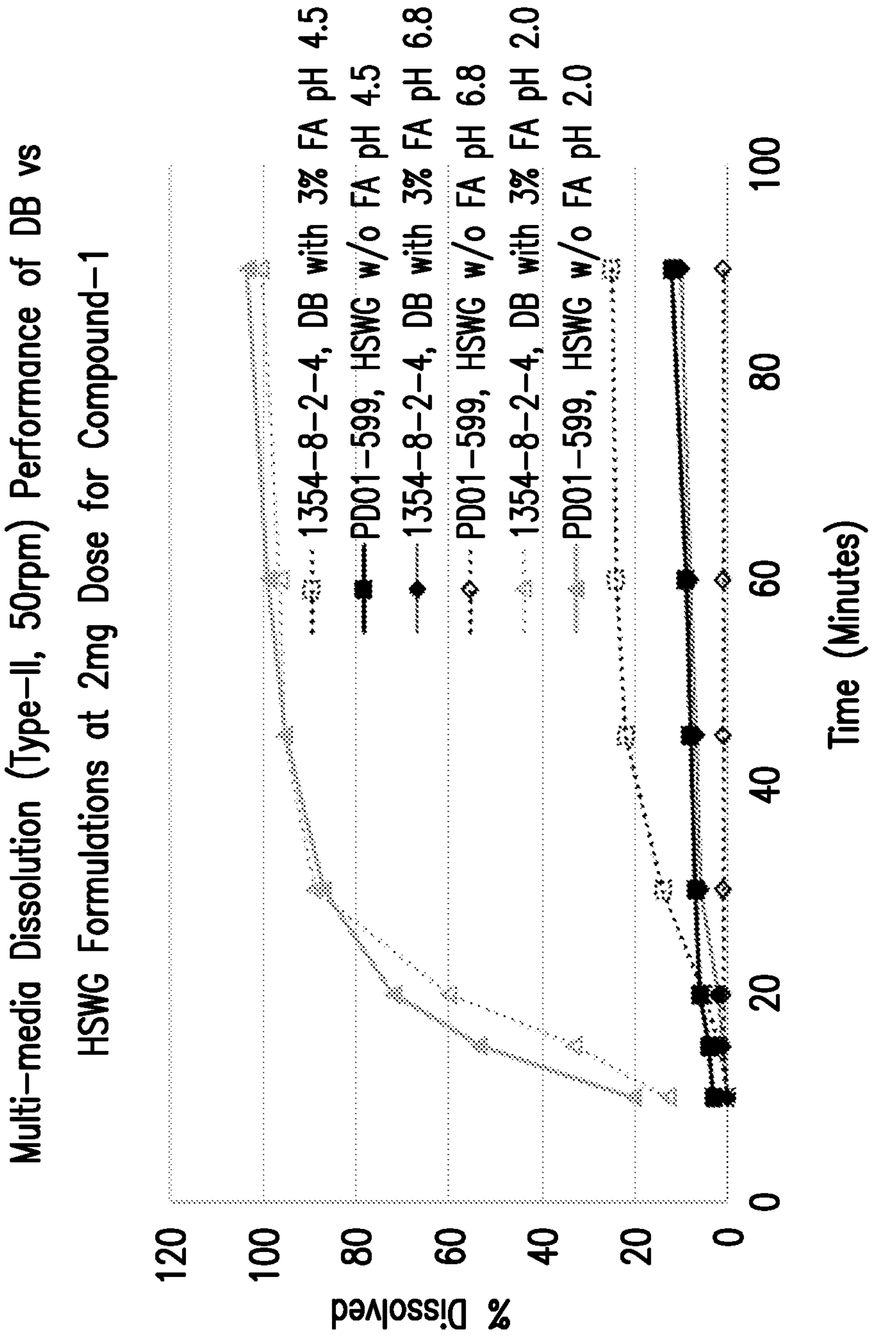

FIG. 13 shows comparative DB free base formulation with 3% FA and HSWG free base formulation multi-media dissolution profiles at pH 1.2, 2.0, 4.5 and 6.8 using 2 mg dose strength.

Figure 14:
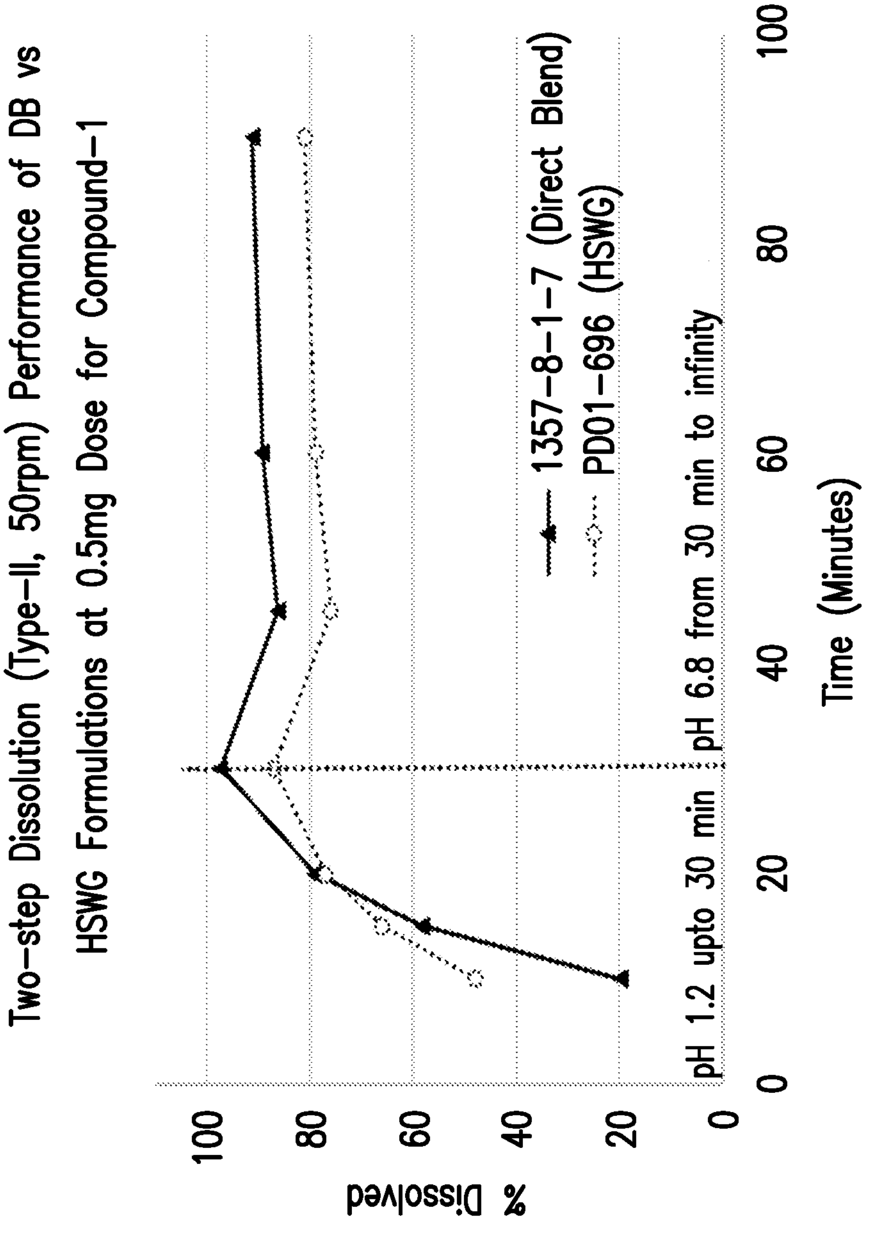

FIG. 14 shows two-stage dissolution testing to assess the impact on drug precipitation risk using DB free base formulation with 3% FA and HSWG free base formulation at 0.5 mg dose strength.

Figure 15:
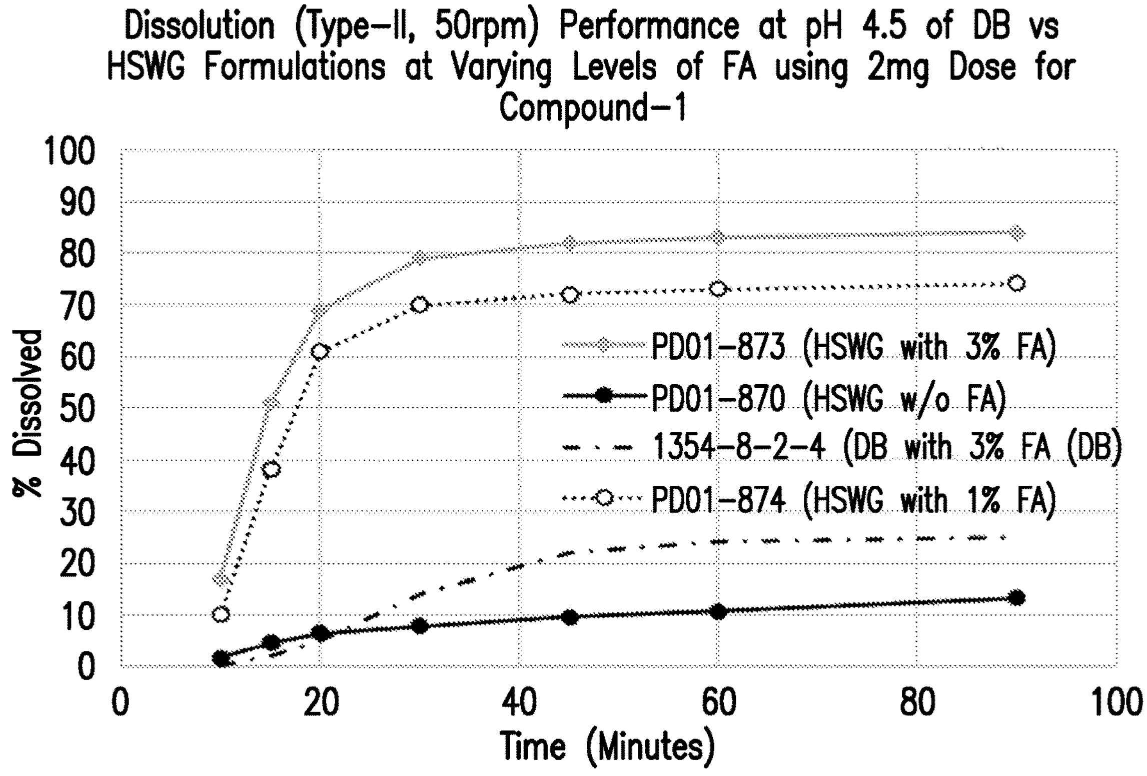

FIG. 15 shows comparative DB free base formulation with 3% FA and HSWG free base formulation dissolution performance (without fumaric acid, with 1% and 3% FA) at pH 4.5 using 2 mg dose strength.

Figure 16:
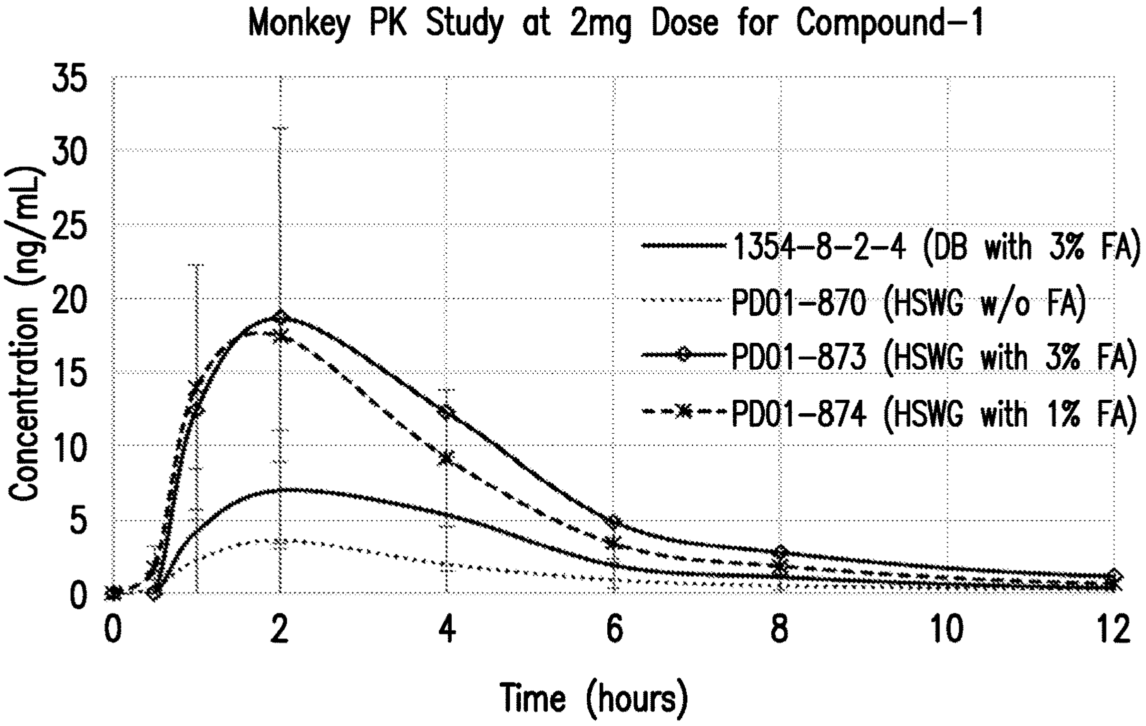

FIG. 16 shows mean monkey PK data using 2.0 mg DB free base formulation with 3% FA and HSWG free base formulation.

Figure 17:
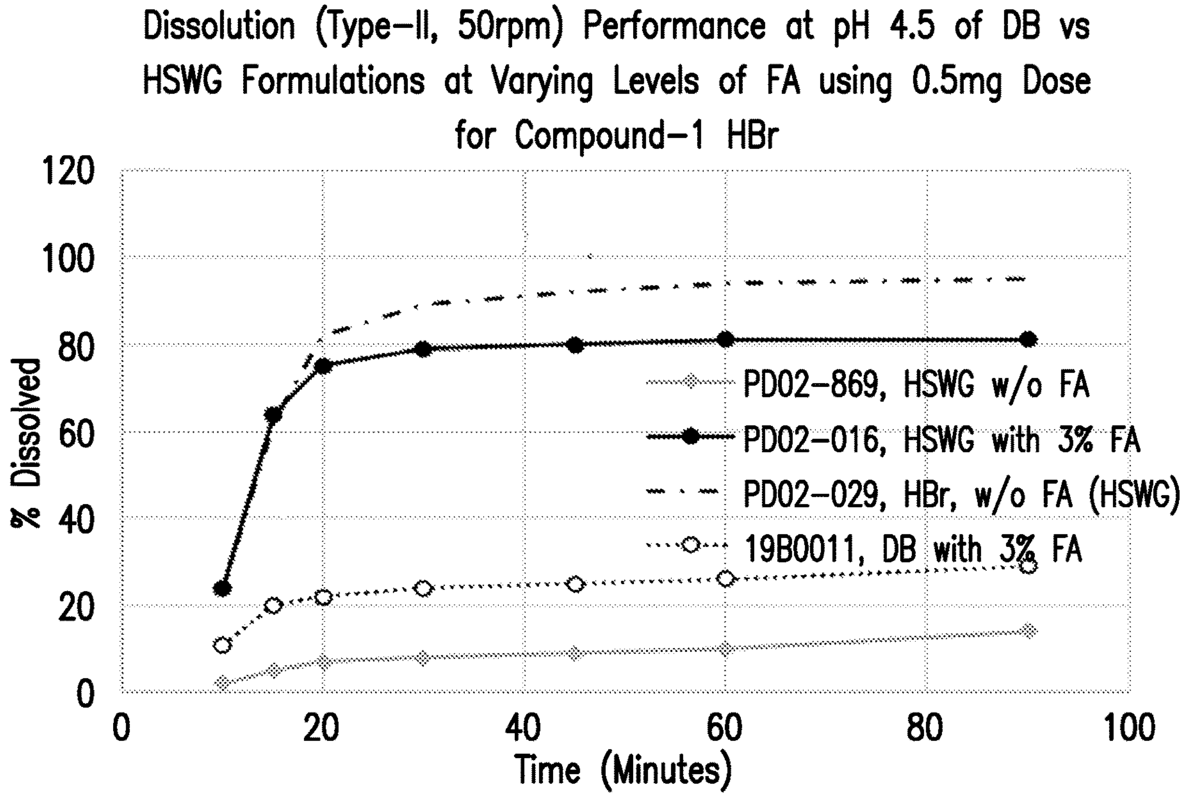

FIG. 17 shows in vitro dissolution performance of DB free base formulation with 3% FA, HSWG free base formulation with and without fumaric acid, and formulation with HBr salt at pH 4.5.

Figure 18:
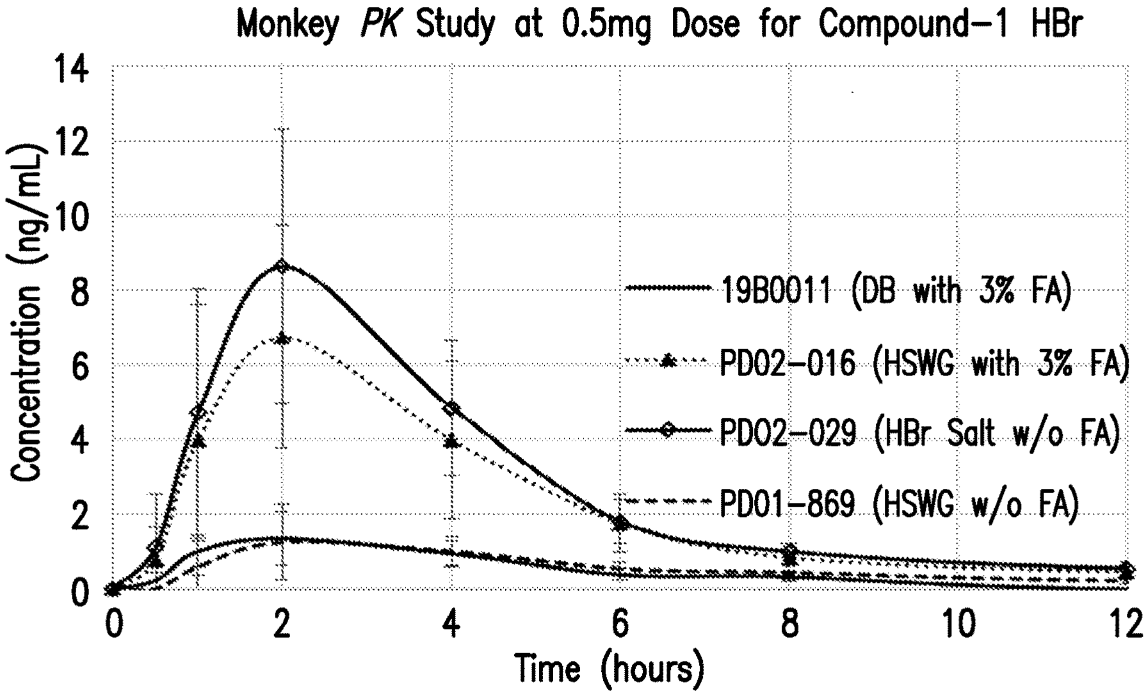

FIG. 18 shows mean monkey PK data using 0.5 mg DB free base formulation with 3% FA and HSWG free base formulation.

Figure 19:
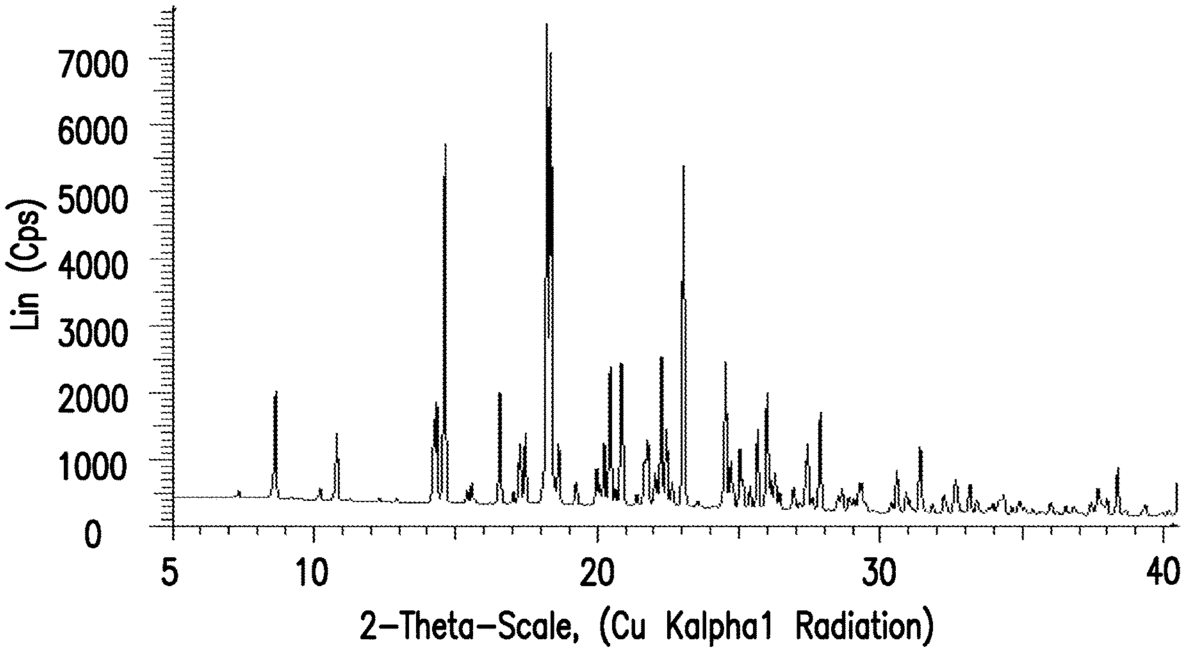

FIG. 19 provides a representative X-ray powder diffraction (XRPD) pattern of Form K of free base of Compound 1.

Figure 20:
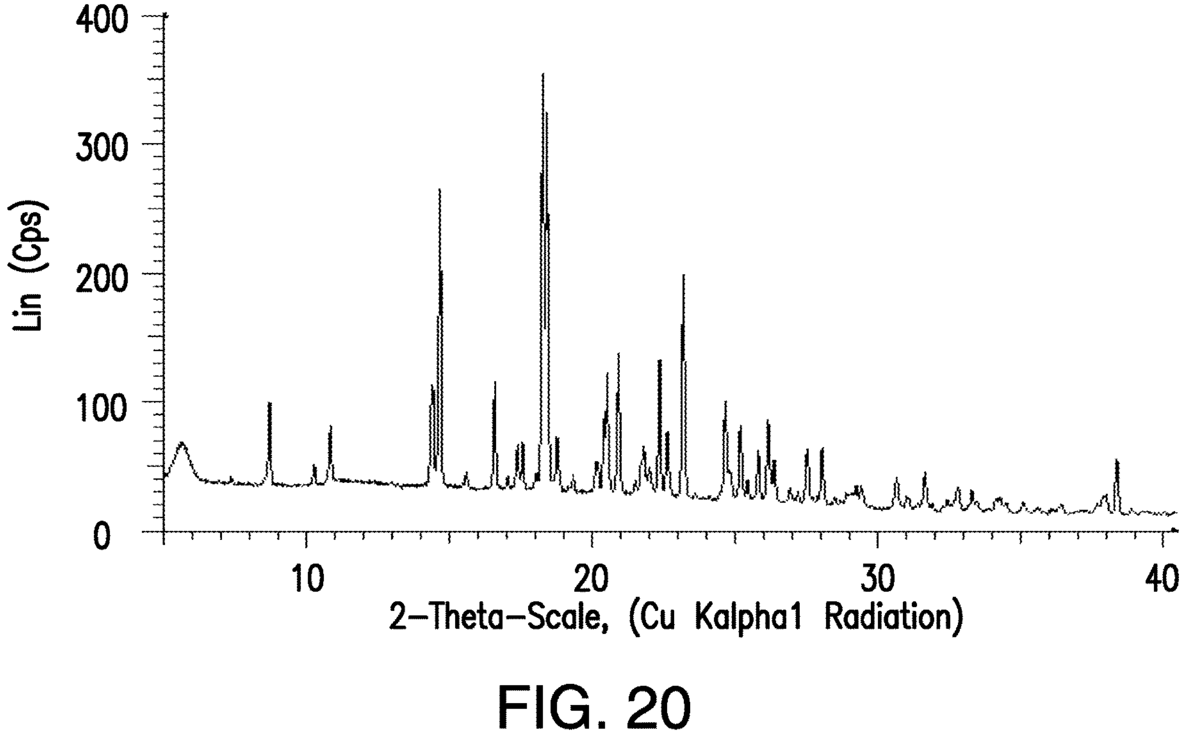

FIG. 20 provides a representative XRPD pattern of Form K' of free base of Compound 1.

Figure 21:
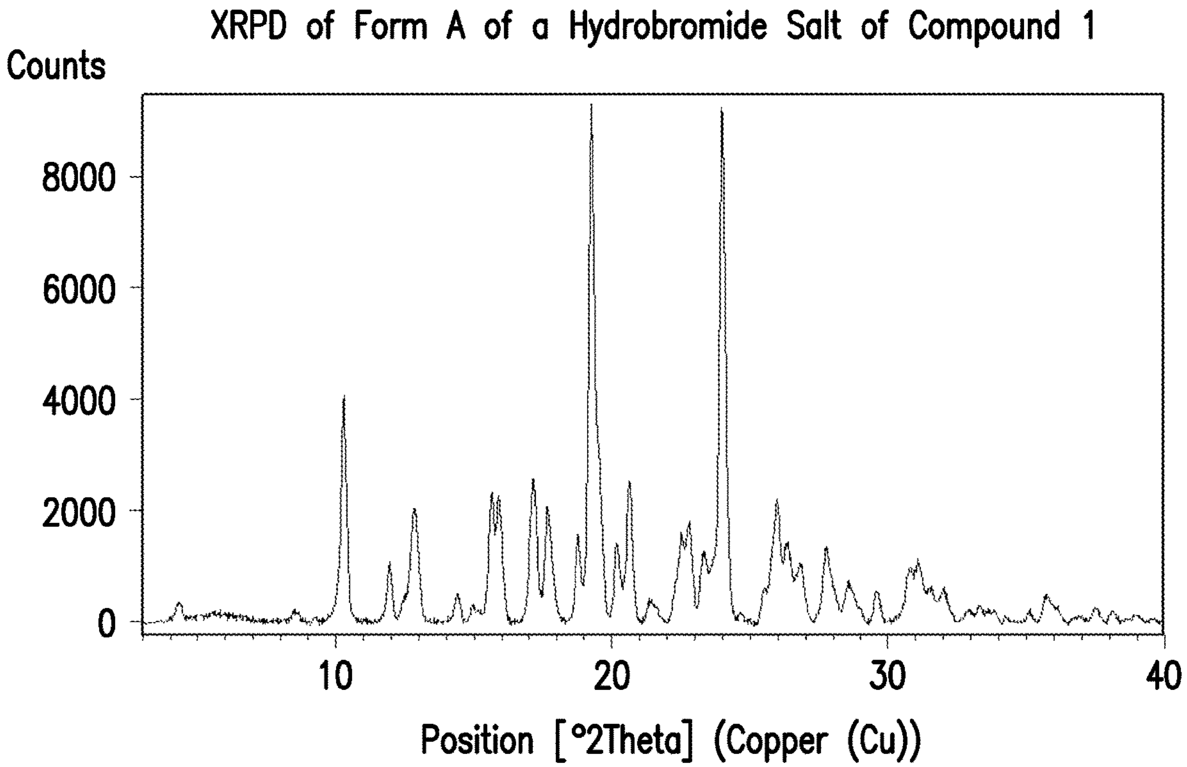

FIG. 21 provides a representative XRPD pattern of Form A of a hydrobromide salt of Compound 1.

6. DETAILED DESCRIPTION

6.1 Definitions

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. As used herein, a tilde (i.e., "~") preceding a numerical value or range of values indicates "about" or "approximately."

Unless otherwise specified, the terms "X-ray powder diffraction", "powder X-ray diffraction", "PXRD", and "XRPD" are used interchangeably in this application.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy,* $21^{st}$ edition, Lippincott, Williams and Wilkins, Baltimore, MD (2005); *The United States Pharmacopeia,* $23^{rd}$ edition, 1843-1844 (1995).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, benzenesulfonic, benzoic, camphorsulfonic, carbonic, citric, dihydrogenphosphoric, ethenesulfonic, fumaric, galactunoric, gluconic, glucuronic, glutamic, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, nitric, pamoic, pantothenic, phosphoric, phthalic, propionic, suberic, succinic, sulfuric, tartaric, toluenesulfonic acid, and the like (see, e.g., S. M. Berge et al., *J. Pharm. Sci.,* 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridine-sulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11;14)(q13;q32); t(6;14)(p21;32); t(12;14)(p13;q32); or t(6;20);); MMSET translocations (for example, t(4;14)(p16;q32)); MAF translocations (for example, t(14;16)(q32;q32); t(20;22); t(16;22)(q11;q13); or t(14;20)(q32;q11)); or other chromosome factors (for example, deletion of 17p13, or chromosome 13; del(17/17p), nonhyperdiploidy, and gain(1q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients, who have had a remission of multiple myeloma after therapy, have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

"Remission" as used herein, is a decrease in or disappearance of signs and symptoms of a cancer, for example, multiple myeloma. In partial remission, some, but not all, signs and symptoms of the cancer have disappeared. In complete remission, all signs and symptoms of the cancer have disappeared, although the cancer still may be in the body.

As used herein "transplant" refers to high-dose therapy with stem cell rescue. Hematopoietic (blood) or bone marrow stem cells are used not as treatment but to rescue the patient after the high-dose therapy, for example high dose chemotherapy and/or radiation. Transplant includes "autologous" stem cell transplant (ASCT), which refers to use of the patients' own stem cells being harvested and used as the replacement cells. In some embodiments, transplant also includes tandem transplant or multiple transplants.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, such as multiple myeloma, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP, as used herein, means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR), according to the IMWG Uniform Response Criteria. In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of multiple myeloma may be assessed by the International Uniform Response Criteria for Multiple Myeloma (IURC) (see Dune B G M, Harousseau J-L, Miguel J S, et al. International uniform response criteria for multiple myeloma. *Leukemia,* 2006; (10) 10: 1-7), using the response and endpoint definitions shown below:

| Response Subcategory | Response Criteria[a] |
|---|---|
| SCR | CR as defined below plus<br>Normal FLC ratio and<br>Absence of clonal cells in bone marrow[b] by immunohistochemistry or immunofluorescence[c] |
| CR | Negative immunofixation on the serum and urine and<br>Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations: CR, complete response; FLC, free light chain; PR, partial response; SD, stable disease; SCR, stringent complete response; VGPR, very good partial response.

[a]All response categories require two consecutive assessments made at any time before the institution of any new therapy; all categories also require no known evidence of progressive or new bone lesions if radiographic studies were performed. Radiographic studies are not required to satisfy these response requirements.

[b]Confirmation with repeat bone marrow biopsy not needed.

[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.

[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, e.g., light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

Unless otherwise specified, to the extent that there is a discrepancy between a depicted chemical structure of a compound provided herein and a chemical name of a compound provided herein, the chemical structure shall control.

6.2 Pharmaceutical Compositions Comprising Compound 1

In certain embodiment, provided herein are pharmaceutical compositions (e.g., oral dosage formulations) comprising Compound 1:

1

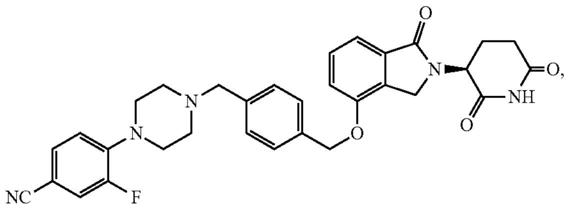

or an enantiomer, mixture of enantiomers, tautomer, isotopolog, or pharmaceutically acceptable salt thereof, and a carrier or diluent.

In some embodiments, the pharmaceutical compositions provided herein are suitable for oral administration to a patient. In one embodiment, the pharmaceutical compositions provided herein exhibit advantageous physical and/or pharmacological properties. Such properties include, but are not limited to, ease of assay, content uniformity, flow properties for manufacture, dissolution and bioavailability, and stability. In one embodiment, the pharmaceutical compositions provided herein have a shelf life of at least about 6 months, at least about 12 months, at least about 18 months, at least about 24 months, at least about 30 months, or at least about 36 months without refrigeration. In certain embodiments, "without refrigeration" refers to a temperature at or above 20° C. In one embodiment, the pharmaceutical compositions provided herein is stored under refrigerated condition. In one embodiment, the pharmaceutical compositions provided herein have a shelf life of at least about 6 months, at least about 12 months, at least about 18 months, at least about 24 months, at least about 30 months, or at least about 36 months when stored under refrigerated condition. In one embodiment, the properties of the pharmaceutical compositions provided herein make them suitable for immediate-release (IR).

Pharmaceutical compositions provided herein can be formulated into suitable pharmaceutical formulations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999). In one embodiment, the pharmaceutical compositions provided herein are oral dosage forms. In one embodiment, the oral dosage unit form is a tablet. In one embodiment, the oral dosage unit form is a caplet. In one embodiment, the oral dosage unit form is a capsule. In one embodiment, the pharmaceutical compositions provided herein are immediate-release capsules. In one embodiment, the pharmaceutical compositions provided herein are immediate-release (IR) blend in capsules (BIC).

Tablets, caplets, and capsules typically contain from about 50 mg to about 500 mg of the pharmaceutical composition (i.e., active ingredient and excipient(s)). Capsules can be of any size. Examples of standard sizes include #000, #00, #0, #1, #2, #3, #4, and #5. See, e.g., *Remington's Pharmaceutical Sciences*, page 1658-1659 (Alfonso Gennaro ed., Mack Publishing Company, Easton Pennsylvania, 18th ed., 1990), which is incorporated by reference. In some embodiments, capsules provided herein are of size #1 or larger, #2 or larger, #3 or larger, or #4 or larger.

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

(a) Forms of Compound 1

Compound 1 has the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Methods of preparing Compound 1 have been described in U.S. Pat. No. 10,357,489, which is incorporated herein by reference in its entirety.

In one embodiment, Compound 1, or an enantiomer, mixture of enantiomers, tautomer, isotopolog, or pharmaceutically acceptable salt thereof, is provided in the pharmaceutical composition in a solid form. Solid forms of Compound 1, or an enantiomer, mixture of enantiomers, tautomer, isotopolog, or pharmaceutically acceptable salt thereof, has been described in U.S. application Ser. No. 16/737,739, which is incorporated herein by reference in its entirety.

In one embodiment, the solid form is amorphous. In one embodiment, the solid form is crystalline. In one embodiment, the solid form is a hydrate. In one embodiment, the solid form is an anhydrate. In one embodiment, the solid form is a solvate. In one embodiment, the solid form is non-solvated.

The solid forms may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

In one embodiment, the pharmaceutical composition comprises Compound 1 (i.e., as a free base). As used herein and unless otherwise specified, "Compound 1" and "free base of Compound 1" are used interchangeably. In one embodiment, the free base of Compound 1 is amorphous. In one embodiment, the free base of Compound 1 is crystalline. In one embodiment, the free base of Compound 1 is a mixture of one or more of amorphous form and crystalline forms.

In one embodiment, the pharmaceutical composition comprises a salt of Compound 1. In one embodiment, the salt is a hydrochloride salt, a mesylate salt, a hydrobromide salt, a besylate salt, a glycolate salt, a L-malate salt, a napadisylate salt, a sulfate salt, a tosylate salt, an oxalate salt, an isethionate salt, a maleate salt, a phosphate salt, a malonate salt, a gentisate salt, a L-tartrate salt, a fumarate salt, a citrate salt, a R-mandelate salt, a L-ascorbate salt, a succinate salt, a nitrate salt, a salicylate salt, an edisylate salt, a cyclamate salt, an esylate salt, a D-glucuronate salt, an 4-aminosalicylate salt, a caproate salt, a cinnamate salt, a caprylate salt, a camphorate salt, a D-aspartate salt, or a D-glutamate salt. In one embodiment, the salt of Compound 1 is amorphous. In one embodiment, the salt of Compound 1 is crystalline. In one embodiment, the salt of Compound 1 is a mixture of one or more of amorphous form and crystalline forms.

In one embodiment, the pharmaceutical composition comprises a hydrochloride salt of Compound 1. In one embodiment, the pharmaceutical composition comprises a mesylate salt of Compound 1. In one embodiment, the pharmaceutical composition comprises a hydrobromide salt of Compound 1. In one embodiment, the pharmaceutical composition comprises a besylate salt of Compound 1. In one embodiment, the pharmaceutical composition comprises a glycolate salt of Compound 1. In one embodiment, the pharmaceutical composition comprises a L-malate salt of Compound 1.

In one embodiment, the pharmaceutical composition comprises Form K of free base of Compound 1, Form K' of free base of Compound 1, or an intermediate form between Form K and Form K', or a mixture thereof.

In one embodiment, Form K is a channel hydrate of free base of Compound 1. In one embodiment, Form K is a monohydrate of free base of Compound 1. In one embodiment, Form K' is a dehydrated hydrate of Form K. In one embodiment, without being limited by a particular theory, Form K' converts to Form K with increasing humidity, and Form K converts to Form K' with decreasing humidity. Accordingly, intermediate forms between Form K and Form K' exist depending on the degree of humidity. In one embodiment, From K converts to Form K' when water activity is not higher than about 0.11. In one embodiment, From K' converts to Form K when water activity is not lower than about 0.17.

In one embodiment, the pharmaceutical composition provided herein comprises Form K, Form K', or an intermediate form between Form K and Form K', or a mixture thereof, of free base of Compound 1, characterized by an XRPD pattern comprising peaks at approximately 14.6, 18.2, and 18.3° 2θ. In one embodiment, the XRPD pattern further comprises peaks at approximately 22.3 and 23.1° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.5, 20.9, 22.3, and 23.1° 2θ. In one embodiment, the pharmaceutical composition provided herein comprises Form K of free base of Compound 1, characterized by an XRPD pattern further comprising at least a peak at approximately 14.2, 18.6, or 20.3° 2θ. In one embodiment, the pharmaceutical composition provided herein comprises Form K' of free base of Compound 1, characterized by an XRPD pattern further comprising at least a peak at approximately 18.0 or 18.8° 2θ.

A representative XRPD pattern of Form K is provided in FIG. 19.

In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.6, 10.8, 14.2, 14.3, 14.6, 16.6, 17.3, 17.5, 18.2, 18.3, 18.6, 20.3, 20.5, 20.9, 21.8, 22.3, 22.5, 23.1, 24.5, 25.1, 25.7, 26.0, 27.4, 27.9, and 31.4° 2θ. In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.59, 10.78, 14.21, 14.32, 14.60, 16.55, 17.26, 17.45, 18.21, 18.34, 18.62, 20.25, 20.47, 20.87, 21.79, 22.28, 22.45, 23.05, 24.54, 25.05, 25.67, 26.01, 27.43, 27.89, and 31.44° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises free base of Compound 1, which is a solid form characterized by an XRPD pattern comprising peaks at approximately 14.2, 14.6, 18.2, and 18.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.21, 14.60, 18.21, and 18.34° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ±0.02° 2θ. In one embodiment, the XRPD pattern further comprises peaks at 22.3, 23.1, and 24.5° 2θ±0.02° 2θ. In one embodiment, the XRPD pattern further comprises peaks at 20.5 and 20.9° 2θ±0.02° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.21, 14.60, 18.21, and 18.34° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.02° 2θ. In one embodiment, the XRPD pattern does not contain a peak at 18.02° 2θ0.02° 2θ. In one embodiment, the XRPD pattern does not contain a peak at 18.75° 2θ±0.02° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.21, 14.60, 18.21, and 18.34° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern comprising peaks at approximately 14.6, 18.2, 18.3, and 18.6° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.6, 18.2, 18.3, and 18.6° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.60, 18.21, 18.34, and 18.62° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.6, 18.2, 18.3, and 18.6° 2θ±0.02° 2θ. In one embodiment, the XRPD pattern further comprises peaks at 22.3, 23.1, and 24.5° 2θ0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.60, 18.21, 18.34, and 18.62° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ0.02° 2θ.

In one embodiment, the pharmaceutical composition provided herein comprises free base of Compound 1, which is a solid form characterized by an XRPD pattern comprising peaks at 14.6, 18.2, 18.3, and 18.6° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.60, 18.21, 18.34, and 18.62° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern comprising peaks at approximately 14.6, 18.2, 18.3, and 20.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.60, 18.21, 18.34, and 20.25° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ±0.02° 2θ. In one embodiment, the XRPD pattern further comprises peaks at 22.3, 23.1, and 24.5° 2θ0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.60, 18.21, 18.34, and 20.25° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ0.02° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.60, 18.21, 18.34, and 20.25° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern that matches the XRPD pattern presented in FIG. 19.

A representative XRPD pattern of Form K' is provided in FIG. 20.

In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.7, 10.8, 14.4, 14.6, 16.6, 17.4, 17.5, 18.0, 18.3, 18.4, 18.8, 20.5, 20.9, 21.8, 22.4, 22.6, 23.2, 24.7, 25.2, 25.8, 26.2, 26.4, 27.5, 28.1, 31.7, and 38.4° 2θ. In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.65, 10.79, 14.36, 14.63, 16.55, 17.35, 17.53, 18.02, 18.25, 18.40, 18.75, 20.52, 20.92, 21.81, 22.36, 22.64, 23.19, 24.68, 25.20, 25.82, 26.17, 26.39, 27.54, 28.08, 31.69, and 38.41° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises free base of Compound 1, which is a solid form characterized by an XRPD pattern comprising peaks at approximately 14.6, 18.0, 18.3, and 18.4° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.0, 18.3, 18.4, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, the pharmaceutical composition provided herein comprises free base of Compound 1, which is a solid form characterized by an XRPD pattern comprising peaks at 14.63, 18.02, 18.25, and 18.40° 2θ±0.04° 2θ. In one embodiment, the XRPD pattern further comprises peaks at 20.92, 22.36, and 23.19° 2θ±0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.04° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, the pharmaceutical composition provided herein comprises free base of Compound 1, which is a solid form characterized by an XRPD pattern comprising peaks at 14.63, 18.02, 18.25, and 18.40° 2θ±0.02° 2θ. In one embodiment, the XRPD pattern further comprises peaks at 20.92, 22.36, and 23.19° 2θ0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ0.02° 2θ. In one embodiment, the XRPD pattern does not contain a peak at 14.21° 2θ0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, the pharmaceutical composition provided herein comprises free base of Compound 1, which is a solid form characterized by an XRPD pattern comprising peaks at 14.63, 18.02, 18.25, and 18.40° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, the pharmaceutical composition provided herein comprises free base of Compound 1, which is a solid form characterized by an XRPD pattern comprising peaks at approximately 14.6, 18.3, 18.4, and 18.8° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.3, 18.4, 18.8, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, the pharmaceutical composition provided herein comprises free base of Compound 1, which is a solid form characterized by an XRPD pattern comprising peaks at 14.6, 18.3, 18.4, and 18.8° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, the pharmaceutical composition provided herein comprises free base of Compound 1, which is a solid form characterized by an XRPD pattern comprising peaks at 14.63, 18.25, 18.40, and 18.75° 2θ±0.04° 2θ. In one embodiment, the XRPD pattern further comprises peaks at 20.92, 22.36, and 23.19° 2θ±0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.04° 2θ.

In one embodiment, the pharmaceutical composition provided herein comprises free base of Compound 1, which is a solid form characterized by an XRPD pattern comprising peaks at 14.6, 18.3, 18.4, and 18.8° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, the pharmaceutical composition provided herein comprises free base of Compound 1, which is a solid form characterized by an XRPD pattern comprising peaks at 14.63, 18.25, 18.40, and 18.75° 2θ±0.02° 2θ. In one embodiment, the XRPD pattern further comprises peaks at 20.92, 22.36, and 23.19° 2θ±0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ±0.02° 2θ. In one embodiment, the XRPD pattern does not contain a peak at 14.21° 2θ0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, the pharmaceutical composition provided herein comprises free base of Compound 1, which is a solid form characterized by an XRPD pattern comprising peaks at 14.6, 18.3, 18.4, and 18.8° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, the pharmaceutical composition provided herein comprises free base of Compound 1, which is a solid form characterized by an XRPD pattern comprising peaks at 14.63, 18.25, 18.40, and 18.75° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, the pharmaceutical composition provided herein comprises free base of Compound 1, which is a solid form characterized by an XRPD pattern that matches the XRPD pattern presented in FIG. 20.

In one embodiment, without being limited to any particular theory, compared to Form K, the XRPD peaks in Form K' shift slightly to higher ° 2θ values, suggesting Form K' has slightly contracted lattice.

In certain embodiments, the pharmaceutical composition provided herein comprises Form A of a hydrobromide salt of Compound 1.

In one embodiment, the molar ratio of Compound 1 to hydrobromic acid in Form A is about 1:1. In one embodiment, Form A is a mono-hydrobromide salt of Compound 1. In one embodiment, Form A is a non-solvated form of a hydrobromide salt of Compound 1. In one embodiment, Form A is an anhydrate of a hydrobromide salt of Compound 1.

A representative XRPD pattern of Form A of a hydrobromide salt of Compound 1 is provided in FIG. 21.

In one embodiment, the pharmaceutical composition provided herein comprises a hydrobromide salt of Compound 1, which is a solid form characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 4.3, 10.3, 11.9, 12.8, 14.4, 15.6, 15.9, 17.1, 17.6, 18.8, 19.3, 20.2, 20.7, 22.4, 22.8, 23.3, 24.0, 26.0, 26.4, 26.9, 27.7, 28.5, 29.6, and 31.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises a hydrobromide salt of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 4.3, 10.3, 11.9, 12.8, 15.7, 15.9, 17.1, 17.2, 17.7, 18.8, 19.3, 19.5, 19.6, 20.2, 20.3, 20.7, 22.5, 22.8, 23.3, 23.9, 24.1, 26.0, 26.3, 26.8, 27.7, and 31.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises a hydrobromide salt of Compound 1, which is a solid form characterized by an XRPD pattern comprising peaks at approximately 10.3, 19.3, and 24.0° 2θ. In one embodiment, the XRPD pattern further comprises peaks at approximately 17.1 and 20.7° 2θ. In one embodiment, the XRPD pattern further comprises peaks at approximately 12.8 and 15.6° 2θ. In one embodiment, the XRPD pattern comprises peaks at approximately 10.3, 12.8, 15.6, 15.9, 17.1, 17.6, 19.3, 20.7, 24.0, and 26.0° 2θ.

In one embodiment, the pharmaceutical composition provided herein comprises a hydrobromide salt of Compound 1, which is a solid form characterized by an XRPD pattern that matches the XRPD pattern presented in FIG. 21.

In one embodiment, the XRPD patterns are obtained using Cu Kα radiation.

(b) Compound 1 Hydrobromide Salt Pharmaceutical Composition

In one embodiment, provided herein is a pharmaceutical composition comprising 1) a hydrobromide salt of Compound 1:

1

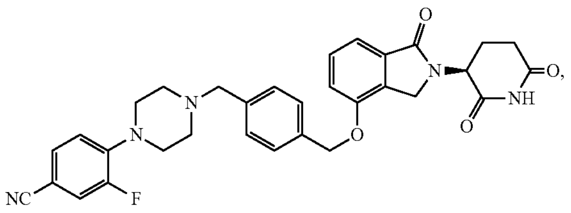

2) a mixture of mannitol and cellulose or a mixture of mannitol and starch, 3) hydroxypropyl methylcellulose (HPMC), 4) sodium starch glycolate (SSG), and 5) stearic acid.

In one embodiment, provided herein is a pharmaceutical composition comprising: 1) a hydrobromide salt of Compound 1 at an amount of from about 0.05 to about 3% w/w; 2) a carrier or diluent at an amount of from about 70 to about 98% w/w; 3) IPMC at an amount of from about 0.5 to about 10% w/w; 4) SSG at an amount of from about 0.5 to about 10% w/w; and 5) stearic acid at an amount of from about 0.5 to about 8% w/w; and wherein the carrier or diluent is a mixture of mannitol and cellulose or a mixture of mannitol and starch.

In one embodiment, the hydrobromide salt of Compound 1 is a crystalline hydrobromide salt of Compound 1. In one embodiment, the hydrobromide salt of Compound 1 is characterized by an XRPD pattern comprising peaks at approximately 10.3, 19.3, and 24.0° 2θ.

In one embodiment, the amount of the hydrobromide salt of Compound 1 is from about 0.05 to about 3% w/w (of the total weight of the pharmaceutical composition). In one embodiment, the amount of the hydrobromide salt of Compound 1 is from about 0.1 to about 1.5% w/w. In one embodiment, the amount of the hydrobromide salt of Compound 1 is from about 0.16 to about 0.65% w/w.

In one embodiment, the amount of the hydrobromide salt of Compound 1 is about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3% w/w. In one embodiment, the amount is about 0.16% w/w. In one embodiment, the amount is about 0.65% w/w.

In one embodiment, the component 2) is a mixture of mannitol and cellulose. In one embodiment, the cellulose is microcrystalline cellulose (MCC).

In one embodiment, the component 2) is a mixture of mannitol and starch. In one embodiment, the starch is partially pregelatinized starch.

In one embodiment, the amount of the mixture of mannitol and cellulose or the mixture of mannitol and starch is from about 70 to about 98% w/w (of the total weight of the pharmaceutical composition). In one embodiment, the amount of the mixture of mannitol and cellulose or the mixture of mannitol and starch is from about 80 to about 90% w/w. In one embodiment, the amount of the mixture of mannitol and cellulose or the mixture of mannitol and starch is from about 85 to about 86% w/w.

In one embodiment, the amount of the mixture of mannitol and cellulose or the mixture of mannitol and starch is about 70, about 71, about 72, about 73, about 74, about 75, about 76, about 77, about 78, about 79, about 80, about 80.5, about 81, about 81.5, about 82, about 82.5, about 83, about 83.5, about 84, about 84.5, about 85, about 85.5, about 86, about 86.5, about 87, about 87.5, about 88, about 88.5, about 89, about 89.5, about 90, about 91, about 92, about 93, about 94, about 95, about 96, about 97, or about 98% w/w. In one embodiment, the amount is about 85% w/w. In one embodiment, the amount is about 86% w/w. In one embodiment, the amount is about 85.35% w/w. In one embodiment, the amount is about 85.84% w/w.

In one embodiment, the amount of the mannitol is from about 35 to about 93% w/w, and the amount of the cellulose or starch is from about 5 to about 35% w/w. In one embodiment, the amount of the mannitol is from about 50 to about 80% w/w, and the amount of the cellulose or starch is from about 10 to about 30% w/w. In one embodiment, the amount of the mannitol is from about 65 to about 66% w/w, and the amount of the cellulose or starch is about 20% w/w.

In one embodiment, the amount of the mannitol is about 35, about 40, about 45, about 50, about 55, about 60, about 61, about 62, about 63, about 64, about 65, about 66, about 67, about 68, about 69, about 70, about 75, about 80, about 85, about 90, or about 93% w/w. In one embodiment, the amount is about 65.35% w/w. In one embodiment, the amount is about 65.84% w/w.

In one embodiment, the amount of the cellulose is about 5, about 10, about 15, about 16, about 17, about 18, about 19, about 20, about 21, about 22, about 23, about 24, about 25, about 30, or about 35% w/w. In one embodiment, the amount is about 20% w/w.

In one embodiment, the amount of the starch is about 5, about 10, about 15, about 16, about 17, about 18, about 19, about 20, about 21, about 22, about 23, about 24, about 25, about 30, or about 35% w/w. In one embodiment, the amount is about 20% w/w.

In one embodiment, the weight ratio of the cellulose or starch to the mannitol is from about 1:1 to about 1:20. In one embodiment, the weight ratio of the cellulose or starch to the mannitol is from about 1:1.3 to about 1:15. In one embodiment, the weight ratio of the cellulose or starch to the mannitol is from about 1:1.7 to about 1:8. In one embodiment, the weight ratio of the cellulose or starch to the mannitol is from about 1:2 to about 1:4. In one embodiment, the weight ratio of the cellulose or starch to the mannitol is about 1:3.3.

In one embodiment, the HPMC is HPMC E5.

In one embodiment, the amount of the HPMC is from about 0.5 to about 10% w/w (of the total weight of the pharmaceutical composition). In one embodiment, the amount of the HPMC is from about 1 to about 9% w/w. In one embodiment, the amount of the HPMC is from about 2 to about 8% w/w. In one embodiment, the amount of the HPMC is from about 3 to about 7% w/w. In one embodiment, the amount of the HPMC is from about 4 to about 6% w/w.

In one embodiment, the amount of the HPMC is about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10% w/w. In one embodiment, the amount of the HPMC is about 5% w/w.

In one embodiment, the SSG is low pH SSG.

In one embodiment, the amount of the SSG is from about 0.5 to about 10% w/w (of the total weight of the pharmaceutical composition). In one embodiment, the amount of the SSG is from about 1 to about 9% w/w. In one embodiment, the amount of the SSG is from about 2 to about 8% w/w. In one embodiment, the amount of the SSG is from about 3 to about 7% w/w. In one embodiment, the amount of the SSG is from about 4 to about 6% w/w.

In one embodiment, the amount of the SSG is about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10% w/w. In one embodiment, the amount of the SSG is about 5% w/w.

In one embodiment, the pharmaceutical composition has a pH (e.g., slurry pH) of from about 4.2 to about 5.8. In one embodiment, the pH is from about 4.4 to about 4.8. In one embodiment, the pH is from about 4.5 to about 4.7. In one embodiment, the pH is about 4.5. In one embodiment, the pH is about 4.6. In one embodiment, the pH is about 4.7.

In one embodiment, the amount of the stearic acid is from about 0.5 to about 8% w/w (of the total weight of the pharmaceutical composition). In one embodiment, the amount of the stearic acid is from about 1 to about 7% w/w. In one embodiment, the amount of the stearic acid is from about 2 to about 6% w/w. In one embodiment, the amount of the stearic acid is from about 3 to about 5% w/w.

In one embodiment, the amount of the stearic acid is about 0.5, about 1, about 1.5, about 2, about 2.5, about 3, about 3.5, about 4, about 4.5, about 5, about 5.5, about 6, about 6.5, about 7, about 7.5, or about 8% w/w. In one embodiment, the amount of the stearic acid is about 4% w/w.

In one embodiment, the pharmaceutical composition has an average particle size of from about 100 to about 250 μM. In one embodiment, the pharmaceutical composition has a D10 of from about 15 to about 100 μM. In one embodiment, the pharmaceutical composition has a D10 of from about 30 to about 100 μM. In one embodiment, the pharmaceutical composition has a D50 of from about 80 to about 250 μM. In one embodiment, the pharmaceutical composition has a D50 of from about 100 to about 250 μM. In one embodiment, the pharmaceutical composition has a D90 of from about 180 to about 650 μM. In one embodiment, the pharmaceutical composition has a D90 of from about 280 to about 650 μM.

In one embodiment, provided herein is a pharmaceutical composition, comprising: 1) a hydrobromide salt of Compound 1 (e.g., Form A) at an amount of from about 0.1 to about 0.2% w/w; 2) mannitol at an amount of from about 64 to about 67% w/w and microcrystalline cellulose an amount of from about 19 to about 21% w/w; 3) IPMC E5 at an amount of from about 4 to about 6% w/w; 4) low pH SSG at an amount of from about 4 to about 6% w/w; and 5) stearic acid at an amount of from about 3 to about 5% w/w. In one embodiment, provided herein is a pharmaceutical composition, comprising: 1) a hydrobromide salt of Compound 1 (e.g., Form A) at an amount of about 0.16% w/w; 2) mannitol at an amount of about 65.84% w/w and microcrystalline cellulose an amount of about 20% w/w; 3) IPMC E5 at an amount of about 5% w/w; 4) low pH SSG at an amount of about 5% w/w; and 5) stearic acid at an amount of about 4% w/w. In one embodiment, the pharmaceutical composition has a total weight of from about 70 to about 280 mg, and in one embodiment, provide a dose strength equivalent to from about 0.1 to about 0.4 mg of Compound 1 (free base). In one embodiment, the pharmaceutical composition has a total weight of about 70 mg. In one embodiment, the pharmaceutical composition is contained in a size 4 capsule. In one embodiment, the pharmaceutical composition has a total weight of about 140 mg. In one embodiment, the pharmaceutical composition is contained in a size 2 capsule. In one embodiment, the pharmaceutical composition has a total weight of about 210 mg. In one embodiment, the pharmaceutical composition has a total weight of about 280 mg.

In one embodiment, provided herein is a pharmaceutical composition, comprising: 1) a hydrobromide salt of Compound 1 (e.g., Form A) at an amount of from about 0.6 to about 0.7% w/w; 2) mannitol at an amount of from about 64 to about 67% w/w and microcrystalline cellulose an amount of from about 19 to about 21% w/w; 3) HPMC E5 at an amount of from about 4 to about 6% w/w; 4) low pH SSG at an amount of from about 4 to about 6% w/w; and 5) stearic acid at an amount of from about 3 to about 5% w/w. In one embodiment, provided herein is a pharmaceutical composition, comprising: 1) a hydrobromide salt of Compound 1 (e.g., Form A) at an amount of about 0.65% w/w; 2) mannitol at an amount of about 65.35% w/w and microcrystalline cellulose an amount of about 20% w/w; 3) IPMC E5 at an amount of about 5% w/w; 4) low pH SSG at an amount of about 5% w/w; and 5) stearic acid at an amount of about 4% w/w. In one embodiment, the pharmaceutical composition has a total weight of from about 70 to about 280 mg, and in one embodiment, provide a dose strength equivalent to from about 0.4 to about 1.6 mg of Compound 1 (free base). In one embodiment, the pharmaceutical composition has a total weight of about 70 mg. In one embodiment, the pharmaceutical composition is contained in a size 3 capsule. In one embodiment, the pharmaceutical composition has a total weight of about 140 mg. In one embodiment, the pharmaceutical composition has a total weight of about 210 mg. In one embodiment, the pharmaceutical composition has a total weight of about 280 mg.

(c) Compound 1 Free Base Pharmaceutical Composition

In one embodiment, provided herein is a pharmaceutical composition comprising

1) Compound 1:

1

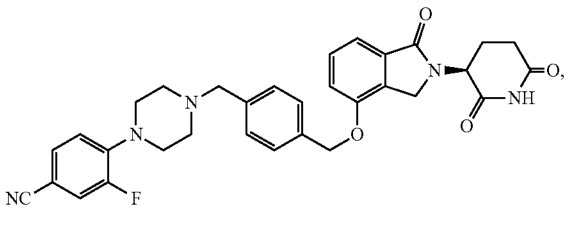

2) a mixture of mannitol and starch, 3) sodium stearyl fumarate, and 4) optionally fumaric acid.

In one embodiment, provided herein is a pharmaceutical composition comprising: 1) Compound 1 at an amount of from about 0.05 to about 4% w/w; 2) a mixture of mannitol and starch at an amount of from about 90 to about 99.5% w/w; 3) sodium stearyl fumarate at an amount of from about 0.1 to about 5% w/w; and 4) fumaric acid at an amount of from about 0 to about 10% w/w.

In one embodiment, Compound 1 is a crystalline Compound 1. In one embodiment, Compound 1 is characterized by an XRPD pattern comprising peaks at approximately 14.6, 18.2, and 18.3° 2θ.

In one embodiment, the amount of Compound 1 is from about 0.05 to about 4% w/w (of the total weight of the pharmaceutical composition). In one embodiment, the amount of Compound 1 is from about 0.1 to about 2% w/w. In one embodiment, the amount of Compound 1 is from about 0.13 to about 1.33% w/w. In one embodiment, the amount of Compound 1 is from about 0.13 to about 0.27% w/w. In one embodiment, the amount of Compound 1 is from about 0.27 to about 0.5% w/w. In one embodiment, the amount of Compound 1 is from about 0.5 to about 0.67% w/w. In one embodiment, the amount of Compound 1 is from about 0.67 to about 1.33% w/w. In one embodiment, the amount of Compound 1 is from about 1.33 to about 2.67% w/w.

In one embodiment, the amount of Compound 1 is about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, or about 4% w/w. In one embodiment, the amount is about 0.13% w/w. In one embodiment, the amount is about 0.27% w/w. In one embodiment, the amount is about 0.5% w/w. In one embodiment, the amount is about 0.67% w/w. In one embodiment, the amount is about 1.33% w/w. In one embodiment, the amount is about 2.67% w/w.

In one embodiment, the starch is partially pregelatinized starch.

In one embodiment, the amount of the mixture of mannitol and starch is from about 90 to about 99.5% w/w (of the total weight of the pharmaceutical composition). In one embodiment, the amount of the mixture of mannitol and starch is from about 95 to about 99% w/w. In one embodiment, the amount of the mixture of mannitol and starch is from about 97 to about 99% w/w.

In one embodiment, the amount of the mixture of mannitol and starch is about 90, about 90.5, about 91, about 91.5, about 92, about 92.5, about 93, about 93.5, about 94, about 94.5, about 95, about 95.5, about 96, about 96.5, about 97, about 97.5, about 97.6, about 97.7, about 97.8, about 97.9, about 98, about 98.1, about 98.2, about 98.3, about 98.4, about 98.5, about 98.6, about 98.7, about 98.8, about 98.9, about 99, or about 99.5% w/w. In one embodiment, the amount is about 98% w/w. In one embodiment, the amount is about 99% w/w. In one embodiment, the amount is about 97.67% w/w. In one embodiment, the amount is about 98.5% w/w. In one embodiment, the amount is about 98.73% w/w. In one embodiment, the amount is about 98.87% w/w.

In one embodiment, the amount of the mannitol is from about 60 to about 89% w/w, and the amount of the starch is from about 10 to about 30% w/w. In one embodiment, the amount of the mannitol is from about 77 to about 79% w/w, and the amount of the starch is about 20% w/w.

In one embodiment, the amount of the mannitol is about 60, about 65, about 70, about 71, about 72, about 73, about 74, about 75, about 76, about 77, about 78, about 79, about 80, about 81, about 82, about 83, about 84, about 85, or about 89% w/w. In one embodiment, the amount is about 78% w/w. In one embodiment, the amount is about 79% w/w. In one embodiment, the amount is about 77.67% w/w. In one embodiment, the amount is about 78.5% w/w. In one embodiment, the amount is about 78.73% w/w. In one embodiment, the amount is about 78.87% w/w.

In one embodiment, the amount of the starch is about 10, about 15, about 16, about 17, about 18, about 19, about 20, about 21, about 22, about 23, about 24, about 25, or about 30% w/w. In one embodiment, the amount is about 20% w/w.

In one embodiment, the weight ratio of the starch to the mannitol is from about 1:2 to about 1:9. In one embodiment, the weight ratio of the starch to the mannitol is from about 1:2.5 to about 1:6. In one embodiment, the weight ratio of the starch to the mannitol is from about 1:3 to about 1:4.5. In one embodiment, the weight ratio of the starch to the mannitol is about 1:3.9.

In one embodiment, the amount of sodium stearyl fumarate is from about 0.1 to about 5% w/w (of the total weight of the pharmaceutical composition). In one embodiment, the amount of sodium stearyl fumarate is from about 0.1 to about 3% w/w. In one embodiment, the amount of sodium stearyl fumarate is from about 0.5 to about 2% w/w.

In one embodiment, the amount of sodium stearyl fumarate is about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.5, about 4, about 4.5, or about 5% w/w. In one embodiment, the amount of sodium stearyl fumarate is about 1% w/w.

In one embodiment, the pharmaceutical composition does not contain fumaric acid.

In one embodiment, the amount of fumaric acid is from about 0.1 to about 10% w/w (of the total weight of the pharmaceutical composition). In one embodiment, the amount of fumaric acid is from about 0.1 to about 6% w/w. In one embodiment, the amount of fumaric acid is from about 0.5 to about 4% w/w. In one embodiment, the amount of fumaric acid is from about 1 to about 3% w/w.

In one embodiment, the amount of fumaric acid is about 0.1, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10% w/w. In one embodiment, the amount of fumaric acid is about 1% w/w. In one embodiment, the amount of fumaric acid is about 3% w/w.

In one embodiment, the pharmaceutical composition has a pH (e.g., slurry pH) of from about 2.1 to about 8.7. In one embodiment, the pH is from about 4.4 to about 4.8. In one embodiment, the pH is from about 4.5 to about 4.7. In one embodiment, the pH is about 4.5. In one embodiment, the pH is about 4.6. In one embodiment, the pH is about 4.7.

In one embodiment, the pharmaceutical composition has an average particle size of from about 70 to about 250 μM. In one embodiment, the pharmaceutical composition has an average particle size of from about 120 to about 200 μM. In one embodiment, the pharmaceutical composition has a D10 of from about 30 to about 100 μM. In one embodiment, the pharmaceutical composition has a D10 of from about 60 to about 90 μM. In one embodiment, the pharmaceutical composition has a D50 of from about 110 to about 280 μM. In one embodiment, the pharmaceutical composition has a D50 of from about 130 to about 250 μM. In one embodiment, the pharmaceutical composition has a D90 of from about 240 to about 580 μM. In one embodiment, the pharmaceutical composition has a D90 of from about 350 to about 560 μM.

In one embodiment, provided herein is a pharmaceutical composition, comprising: 1) Compound 1 (e.g., Form K) at an amount of from about 0.1 to about 0.2% w/w; 2) mannitol at an amount of from about 78 to about 79% w/w and partially pregelatinized starch at an amount of from about 19 to about 21% w/w; and 3) sodium stearyl fumarate at an amount of from about 0.5 to about 1.5% w/w. In one embodiment, provided herein is a pharmaceutical composition, comprising: 1) Compound 1 (e.g., Form K) at an amount of about 0.13% w/w; 2) mannitol at an amount of about 78.87% w/w and partially pregelatinized starch at an amount of about 20% w/w; and 3) sodium stearyl fumarate at an amount of about 1% w/w. In one embodiment, the pharmaceutical composition has a total weight of from about 75 to about 300 mg, and in one embodiment, provide a dose strength of from about 0.1 to about 0.4 mg of Compound 1 (free base). In one embodiment, the pharmaceutical composition has a total weight of about 75 mg. In one embodiment, the pharmaceutical composition is contained in a size 4 capsule. In one embodiment, the pharmaceutical composition has a total weight of about 300 mg. In one embodiment, the pharmaceutical composition is contained in a size 1 capsule.

In one embodiment, provided herein is a pharmaceutical composition, comprising: 1) Compound 1 (e.g., Form K) at an amount of from about 0.2 to about 0.3% w/w; 2) mannitol at an amount of from about 78 to about 79% w/w and partially pregelatinized starch at an amount of from about 19 to about 21% w/w; and 3) sodium stearyl fumarate at an amount of from about 0.5 to about 1.5% w/w. In one embodiment, provided herein is a pharmaceutical composition, comprising: 1) Compound 1 (e.g., Form K) at an amount of about 0.27% w/w; 2) mannitol at an amount of about 78.73% w/w and partially pregelatinized starch at an amount of about 20% w/w; and 3) sodium stearyl fumarate at an amount of about 1% w/w. In one embodiment, the pharmaceutical composition has a total weight of from about 75 to about 300 mg, and in one embodiment, provide a dose strength of from about 0.2 to about 0.8 mg of Compound 1 (free base). In one embodiment, the pharmaceutical composition has a total weight of about 75 mg. In one embodiment, the pharmaceutical composition is contained in a size 4 capsule. In one embodiment, the pharmaceutical composition has a total weight of about 300 mg. In one embodiment, the pharmaceutical composition is contained in a size 1 capsule.

In one embodiment, provided herein is a pharmaceutical composition, comprising: 1) Compound 1 (e.g., Form K) at an amount of from about 0.4 to about 0.6% w/w; 2) mannitol at an amount of from about 78 to about 79% w/w and partially pregelatinized starch at an amount of from about 19 to about 21% w/w; and 3) sodium stearyl fumarate at an amount of from about 0.5 to about 1.5% w/w. In one embodiment, provided herein is a pharmaceutical composition, comprising: 1) Compound 1 (e.g., Form K) at an amount of about 0.5% w/w; 2) mannitol at an amount of about 78.5% w/w and partially pregelatinized starch at an amount of about 20% w/w; and 3) sodium stearyl fumarate at an amount of about 1% w/w. In one embodiment, the pharmaceutical composition has a total weight of from about 80 to about 300 mg, and in one embodiment, provide a dose strength of from about 0.4 to about 1.5 mg of Compound 1 (free base). In one embodiment, the pharmaceutical composition has a total weight of about 80 mg. In one embodiment, the pharmaceutical composition is contained in a size 4 capsule. In one embodiment, the pharmaceutical composition has a total weight of about 300 mg. In one embodiment, the pharmaceutical composition is contained in a size 1 capsule.

In one embodiment, provided herein is a pharmaceutical composition, comprising: 1) Compound 1 (e.g., Form K) at an amount of from about 1.2 to about 1.4% w/w; 2) mannitol at an amount of from about 77 to about 78% w/w and partially pregelatinized starch at an amount of from about 19 to about 21% w/w; and 3) sodium stearyl fumarate at an amount of from about 0.5 to about 1.5% w/w. In one embodiment, provided herein is a pharmaceutical composition, comprising: 1) Compound 1 (e.g., Form K) at an amount of about 1.33% w/w; 2) mannitol at an amount of about 77.67% w/w and partially pregelatinized starch at an amount of about 20% w/w; and 3) sodium stearyl fumarate at an amount of about 1% w/w. In one embodiment, the pharmaceutical composition has a total weight of from about 75 to about 300 mg, and in one embodiment, provide a dose strength of from about 1 to about 4 mg of Compound 1 (free base). In one embodiment, the pharmaceutical composition has a total weight of about 75 mg. In one embodiment, the pharmaceutical composition is contained in a size 4 capsule. In one embodiment, the pharmaceutical composition a total weight of about 300 mg. In one embodiment, the pharmaceutical composition is contained in a size 1 capsule.

In one embodiment, provided herein is a pharmaceutical composition, comprising: 1) Compound 1 (e.g., Form K) at an amount of from about 0.4 to about 0.6% w/w; 2) mannitol at an amount of from about 75 to about 76% w/w and partially pregelatinized starch at an amount of from about 19 to about 21% w/w; 3) sodium stearyl fumarate at an amount of from about 0.5 to about 1.5% w/w; and 4) fumaric acid at an amount of from about 2.5 to about 3.5% w/w. In one embodiment, provided herein is a pharmaceutical composition, comprising: 1) Compound 1 (e.g., Form K) at an amount of about 0.5% w/w; 2) mannitol at an amount of about 75.5% w/w and partially pregelatinized starch at an amount of about 20% w/w; 3) sodium stearyl fumarate at an amount of about 1% w/w; and 4) fumaric acid at an amount of about 3% w/w.

In one embodiment, provided herein is a pharmaceutical composition, comprising: 1) Compound 1 (e.g., Form K) at an amount of from about 1.2 to about 1.4% w/w; 2) mannitol at an amount of from about 76 to about 77% w/w and partially pregelatinized starch at an amount of from about 19 to about 21% w/w; 3) sodium stearyl fumarate at an amount of from about 0.5 to about 1.5% w/w; and 4) fumaric acid at an amount of from about 0.5 to about 1.5% w/w. In one embodiment, provided herein is a pharmaceutical composition, comprising: 1) Compound 1 (e.g., Form K) at an amount of about 1.33% w/w; 2) mannitol at an amount of about 76.67% w/w and partially pregelatinized starch at an amount of about 20% w/w; 3) sodium stearyl fumarate at an amount of about 1% w/w; and 4) fumaric acid at an amount of about 1% w/w.

In one embodiment, provided herein is a pharmaceutical composition, comprising: 1) Compound 1 (e.g., Form K) at an amount of from about 1.2 to about 1.4% w/w; 2) mannitol at an amount of from about 74 to about 75% w/w and partially pregelatinized starch at an amount of from about 19 to about 21% w/w; 3) sodium stearyl fumarate at an amount of from about 0.5 to about 1.5% w/w; and 4) fumaric acid at an amount of from about 2.5 to about 3.5% w/w. In one embodiment, provided herein is a pharmaceutical composition, comprising: 1) Compound 1 (e.g., Form K) at an amount of about 1.33% w/w; 2) mannitol at an amount of about 74.67% w/w and partially pregelatinized starch at an amount of about 20% w/w; 3) sodium stearyl fumarate at an amount of about 1% w/w; and 4) fumaric acid at an amount of about 3% w/w.

(d) Additional Embodiments of the Pharmaceutical Compositions

In one embodiment, the pharmaceutical compositions provided herein can optionally further comprises one or more additional excipient. The additional excipients include, but are not limited to, wetting agent, solubilizer, crystallization stabilizer, anti-adherent, and precipitation inhibitor.

In one embodiment, the pharmaceutical compositions provided herein optionally further comprise one or more of polysorbates (e.g., Tween 80), poloxamer (e.g., Poloxamer 188), sodium lauryl sulfate (SLS), HPBCD, VitE-TPGS, HPMCAS (e.g., HPMCAS-LF), HPMC (e.g., HPMC E3), PVP (e.g., PVP VA64 or PVP K30), HPC (e.g., HPC EXF), and Talc.

In one embodiment, the pharmaceutical compositions provided herein are formulated into a capsule. In one embodiment, the capsule is an HPMC capsule. In one embodiment, the capsule is a gelatin capsule.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

(e) Process for Making Dosage Forms

Pharmaceutical compositions (dosage forms) provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., by employing roller compaction (RC), HSWG, compaction, and/or encapsulation processes). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of hydroxypropyl methyl cellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances. In some embodiments, a direct-blended dosage form may be more advantageous than a compacted (e.g., roller-compacted) dosage form since a direct blend process might result in better stability for molecules that are sensitive to degradation upon mechanical stress (e.g., compaction). In some embodiments, direct blending also helps minimizing degradation of the active ingredient.

In some embodiments, a roller-compaction process involves mixing the intragranular ingredients in a blender, deagglomerating using a comil, and passing through the roller compactor and mill to produce the granules. In roller-compaction process, the compacted material is often milled into smaller particles for further processing. The purpose for this step in manufacturing is to reduce the materials particle size. The milled material is then blended with other ingredients prior to manufacturing the final dosage form.

In some embodiments, a high shear wet granulation (HSWG) process involves pre-blending the intragranular ingredients, adding water with mixing, wet massing, fluidized bed drying, co-milling, final lubrication, and encapsulation.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However, for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

6.3 Methods of Use

In one embodiment, provided herein is a method of treating multiple myeloma, which comprises administering to a patient a pharmaceutical composition provided herein. In one embodiment, provided herein is a pharmaceutical composition provided herein for use in a method of treating multiple myeloma, wherein the method comprises administering said pharmaceutical composition to a patient.

In one embodiment, provided herein is a method of preventing multiple myeloma, which comprises administering to a patient a pharmaceutical composition provided herein. In one embodiment, provided herein is a pharmaceutical composition provided herein for use in a method of preventing multiple myeloma, wherein the method comprises said compound to a patient.

In one embodiment, provided herein is a method of managing multiple myeloma, which comprises administering to a patient a pharmaceutical composition provided herein. In one embodiment, provided herein is a pharmaceutical composition provided herein for use in a method of managing multiple myeloma, wherein the method comprises administering said compound to a patient.

In one embodiment, also provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, comprising administering an effective amount of a pharmaceutical composition provided herein to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a pharmaceutical composition provided herein to patient having multiple myeloma. In another embodiment, provided herein are methods for achieving an increase in overall survival, progression-free survival, event-free survival, time to progression, or disease-free survival in a patient, comprising administering an effective amount of a pharmaceutical composition provided herein to patient having multiple myeloma. In another embodiment, provided herein are methods for achieving an increase in overall survival in a patient, comprising administering an effective amount of a pharmaceutical composition provided herein to patient having multiple myeloma. In another embodiment, provided herein are methods for achieving an increase in progression-free survival in a patient, comprising administering an effective amount of a pharmaceutical composition provided herein to patient having multiple myeloma. In another embodiment, provided herein are methods for achieving an increase in event-free survival in a patient, comprising administering an effective amount of a pharmaceutical composition provided herein to patient having multiple myeloma. In another embodiment, provided herein are methods for achieving an increase in time to progression in a patient, comprising administering an effective amount of a pharmaceutical composition provided herein to patient having multiple myeloma. In another embodiment, provided herein are methods for achieving an increase in disease-free survival in a patient, comprising administering an effective amount of a pharmaceutical composition provided herein to patient having multiple myeloma.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a pharmaceutical composition provided herein. In another embodiment, methods provided herein encompass treating, preventing or managing multiple myeloma characterized by genetic abnormalities, such as Cyclin D translocations (for example, t(11;14)(q13;q32); t(6;14)(p21;32); t(12;14)(p13;q32); or t(6;20);); MMSET translocations (for example, t(4;14)(p16;q32)); MAF translocations (for example, t(14;16)(q32;q32); t(20;22); t(16; 22)(q11;q13); or t(14;20)(q32;q11)); or other chromosome factors (for example, deletion of 17p13, or chromosome 13; del(17/17p), nonhyperdiploidy, and gain(1q)), by administering a therapeutically effective amount of a pharmaceutical composition provided herein.

In some embodiments, the methods comprise administering a therapeutically effective amount of a pharmaceutical composition provided herein as induction therapy. In some embodiments, the methods comprise administering a therapeutically effective amount of a pharmaceutical composition provided herein as consolidation therapy. In some embodiments, the methods comprise administering a therapeutically effective amount of a pharmaceutical composition provided herein as maintenance therapy.

In one particular embodiment of the methods described herein, the multiple myeloma is plasma cell leukemia.

In one embodiment of the methods described herein, the multiple myeloma is high risk multiple myeloma. In some such embodiments, the high risk multiple myeloma is relapsed or refractory. In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p) and t(14;16)(q32;q32). In some such embodiments, the high risk multiple myeloma is relapsed or refractory to one, two or three previous treatments.

In one embodiment, the multiple myeloma is characterized by a p53 mutation. In one embodiment, the p53 mutation is a Q331 mutation. In one embodiment, the p53 mutation is an R273H mutation. In one embodiment, the p53 mutation is a K132 mutation. In one embodiment, the p53 mutation is a K132N mutation. In one embodiment, the p53 mutation is an R337 mutation. In one embodiment, the p53 mutation is an R337L mutation. In one embodiment, the p53 mutation is a W146 mutation. In one embodiment, the p53 mutation is an S261 mutation. In one embodiment, the p53 mutation is an S261T mutation. In one embodiment, the p53 mutation is an E286 mutation. In one embodiment, the p53 mutation is an E286K mutation. In one embodiment, the p53 mutation is an R175 mutation. In one embodiment, the p53 mutation is an R175H mutation. In one embodiment, the p53 mutation is an E258 mutation. In one embodiment, the p53 mutation is an E258K mutation. In one embodiment, the p53 mutation is an A161 mutation. In one embodiment, the p53 mutation is an A161T mutation.

In one embodiment, the multiple myeloma is characterized by homozygous deletion of p53. In one embodiment, the multiple myeloma is characterized by homozygous deletion of wild type p53.

In one embodiment, the multiple myeloma is characterized by wild type p53.

In one embodiment, the multiple myeloma is characterized by activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma is characterized by activation of C-MAF. In one embodiment, the multiple myeloma is characterized by activation of MAFB. In one embodiment, the multiple myeloma is characterized by activation of FGFR3 and MMset. In one embodiment, the multiple myeloma is characterized by activation of C-MAF, FGFR3, and MMset. In one embodiment, the multiple myeloma is characterized by activation of Cyclin D1. In one embodiment, the multiple myeloma is characterized by activation of MAFB and Cyclin D1. In one embodiment, the multiple myeloma is characterized by activation of Cyclin D.

In one embodiment, the multiple myeloma is characterized by one or more chromosomal translocations. In one embodiment, the chromosomal translocation is t(14;16). In one embodiment, the chromosomal translocation is t(14;20). In one embodiment, the chromosomal translocation is t(4; 14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14;16) and t(16;22). In one embodiment, the chromosomal translocations are t(14;20) and t(11;14).

In one embodiment, the multiple myeloma is characterized by a Q331 p53 mutation, by activation of C-MAF, and by a chromosomal translocation at t(14;16). In one embodiment, the multiple myeloma is characterized by homozygous deletion of p53, by activation of C-MAF, and by a chromosomal translocation at t(14;16). In one embodiment, the multiple myeloma is characterized by a K132N p53 mutation, by activation of MAFB, and by a chromosomal translocation at t(14;20). In one embodiment, the multiple myeloma is characterized by wild type p53, by activation of FGFR3 and MMset, and by a chromosomal translocation at t(4;14). In one embodiment, the multiple myeloma is characterized by wild type p53, by activation of C-MAF, and by a chromosomal translocation at t(14;16). In one embodiment, the multiple myeloma is characterized by homozygous deletion of p53, by activation of FGFR3, MMset, and C-MAF, and by chromosomal translocations at t(4;14) and t(14;16). In one embodiment, the multiple myeloma is characterized by homozygous deletion of p53, by activation of Cyclin D1, and by a chromosomal translocation at t(11; 14). In one embodiment, the multiple myeloma is characterized by an R337L p53 mutation, by activation of Cyclin D1, and by a chromosomal translocation at t(11;14). In one embodiment, the multiple myeloma is characterized by a W146 p53 mutation, by activation of FGFR3 and MMset, and by a chromosomal translocation at t(4;14). In one embodiment, the multiple myeloma is characterized by an S261T p53 mutation, by activation of MAFB, and by chromosomal translocations at t(6;20) and t(20;22). In one embodiment, the multiple myeloma is characterized by an E286K p53 mutation, by activation of FGFR3 and MMset, and by a chromosomal translocation at t(4;14). In one embodiment, the multiple myeloma is characterized by an R175H p53 mutation, by activation of FGFR3 and MMset, and by a chromosomal translocation at t(4;14). In one embodiment, the multiple myeloma is characterized by an E258K p53 mutation, by activation of C-MAF, and by chromosomal translocations at t(14;16) and t(16;22). In one embodiment, the multiple myeloma is characterized by wild type p53, by activation of MAFB and Cyclin D1, and by chromosomal translocations at t(14;20) and t(11;14). In one embodiment, the multiple myeloma is characterized by an A161T p53 mutation, by activation of Cyclin D, and by a chromosomal translocation at t(11;14).

In some embodiments of the methods described herein, the multiple myeloma is transplant eligible newly diagnosed multiple myeloma. In another embodiment, the multiple myeloma is transplant ineligible newly diagnosed multiple myeloma.

In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a pharmaceutical composition provided herein to a patient having relapsed/refractory multiple myeloma with impaired renal function.

In certain embodiments, provided herein are methods of treating, preventing, and/or managing multiple myeloma, including relapsed or refractory multiple myeloma in frail patients or a symptom thereof, comprising administering a therapeutically effective amount of a pharmaceutical composition provided herein to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, provided herein are methods of treating, preventing or managing multiple myeloma, comprising administering to a patient a therapeutically effective amount of a pharmaceutical composition provided herein wherein the multiple myeloma is fourth line relapsed/refractory multiple myeloma.

In certain embodiments, provided herein are methods of treating, preventing or managing multiple myeloma, comprising administering to a patient a therapeutically effective amount of a pharmaceutical composition provided herein as induction therapy, wherein the multiple myeloma is newly diagnosed, transplant-eligible multiple myeloma.

In certain embodiments, provided herein are methods of treating, preventing or managing multiple myeloma, comprising administering to a patient a therapeutically effective amount of a pharmaceutical composition provided herein as maintenance therapy after other therapy or transplant, wherein the multiple myeloma is newly diagnosed, transplant-eligible multiple myeloma prior to the other therapy or transplant.

In certain embodiments, provided herein are methods of treating, preventing or managing multiple myeloma, comprising administering to a patient a therapeutically effective amount of a pharmaceutical composition provided herein as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1.

In certain embodiments, provided herein are methods of treating, preventing or managing multiple myeloma, comprising administering to a patient a therapeutically effective amount of a pharmaceutical composition provided herein, wherein the multiple myeloma is high risk multiple myeloma, that is relapsed or refractory to one, two or three previous treatments.

In certain embodiments, provided herein are methods of treating, preventing or managing multiple myeloma, comprising administering to a patient a therapeutically effective amount of a pharmaceutical composition provided herein, wherein the multiple myeloma is newly diagnosed, transplant-ineligible multiple myeloma.

In certain embodiments, a therapeutically or prophylactically effective amount of the compound is from about from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1 for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day given either the height or weight of a subject or both (see, www.fda.gov/cder/cancer/animalframe.htm). For example, a dose of 1 mg/kg/day for a 65 kg human is approximately equal to 38 $mg/m^2$/day.

In certain embodiments, the patient to be treated with one of the methods provided herein has not been treated with multiple myeloma therapy prior to the administration of a pharmaceutical composition provided herein. In certain embodiments, the patient to be treated with one of the methods provided herein has been treated with multiple myeloma therapy prior to the administration of a pharmaceutical composition provided herein. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

Depending on the state of the disease to be treated and the subject's condition, a pharmaceutical composition provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A pharmaceutical composition provided herein may be formulated, alone or together, in suitable dosage unit with pharmaceutically acceptable excipients, carriers, adjuvants and vehicles, appropriate for each route of administration.

In one embodiment, a pharmaceutical composition provided herein is administered orally. In another embodiment, a pharmaceutical composition provided herein is administered parenterally. In yet another embodiment, a pharmaceutical composition provided herein is administered intravenously.

A pharmaceutical composition provided herein can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A pharmaceutical composition provided herein can be administered once daily (QD or qd), or divided into multiple daily doses such as twice daily (BID or bid), three times daily (TID or tid), and four times daily (QID or qid). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 7 days to 52 weeks. The term "intermittent" or "intermittently" as used herein is intended to mean stopping and starting at either regular or irregular intervals. For example, intermittent administration of a pharmaceutical composition provided herein, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a pharmaceutical composition provided herein is administered once a day. In another embodiment, a pharmaceutical composition provided herein is administered twice a day. In yet another embodiment, a pharmaceutical composition provided herein is administered three times a day. In still another embodiment, a pharmaceutical composition provided herein is administered four times a day.

In one embodiment, a therapeutically effective amount of a pharmaceutical composition provided herein is administered in a treatment cycle which includes an administration period of up to 20 days followed by a rest period. In one embodiment, a therapeutically effective amount of a pharmaceutical composition provided herein is administered in a treatment cycle which includes an administration period of up to 15 days followed by a rest period. In one embodiment, a therapeutically effective amount of a pharmaceutical composition provided herein is administered in a treatment cycle which includes an administration period of up to 10 days followed by a rest period. In one embodiment, a therapeutically effective amount of a pharmaceutical composition provided herein is administered in a treatment cycle which includes an administration period of up to 7 days followed by a rest period. In one embodiment, a therapeutically effective amount of a pharmaceutical composition provided herein is administered in a treatment cycle which includes an administration period of up to 5 days followed by a rest period. In one embodiment, a therapeutically effective amount of a pharmaceutical composition provided herein is administered in a treatment cycle which includes an administration period of up to 4 days followed by a rest period. In one embodiment, a therapeutically effective amount of a pharmaceutical composition provided herein is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of a pharmaceutical composition provided herein on days 1 to 5 of a 28 day cycle. In another embodiment, the treatment cycle includes an administration of a pharmaceutical composition provided herein on days 1 to 10 of a 28 day cycle. In one embodiment, the treatment cycle includes an administration of a therapeutically effective amount of a pharmaceutical composition provided herein on days 1 to 21 of a 28 day cycle. In another embodiment, the treatment cycle includes an administration of a therapeutically effective amount of a pharmaceutical composition provided herein on days 1 to 5 of a 7 day cycle. In another embodiment, the treatment cycle includes an administration of a therapeutically effective amount of a pharmaceutical composition provided herein on days 1 to 7 of a 7 day cycle. In one embodiment, the treatment cycle includes an administration of a therapeutically effective amount of a pharmaceutical composition provided herein on days 1 to 10 and days 15 to 24 of a 28 day cycle (herein referred to as 20/28 dosing cycle). In one embodiment, the treatment cycle includes an administration of a therapeutically effective amount of a pharmaceutical composition provided herein on days 1 to 3 and days 15 to 18 of a 28 day cycle. In one embodiment, the treatment cycle includes an administration of a therapeutically effective amount of a pharmaceutical composition provided herein on days 1 to 7 and days 15 to 21 of a 28 day cycle (herein referred to as 14/28 dosing cycle). In one embodiment, the treatment cycle includes an administration of a therapeutically effective amount of a pharmaceutical composition provided herein on days 1 to 5 and days 15 to 19 of a 28 day cycle (herein referred to as 10/28 dosing cycle). In one embodiment, the treatment cycle includes an administration of a therapeutically effective amount of a pharmaceutical composition provided herein on days 1 to 3 and days 15 to 17 of a 28 day cycle (herein referred to as 6/28 dosing cycle).

In one embodiment, the treatment cycle includes an administration of a therapeutically effective amount of a pharmaceutical composition provided herein on days 1 to 14 of a 21 day cycle. In another embodiment, the treatment cycle includes an administration of a pharmaceutical composition provided herein on days 1 to 4 and 8 to 11 of a 21 day cycle. In one embodiment, the treatment cycle includes an administration of a therapeutically effective amount of a pharmaceutical composition provided herein on days 1 to 5 and 8 to 12 of a 21 day cycle. In another embodiment, the treatment cycle includes an administration of a therapeutically effective amount of a pharmaceutical composition provided herein on days 1 to 5 and 11 to 15 of a 21 day cycle. In another embodiment, the treatment cycle includes an administration of a therapeutically effective amount of a pharmaceutical composition provided herein on days 1 to 5, 8 to 12 and 15 to 19 of a 21 day cycle. In another embodiment, the treatment cycle includes an administration of a therapeutically effective amount of a pharmaceutical composition provided herein on days 1 to 4, 8 to 11 and 15 to 18 of a 21 day cycle. In another embodiment, the treatment cycle includes an administration of a therapeutically effective amount of a pharmaceutical composition provided herein on days 1 to 4, 8 to 10 and 15 to 17 of a 21 day cycle. In another embodiment, the treatment cycle includes an administration of a therapeutically effective amount of a pharmaceutical composition provided herein on days 1 to 3, and 8 to 11 of a 21 day cycle. In another embodiment, the treatment cycle includes an administration of a therapeutically effective amount of a pharmaceutical composition provided herein on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of a pharmaceutical composition provided herein is administered for 1 to 13 cycles of 28 days (e.g., about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering a pharmaceutical composition provided herein at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering a pharmaceutical composition provided herein at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering a pharmaceutical composition provided herein once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering a pharmaceutical composition provided herein once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering a pharmaceutical composition provided herein once a day at a dosage amount of about 0.1 mg on days 1 to 10 and 15 to 24 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering a pharmaceutical composition provided herein twice a day at a dosage amount of about 0.2 mg on days 1 to 3 and 15 to 17 of a 28 day cycle. In one such embodiment, the pharmaceutical composition is administered on days 1 to 3 (morning and evening), day 14 (evening only), days 15 and 16 (morning and evening), and day 17 (morning only) of a 28 day cycle, for example in Cycle 1.

For clarity reasons, it is noted that, unless otherwise specified, the Compound 1 doses referred to herein refer to the amount of Compound 1 in its free base form. In case that for example a pharmaceutically acceptable salt of Compound 1 is used, the amounts given above will need to be adapted accordingly.

6.4 Combination Therapy with a Second Active Agent

A pharmaceutical composition provided herein can also be combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein and conventional therapy may provide a unique treatment regimen that is unexpectedly effective in certain patients. Without being limited by theory, it is believed that a pharmaceutical composition provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A pharmaceutical composition provided herein and other active ingredient can be administered to a patient prior to, during, or after the occurrence of the adverse effect associated with conventional therapy.

A pharmaceutical composition provided herein can also be combined or used in combination with other therapeutic agents useful in the treatment and/or prevention of multiple myeloma described herein.

In one embodiment, provided herein is a method of treating, preventing, or managing multiple myeloma, comprising administering to a patient a pharmaceutical composition provided herein in combination with one or more second active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a pharmaceutical composition provided herein can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein, as is quadruple therapy. In one embodiment, the second therapy is dexamethasone.

Administration of a pharmaceutical composition provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of a pharmaceutical composition provided herein is independent of the route of administration of a second therapy. In one embodiment, a pharmaceutical composition provided herein is administered orally. In another embodiment, a pharmaceutical composition provided herein is administered intravenously. Thus, in accordance with these embodiments, a pharmaceutical composition provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a pharmaceutical composition provided herein and a second therapy are administered by the same mode of administration, orally or by IV. In another embodiment, a pharmaceutical composition provided herein is administered by one mode of administration, e.g., by IV, whereas the second agent (an anti-multiple myeloma agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of multiple myeloma being treated or managed, the severity and stage of disease, and the amount of a pharmaceutical composition provided herein and any optional additional active agents concurrently administered to the patient.

One or more second active ingredients or agents can be used together with a pharmaceutical composition provided herein in the methods and compositions provided herein. Second active agents can be large molecules (e.g., proteins), small molecules (e.g., synthetic inorganic, organometallic, or organic molecules), or cell therapies (e.g., CAR cells).

Examples of second active agents that can be used in the methods and compositions described herein include one or more of melphalan, vincristine, cyclophosphamide, etoposide, doxorubicin, bendamustine, obinutuzmab, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336), a BCL2 inhibitor (for example, venetoclax or navitoclax), an MCL-1 inhibitor (for example, AZD5991, AMG176, MIK665, S64315, or S63845), an LSD-1 inhibitor (for example, ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile or a salt thereof), a corticosteroid (for example, prednisone), dexamethasone; an antibody (for example, a CS1 antibody, such as elotuzumab; a CD38 antibody, such as daratumumab or isatuximab; or a BCMA antibody or antibody-conjugate, such as GSK2857916 or BI 836909), a checkpoint inhibitor (as described herein), or CAR cells (as described herein).

In one embodiment, the second active agent used together with a pharmaceutical composition provided herein in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at an 8 mg dose on days 1 and 8 of a 21 day cycle. In some other embodiments, the dexamethasone is administered at an 8 mg dose on days 1, 4, 8 and 11 of a 21 day cycle. In some embodiments, the dexamethasone is administered at an 8 mg dose on days 1, 8, and 15 of a 28 day cycle. In some other embodiments, the dexamethasone is administered at an 8 mg dose on days 1, 4, 8, 11, 15 and 18 of a 28 day cycle. In some embodiments, the dexamethasone is administered at an 8 mg dose on days 1, 8, 15, and 22 of a 28 day cycle. In one such embodiment, the dexamethasone is administered at an 8 mg dose on days 1, 10, 15, and 22 of Cycle 1. In some embodiments, the dexamethasone is administered at an 8 mg dose on days 1, 3, 15, and 17 of a 28 day cycle. In one such embodiment, the dexamethasone is administered at an 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15, and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15, and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the second active agent used together with a pharmaceutical composition provided herein in the methods and compositions described herein is bortezomib. In yet another embodiment, the second active agent used together with a pharmaceutical composition provided herein in the methods and compositions described herein is daratumumab. In some such embodiments, the methods additionally comprise administration of dexamethasone. In some embodiments, the methods comprise administration of a pharmaceutical composition provided herein with a proteasome inhibitor as described herein, a CD38 inhibitor as described herein and a corticosteroid as described herein.

In another embodiment, the second active agent used together with a pharmaceutical composition provided herein in the methods and compositions described herein is panobinostat. In some such embodiments, the methods additionally comprise administration of dexamethasone.

In another embodiment, the second active agent used together with a pharmaceutical composition provided herein in the methods and compositions described herein is ACY241. In some such embodiments, the methods additionally comprise administration of dexamethasone.

In another embodiment, the second active agent used together with a pharmaceutical composition provided herein in the methods and compositions described herein is vincristine. In some such embodiments, the methods additionally comprise administration of dexamethasone.

In another embodiment, the second active agent used together with a pharmaceutical composition provided herein in the methods and compositions described herein is cyclophosphamide. In some such embodiments, the methods additionally comprise administration of dexamethasone.

In another embodiment, the second active agent used together with a pharmaceutical composition provided herein in the methods and compositions described herein is etoposide. In some such embodiments, the methods additionally comprise administration of dexamethasone.

In another embodiment, the second active agent used together with a pharmaceutical composition provided herein in the methods and compositions described herein is doxorubicin. In some such embodiments, the methods additionally comprise administration of dexamethasone.

In another embodiment, the second active agent used together with a pharmaceutical composition provided herein in the methods and compositions described herein is venetoclax. In some such embodiments, the methods additionally comprise administration of dexamethasone.

In another embodiment, the second active agent used together with a pharmaceutical composition provided herein in the methods and compositions described herein is AMG176. In some such embodiments, the methods additionally comprise administration of dexamethasone.

In another embodiment, the second active agent used together with a pharmaceutical composition provided herein in the methods and compositions described herein is MIK665. In some such embodiments, the methods additionally comprise administration of dexamethasone.

In another embodiment, the second active agent used together with a pharmaceutical composition provided herein in the methods and compositions described herein is GSK525762A. In some such embodiments, the methods additionally comprise administration of dexamethasone.

In another embodiment, the second active agent used together with a pharmaceutical composition provided herein in the methods and compositions described herein is OTX015. In some such embodiments, the methods additionally comprise administration of dexamethasone.

In another embodiment, the second active agent used together with a pharmaceutical composition provided herein in the methods and compositions described herein is 4-[2-(cyclopropylmethoxy)-5-(methanesulfonyl)phenyl]-2-methylisoquinolin-1(2H)-one. In some such embodiments, the methods additionally comprise administration of dexamethasone.

In another embodiment, the second active agent used together with a pharmaceutical composition provided herein in the methods and compositions described herein is 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile, or a salt thereof (for example a besylate salt). In some such embodiments, the methods additionally comprise administration of dexamethasone.

In certain embodiments, a pharmaceutical composition provided herein is administered in combination with checkpoint inhibitors. In one embodiment, one checkpoint inhibitor is used in combination with a pharmaceutical composition provided herein in connection with the methods provided herein. In another embodiment, two checkpoint inhibitors are used in combination with a pharmaceutical composition provided herein in connection with the methods provided herein. In yet another embodiment, three or more checkpoint inhibitors are used in combination with a pharmaceutical composition provided herein in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer,* 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.,* 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.,* 2012, 3834).

In one embodiment, the checkpoint inhibitors is a TIM3 (T-cell immunoglobulin domain and mucin domain 3) inhibitor (Fourcade et al., *J. Exp. Med.,* 2010, 207, 2175-86; Sakuishi et al., *J. Exp. Med.,* 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, a pharmaceutical composition provided herein can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMIB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 1 05(11):4247-4254 (2005).

In certain embodiments, a pharmaceutical composition provided herein is administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

7. EXAMPLES

Certain embodiments of the invention are illustrated by the following non-limiting examples.

Development of Compound 1 HBr Formulation

7.1 Drug-Excipient Compatibility Study

A binary drug-excipient compatibility study was conducted to identify suitable excipients for capsule formulation. The list of excipients from various functional classes that were evaluated are listed in the following table. Considering the low dose formulation where diluent constitutes majority of the composition, API to diluent ratio was 1:400; for other excipients, the ration was 1:50.

TABLE 1

List of Samples Evaluated for Compatibility with the Drug Substance

| Function | Excipient | Grade | Ratio |
|---|---|---|---|
| API | Compound 1 HBr | NA | 1 |
| Diluent | Microcrystalline cellulose | Avicel 102 | 1:400 |
| | Spray dried lactose monohydrate | Fast Flo 316 | 1:400 |
| | Mannitol | Pearlitol SD100 | 1:400 |
| | Partially pregelatinized starch | Lycatab C (Starch 1500) | 1:400 |
| Beads | Sugar beads (25/30) mesh | Suglets | 1:400 |
| Disintegrant | Croscarmellose sodium | Ac-di-Sol SD-711 | 1:50 |
| | Crospovidone/polyvinylpolypyrrolidone | Kollidon CL | 1:50 |
| | Sodium starch glycolate | Explotab type A | 1:50 |
| | Sodium starch glycolate (low pH grade) | Explotab type B | 1:50 |
| Binder/Crystallization Stabilizer | HPMC E5 | Hypromellose E5 | 1:50 |
| | PVP K90 | Plasdone K90 | 1:50 |
| | HPC EXF | Klucel EXF | 1:50 |
| Glidant | Precipitated silicon dioxide | Syloid 244FP | 1:50 |
| | Fumed silicon dioxide | Cabosil M5P | 1:50 |
| Lubricant | Sodium stearyl fumarate | PRUV | 1:50 |
| | Stearic acid | Kolliwax | 1:50 |
| | Magnesium stearate | Hyqual | 1:50 |

Drug substance and excipients were dispensed at predetermined ratios, mixed using a vortex mixer for 30 seconds, and then dispensed into required number of vials for stability study. These vials (open dish condition) were exposed to 50° C./0% RH and 50° C./75% RH conditions for 2 and 4 weeks respectively. The control samples were stored in a refrigerator at 5° C. Selective samples were tested for chemical degradants and loss of chiral purity (conversion of S-isomer to R-isomer) after 2-weeks. Samples that showed >3% chemical degradation were excluded from the testing after 4-weeks.

Figure 1A:
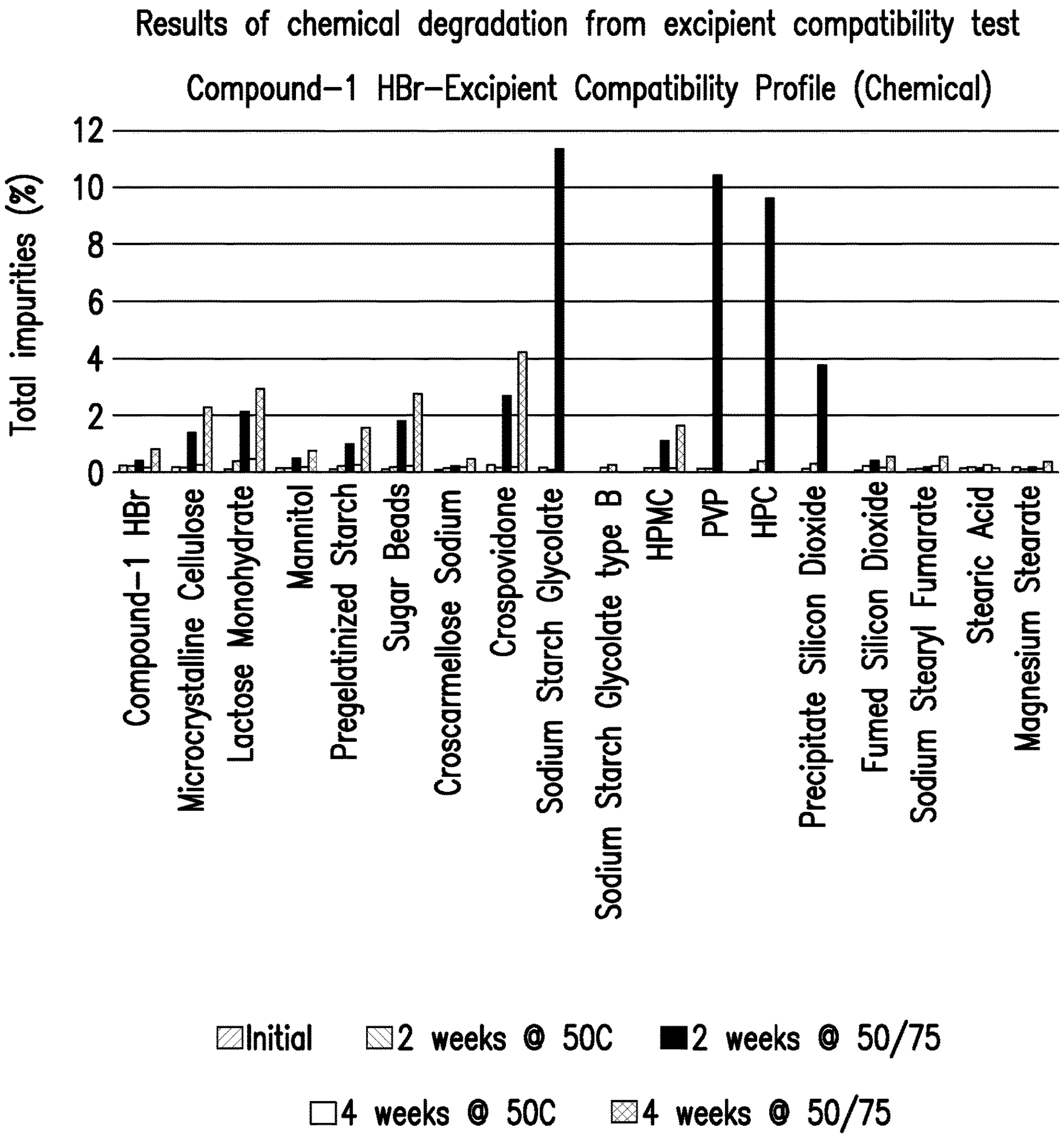
FIG. 1A and FIG. 1B show the total chemical impurities and chiral impurity levels from the excipient compatibility test, respectively.
Figure 1B:
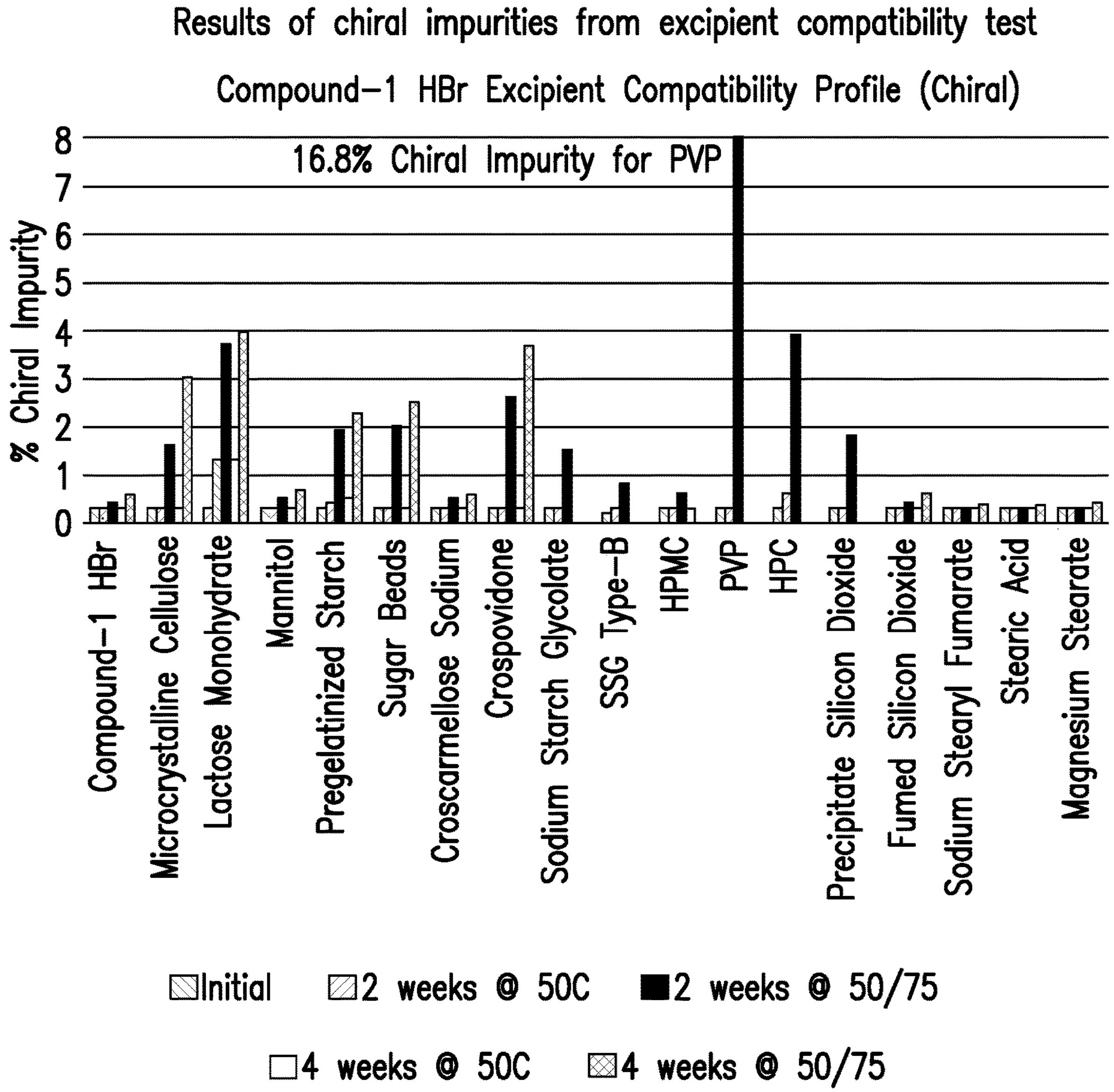

The following are the major degradation pathways that could be shelf-life limiting: (1) hydrolysis; (2) oxidation; and (3) loss of chiral purity. The total chemical impurities and chiral impurity levels of the samples after stressing for 2-weeks and 4-weeks are compared with the control samples which are shown in FIG. 1A and FIG. 1B, respectively.

Compound 1 HBr drug substance: The control sample showed 0.2% chemical impurities and 0.3% chiral impurity. Chemical impurity level increased to 0.35% after 2-weeks and 0.77% after 4-weeks exposure at 50° C./75% RH condition. Chiral impurity only increased to 0.4% after 4 weeks at this condition. At dry condition (50° C.), no significant change in either chemical impurities or chiral impurity was observed.

Diluents: Microcrystalline cellulose, mannitol, partially pregelatinized starch, and lactose monohydrate were evaluated as diluents or carriers. Mannitol was the most compatible based on the chemical and chiral impurity levels; the degradation profiles were similar to that of the drug substance itself. For rest of the three, starch was more compatible than MCC followed by lactose. In dry condition, starch showed slightly better compatibility than MCC and at 50° C./75% RH, starch was better than MCC. Out of the four diluents, lactose showed the most degradation both for chemical and chiral and both at 50° C. and 50° C./75% RH conditions. Overall, the diluents were rank ordered from most to least compatible as follows: mannitol> starch> MCC>lactose.

Disintegrants: Croscarmellose sodium (2- and 4-weeks data) and low pH sodium starch glycolate (2 weeks data) exhibited the best compatibility; the chemical and chiral impurities levels were similar to or better than the drug substance itself. Sodium starch glycolate type A exhibited the least chemical compatibility (6% impurities) after 2 weeks at 50° C./75% RH and excluded from further evaluation. Crospovidone showed the second highest level of chemical degradation and the highest chiral impurity. In dry condition, all four disintegrates showed similar stability as the neat drug substance. Overall, the disintegrants were ranked as follows: croscarmellose sodium~sodium starch glycolate type B>crospovidone>>sodium starch glycolate type A.

Binder: Among the polymers evaluated as binder and crystallization stabilizer, PVP K90 and HPC EXF caused significant decrease in chiral purity as well as significant increase in total relative impurities, only HPMC E5 was demonstrated to be compatible.

Glidants/anti-adherent: The precipitated silicon dioxide was shown to catalyze chemical degradation and also led to the loss of chiral purity. However, fumed silicon dioxide was found to have good compatibility.

Lubricant: All three lubricants evaluated were shown to have excellent compatibility with no noticeable increase in total relative impurity and chiral impurity. In particular, stearic acid was shown to have the least amount of total Related Impurities (chemical degradants) compared to the other two lubricants.

Among the evaluated excipients for drug-excipient compatibility studies, 9 were short-listed for formulation and process design considerations based on the impact on chemical and chiral degradation risks to the drug substance. In summary, microcrystalline cellulose, mannitol, pregelatinized starch, croscarmellose sodium, stearic acid, HPMC E5, sodium starch glycolate type B, fumed silicon dioxide, and sodium stearyl fumarate were selected for further evaluation in blends.

7.2 Prototype Formulation Development by RC Process

The prototype batches as listed in the following table were manufactured using RC process. The batch size was 500 g. The blends were compacted at the predicted roll force (4-4.5 kN) to achieve SF of ~0.75, 1 rpm roll speed and 2 mm roll gap. Capsules were exposed to accelerated open dish conditions (50° C./0% RH and 50° C./75% RH) and evaluated for chemical and chiral stability after 2 and 4 weeks. In this study, the HSWG formulation for the free base was used as the base line.

TABLE 2

Prototype batch composition manufactured to assess Chemical and Chiral Stability using RC as a Potential Manufacturing Platform

| Ingredient | PD02-247A | PD02-247B | PD02-247C | PD02-247E | PD02-247F |
|---|---|---|---|---|---|
| | | | % w/w | | |
| Compound 1 HBr* | 0.15 | 0.15 | 0.15 | 0.15 | 0.15 |
| Partially pregelatinized starch (Starch 1500) | 0.0 | 20.0 | 20.0 | 20.0 | 0.0 |
| Microcrystalline cellulose (Avicel PH 102) | 0.0 | 0.0 | 0.0 | 0.0 | 33.0 |
| Mannitol (Pearlitol SD100) | 97.85 | 77.85 | 76.85 | 77.85 | 64.85 |
| Silicon dioxide (Cab-O-Sil M5P) | 0.0 | 0.0 | 1.0 | 0.0 | 0.0 |
| Sodium stearyl fumarate (PRUV) | 2.0 | 2.0 | 2.0 | 0.0 | 2.0 |
| Stearic acid (Kolliwax) | 0.0 | 0.0 | 0.0 | 2.0 | 0.0 |
| Total (%) | 100.0 | 100.0 | 100.0 | 100.0 | 100.0 |

*based on theoretical potency of 0.8752

Figure 2A:
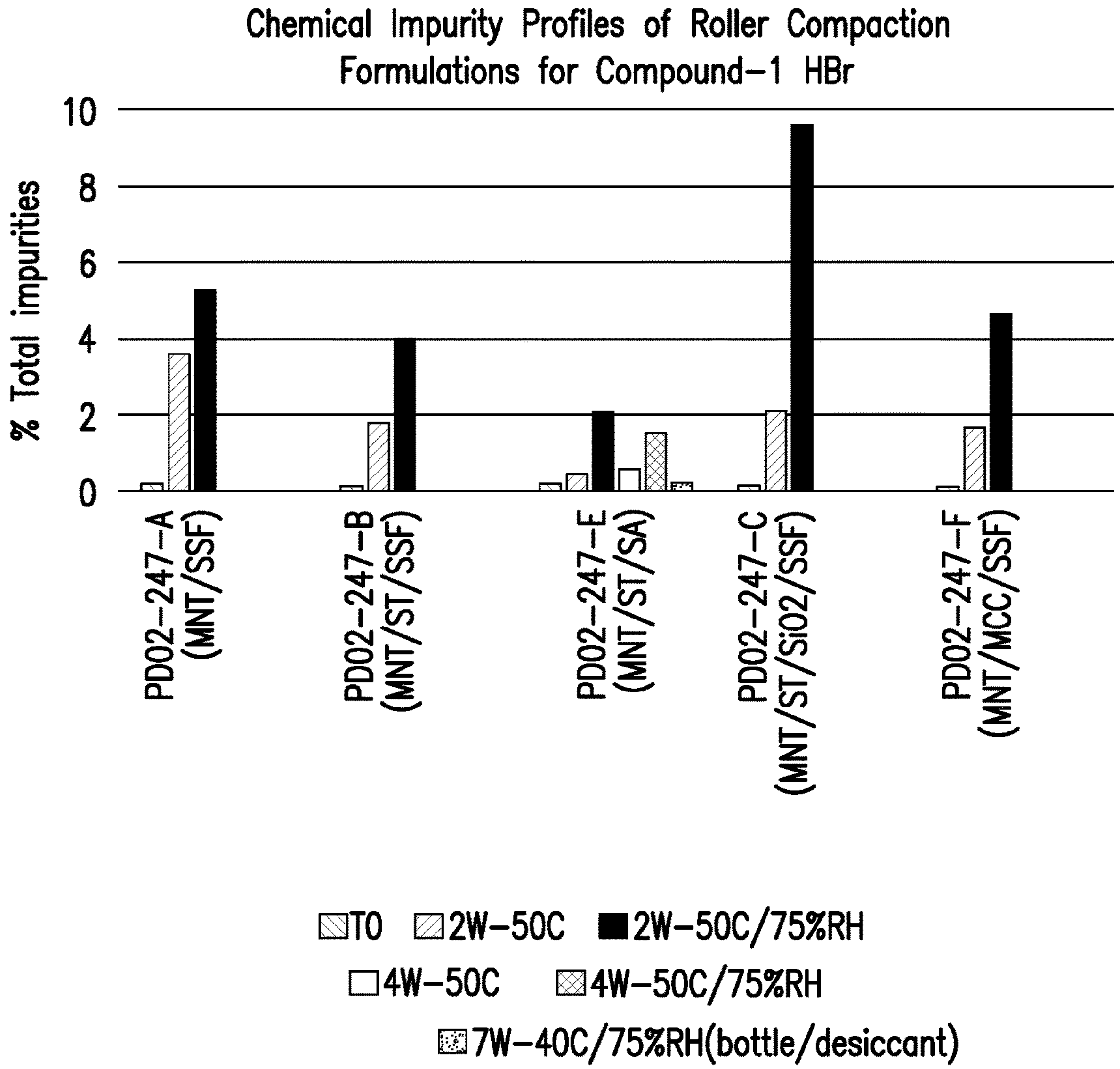
FIG. 2A and FIG. 2B show the total chemical impurities and chiral impurity levels for prototype formulations prepared by RC process, respectively.
Figure 2B:
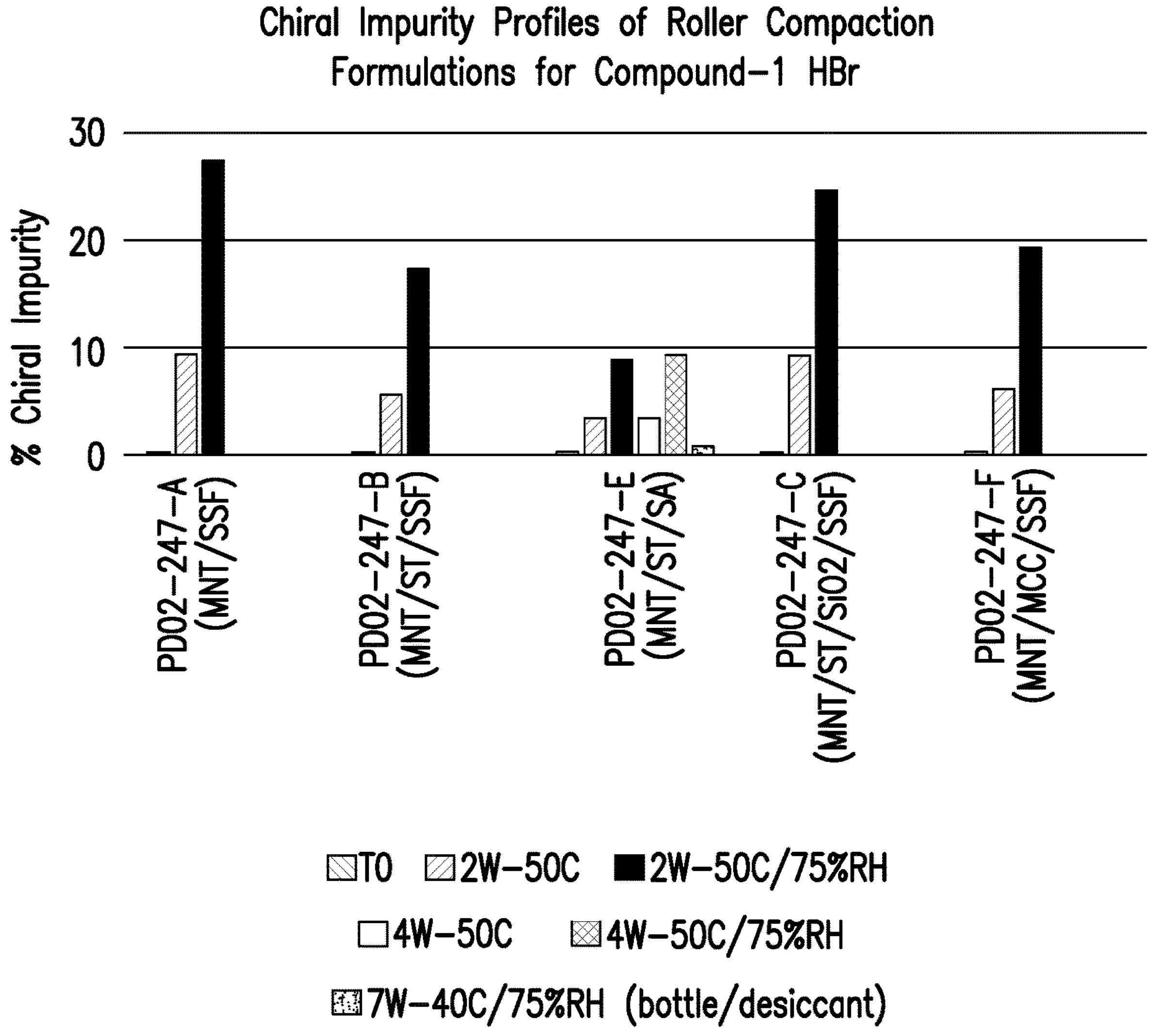

Chemical stability results are summarized in FIG. 2A. Formulation PD02-247B did not exhibit the best chemical stability. However, the presence of starch in this formulation improved the stability when compared to the formulation PD02-247A and the MCC containing formulation PD02-247F. Although, colloidal silicon dioxide showed excellent compatibility in the binary study, Formulation PD02-247C which contains silicon dioxide exhibited the worst chemical stability. Formulation PD02-247E with stearic acid as the lubricant showed significantly better chemical stability profile amongst all the evaluated prototype formulations. As shown in FIG. 2B, the chiral stability profiles of the formulations followed the similar trend. Formulation PD02-247E with mannitol, starch and stearic acid was selected for further evaluation.

7.3 Selection of Lead Prototype Formulation for RC Process

The impacts of adding disintegrant and binder on stability of formulations at 0.15% DL (0.1 mg capsules) were evaluated which could have implications to granulation robustness, stability and dissolution. As shown in the following table, Batches PD02-292A2, PD02-292B and PD02-292C were manufactured with no disintegrant, with sodium croscarmellose (CCS) and with low pH sodium starch glycolate (low pH SSG), respectively. In addition, to evaluate the impact of binder, a formulation PD02-332 was manufactured with HPMC E5 and CCS. To evaluate the impacts of disintegrant on dissolution of capsules, a formulation without disintegrant, a formulation with CCS and a third formulation with CCS and HPMC E5 were manufactured at 1.5% DL (2 mg capsules). All these batches were manufactured using a roller compaction process. Capsules were exposed to 50° C./0% RH and 50° C./75% RH open dish conditions for both stability and dissolution studies.

TABLE 3

| Prototype batches manufactured to assess stability | | | | |
|---|---|---|---|---|
| | Batches | | | |
| Ingredients | PD02-292A2 | PD02-292B | PD02-292C | PD02-332 |
| | w/w % | | | |
| Compound 1 HBr | 0.15 | 0.15 | 0.15 | 0.15 |
| Starch 1500 | 20 | 20 | 20 | 20 |
| Mannitol (Pearlitol SD 100) | 77.85 | 72.85 | 72.85 | 67.85 |
| Croscarmellose sodium (Ac-di-Sol SD-711) | 0 | 5 | 0 | 5 |
| Low pH Sodium starch glycolate (Explotab type-B) | 0 | 0 | 5 | 0 |
| HPMC E5 | 0 | 0 | 0 | 5 |
| Stearic acid | 1 | 1 | 1 | 1 |
| Subtotal | 99 | 99 | 99 | 99 |
| Extragranular stearic acid | 1 | 1 | 1 | 1 |
| Total | 100 | 100 | 100 | 100 |

Hydrolytic and chiral degradations are summarized in FIG. 3A, FIG. 3B, and FIG. 3C. Comparing formulation PD02-292A2 without any disintegrant and formulation PD02-292B with croscarmellose sodium, similar degradations were observed at four weeks' time point. Comparing formulation PD02-292B with croscarmellose sodium (CCS) and formulation PD02-292C with sodium starch glycolate-type B (SSG), formulation with SSG-type B demonstrated significantly better stability profiles. The seven weeks at 50° C. and 50° C./75% RH for PD02-292C was even comparable to four weeks at 50° C. and 50° C./75% RH for PD02-292B. Lastly, comparing formulation PD02-292B with CCS and formulation PD02-332 which contains both CCS and HPMC, the presence of HPMC has demonstrated similar chemical and chiral stability for two weeks at 50° C. and 50° C./75% RH.

The slurry pH of selected prototype formulations was measured to assess the microenvironmental pH and ascertain the disproportionation propensity of the HBr salt (pKa 6.62, $pH_{max}$ 4.62) in the formulation. As shown in the following table, the presence of low pH SSG in the formulation (PD02-292C) resulted in the lowest slurry pH, 4.65, which approximates the $pH_{max}$ of the salt. Whereas, slurry pH of the formulations without a disintegrant, with CCS or CCS and HPMC E5 were 5.61 or higher.

TABLE 4

| Slurry pH of prototype formulations evaluated using RC process | |
|---|---|
| Batch Number | Slurry pH |
| PD02-292A1-Final Blend (no disintegrant) | 5.61 |
| PD02-292B-Final Blend (CCS) | 5.64 |
| PD02-292C-Final Blend (SSG-B) | 4.65 |
| PD02-332-Final Blend (CCS and HPMC) | 5.73 |

Based on the hydrolytic and chiral stability and the slurry pH, the formulation containing mannitol, starch, low pH SSG, HPMC E5 and stearic acid was selected as the lead prototype formulation for the roller compaction process.

7.4 Manufacturability Assessment of RC Process

The lead prototype formulation PD02-366, as shown in the following table, was manufactured using RC process to evaluate manufacturability of the formulation. The theoretical batch size was 5 kg. All the intragranular ingredients were mixed in a blender, deagglomerated using a comil, and passed through the roller compactor and mill to produce the granules. For the batch PD02-366, approximately, half of the milled granules were then mixed with extragranular lubricant to obtain the final blend which was subsequently encapsulated into Vcaps Plus HPMC capsule shells. For the batch PD02-366A, the remaining half was mixed with extragranular mannitol and lubricant to obtain the final blend which was subsequently encapsulated into Vcaps Plus HPMC capsule shells. Stratified capsule samples were collected for CU testing.

TABLE-5

| Prototype batches Manufactured to assess RC as a Potential Manufacturing Platform | | |
|---|---|---|
| | Batch Number | |
| | PD02-366 | PD02-366A |
| Ribbon solid fraction | 0.67 | |
| Ingredient | % w/w | |
| Compound 1 HBr | 0.163 | 0.138 |
| Mannitol (Pearlitol 100 SD) | 65.84 | 55.77 |
| Partially Pregelatinized starch (Starch 1500) | 20 | 16.94 |
| Sodium Starch Glycolate type B | 5 | 4.24 |
| HPMC E5 | 5 | 4.24 |
| Stearic acid | 2 | 1.69 |
| Extragranular | | |
| Mannitol SD100 | 0 | 15.00 |
| Stearic acid | 2.00 | 2.00 |
| Total | 100.00 | 100.00 |

Flowability of final blends of PD02-366 and PD02-366A with 15% extragranular Mannitol SD100 was tested. FFc values of 4.8 and 5.9 was found for PD02-366 and PD02-366A, respectively, demonstrating that extra granular mannitol improved the final blend flow. PD02-366 has a slurry pH of 4.54. Capsule weight control was tighter for PD02-366A with % RSD in the range of 1.17%-1.68%, as compared to PD02-366 which was in the range of 1.65%-2.84%.

The extra-granulation formulation PD02-366A yielded low AV and tighter % RSD, potentially due to improved flowability with the incorporation of extra-granular (15% w/w) mannitol 100SD. The mean label claim (% LC), % RSD and acceptance values (AV) are indicated in the following table.

TABLE 6

| Mean Label Claim (% LC) and Acceptance Value (AV) of Prototype RC Batches | | | | | |
|---|---|---|---|---|---|
| Batch Number | % Label Claim | Weight corrected % LC | Acceptance Value | % RSD | Weight corrected % RSD |
| PD02-366 | 100.7 | 100.4 | 10.8 | 4.5 | 2.2 |
| PD02-366A | 101.8 | 103.3 | 5.1 | 2.0 | 1.6 |

In conclusion, roller compaction process was found to be a feasable manufacturing process to meet critical quality attributes of the drug product. PD02-366A was selected as the lead prototype formulation for the roller compaction process. The drug loading could vary from 0.164% to 0.653% to obtain 0.1-1.6 mg strength capsules. The PD02-366A capsule batch was packaged as 7-count per 100 cc HDPE bottle and 2 g desiccant for ICH stability study.

7.5 Prototype Formulation Development by HSWG Process

The small-scale prototype batches as listed in the following table were manufactured using high shear wet granulation (HSWG) process. The batch size was 500 g. The manufacturing process consisted of the following: preblending of the intragranular ingredients in a granulator bowl, water addition with mixing, wet massing, fluidized bed drying, co-milling, final lubrication, and encapsulation. Chemical and chiral stability of these capsule batches were evaluated using open dish stability at the following storage conditions: 50° C./0% RH and 50° C./75% RH for two weeks and four weeks, respectively.

TABLE 7

| Small scale prototype batches Manufactured to assess HSWG as a Potential Manufacturing Platform | | | | |
|---|---|---|---|---|
| Ingredient | PD02-248A | PD02-248B | PD02-248C | PD02-248F |
| | w/w % | | | |
| Compound 1 HBr* | 0.15 | 0.15 | 0.15 | 0.15 |

TABLE 7-continued

| Small scale prototype batches Manufactured to assess HSWG as a Potential Manufacturing Platform | | | | |
|---|---|---|---|---|
| Ingredient | PD02-248A | PD02-248B | PD02-248C | PD02-248F |
| | w/w % | | | |
| MCC Avicel PH101 | 0.0 | 0.0 | 33.0 | 33.0 |
| Starch 1500 | 20.0 | 20.0 | 0.0 | 0.0 |
| Mannitol (Pearlitol 50C) | 77.85 | 72.85 | 59.85 | 54.85 |
| SSG, Explotab type B | 0.0 | 0.0 | 0.0 | 5.0 |
| HPMC E5 | 0.0 | 5.0 | 5.0 | 5.0 |
| | Extragranular | | | |
| Sodium stearyl fumarate | 2.0 | 2.0 | 2.0 | 2.0 |
| Total | 100 | 100 | 100 | 100 |

*based on theoretical potency of 0.8752

Based on the small-scale prototype stability studies (FIG. 4A and FIG. 4B), the following observations were made and are summarized below: Comparing PD02-248A and 248B (with HPMC), formulation with HPMC as a binder improved the stability substantially. Comparing PD02-248B (with starch) and PD02-248C (with MCC), MCC as a diluent provided slightly better stability than formulation with starch. Comparing PD02-248C and PD02-248F (with SSG-type B), formulation with SSG-type B demonstrated the best overall chemical and chiral stability profile. From the initial prototype formulation screening, mannitol, starch, MCC, SSG-type B, HPMC, and SSF were selected for further evaluation.

7.6 Selection of Lead Prototype Formulation for HSWG Process

In this study, the effects of binder and disintegrant in the selected HSWG formulation were evaluated. The prototype batches as indicated in the following table were manufactured and evaluated for chemical and chiral stability, content uniformity, and dissolution. Batch size was 3 kg. Manufacturing steps comprise the following: bag blending of intragranular excipients for 2 minutes, pre-mixing in the granulator, granulation (water addition 100 g/min), fluidized bed drying, comilling, final blending/lubrication, and encapsulation.

TABLE 8

| Prototype batches manufactured to assess stability | | | | | | | |
|---|---|---|---|---|---|---|---|
| | Batch # | | | | | | |
| | PD02-316 | PD02-315 | PD02-314 | PD02-324 | PD02-323 | PD02-328 | PD02-329 |
| | w/w % | | | | | | |
| Compound 1 HBr | 0.152 | 0.152 | 0.152 | 1.37 | 1.37 | 1.37 | 1.37 |
| Mannitol 50C | 67.848 | 67.848 | 54.85 | 58.63 | 53.63 | 53.63 | 53.63 |
| Starch 1500 | 20 | 20 | 0 | 0 | 0 | 0 | 0 |
| MCC PH101 | 0 | 0 | 33 | 33 | 33 | 33 | 33 |
| HPMC E5 | 5 (dry) | 5 (dry) | 5(dry) | 5 (dry) | 5 (dry) | 5 (dry) | 5 (sol) |
| Croscarmellose sodium | 5 | 0 | 5 | 0 | 5 | 0 | 0 |
| SSG type B | 0 | 5 | 0 | 0 | 0 | 5 | 5 |
| Subtotal | 98 | 98 | 98 | 98 | 98 | 98 | 98 |
| Extragranular SSF | 2 | 2 | 2 | 2 | 2 | 2 | 2 |
| Total | 100 | 100 | 100 | 100 | 100 | 100 | 100 |

Hydrolytic and chiral degradations are summarized in FIG. 5A, FIG. 5B, and FIG. 5C. Formulation without any disintegrants showed much higher amount of degradation as can be seen in PD02-248A. Comparing PD02-248F (SSG-type B) and PD02-314 (CCS), SSG-type B again exhibited much better stability. Degradations at 11 days 50° C./75% RH was already higher for PD02-314 than that of PD02-248F at 14 days. Similar observation was seen for PD02-315 (SSG-type B) vs. PD02-316 (CCS), CCS led to higher degradation in the PD02-316 formulation. Again, MCC as a diluent (PD02-314) provided slightly better stability than formulation with starch (PD02-316).

To evaluate the effects of stearic acid versus SSF as a lubricant on stability of the selected prototype formulation, PD02-373 and PD02-373A were manufactured. The batch size was 500 g. The manufacturing process consisted of pre-blending of intragranular ingredients in the granulator bowl, followed mixing with addition of water to granulate, wet massing, fluidized bed drying, co-milling, lubrication and encapsulation. The compositions are shown in the following table.

TABLE 9

Prototype formulation manufactured to evaluate stearic acid on stability

| | Batch# | |
|---|---|---|
| Ingredients | PD02-373<br>Quantity (w/w %) | PD02-373A |
| Compound 1 HBr | 0.152 | 0.152 |
| Mannitol 50C | 55.85 | 55.85 |
| MCC PH101 | 30 | 30 |
| HPMC E5 | 5 | 5 |
| Low pH SSG | 5 | 5 |
| Stearic acid | 0 | 4 |
| Sodium stearyl fumarate | 4 | 0 |
| Total | 100% | 100% |

Stearic acid provided acceptable chemical and chiral stability based on the open dish stability data as shown in FIG. 6A. PD02-373A was also packaged as 7 counts with and without 2 g desiccant in 100 mL HDPE bottle for development ICH stability study. One- and three-month stability results are summarized in FIG. 6B. The formulation exhibited excellent stability across the stability conditions. The hydrolytic degradants were slightly higher at 40° C./75% RH than at 25° C./60% RH. Presence of the desiccant decreased the levels of hydrolytic degradants in both 25° C./60% RH and 40° C./75% RH conditions. The chiral impurity only slightly increased at 40° C./75% RH, and the impurity level was not impacted by the desiccant. In addition, stearic acid has been demonstrated from the RC process to increase formulation stability dramatically. Lastly, stearic acid minimizes the salt disproportionation risk as well. Therefore, stearic acid was chosen as the lubricant for further evaluation.

To determine the impacts of disintegrant and binder on dissolution of the formulations, 2 mg capsules (Batches PD02-323, 324, 328 and 329) were tested for in vitro dissolution using pH 4.5 citrate buffer as the medium. Dissolution test was performed at T=0, and after subjecting to 50° C./0% RH and 50° C./75% RH for 2 weeks. As shown in FIG. 7, Formulation PD02-324 (without disintegrant) showed the slowest release, roughly 80% at 45 mins. Formulation PD02-323 (CCS as the disintegrant) and PD02-328 (with SSG-Type B) showed very comparable dissolution profiles, demonstrating no significant differences between CCS and SSG-type B as a disintegrant. HPMC added as a binder solution (PD02-329) improved the drug release kinetics with around 94% release at 45 mins time point. The dissolution stability performance was not found to be significantly different at either T=0 or after storage at 50° C./75% RH for 2 weeks for all the batches.

Finally, the slurry pH of selected prototype formulations was measured to assess the microenvironmental pH and ascertain the disproportionation propensity of the HBr salt (pKa 6.62, $pH_{max}$ 4.62) in the formulation. As shown in the following table, the presence of low pH SSG in the formulation PD02-315 and PD02-328 resulted in lower slurry pH, 4.67 and 4.65 respectively. Whereas, slurry pH of the formulations without a disintegrant or with CCS were above 5.4.

TABLE 10

Slurry pH of prototype formulations evaluated with HSWG process

| Batch Number | Slurry pH |
|---|---|
| PD02-314 (MNT/ST/CCS) | 5.61 |
| PD02-315 (MNT/ST/SSG-B) | 4.67 |
| PD02-316 (MNT/ST/CCS) | 5.58 |
| PD02-323 (MNT/ST/CCS) | 5.66 |
| PD02-324 (MNT/MCC) | 5.44 |
| PD02-328 (MNT/MCC/SSG-B) | 4.65 |
| PD02-373A (MNT/MCC/SSG-B) | 4.52 |

Based on the hydrolytic and chiral stability, dissolution performance, and the slurry pH, the formulation containing mannitol, MCC, low pH SSG, HPMC and stearic acid was selected as the lead prototype formulation for HSWG process.

7.7 Manufacturability Assessment of HSWG Process

In addition to evaluating for stability and dissolution, the batches PD02-314, PD02-315, PD02-316, PD02-323, PD02-324, PD02-328 and PD02-329 were characterized for granule properties, and capsule weight variability. The capsules of batches PD02-314, 316, 328 and 329 were evaluated for assay.

Physical attributes of final blend such as particle size, bulk and tapped density, and in-process capsule weight % RSDs are shown in the following table. All the batches demonstrated good granule growth, $D_{50}$ of final blend varied between 120 and 250 μm. All the granulations demonstrated good flow (the Hausner Ratio would be less than 1.29) and likewise demonstrated good capsule weight control. Overall, the in-process capsule weight RSDs were less than 1.5%. The potency values of the selected batches (PD02-314, 316, 328, and 329) were acceptable and within the range of 96.9-103.0%.

TABLE 11

| Batch Number | Average Particle Size (μm) | D10 (μm) | D50 (μm) | D90 (μm) | BD (g/mL) | TD (g/mL) | In process weight % RSD |
|---|---|---|---|---|---|---|---|
| Particle size distribution, Density and In process weight variation (% RSD) of the Final Blend of Prototype HSWG Batches | | | | | | | |
| PD02-314 | 115.2 | ~80 | ~150 | ~280 | 0.47 | 0.60 | 0.96-1.46 |
| PD02-315 | 210.4 | ~80 | ~200 | ~600 | 0.61 | 0.77 | 0.99-1.10 |
| PD02-316 | 149.3 | ~50 | ~150 | ~450 | 0.56 | 0.72 | 1.18-1.46 |
| PD02-323 | 116.6 | ~80 | ~120 | ~280 | 0.54 | 0.66 | 0.47-0.61 |
| PD02-324 | 218.8 | ~100 | ~250 | ~550 | 0.59 | 0.70 | 0.38-0.47 |
| PD02-328 | 144.7 | ~80 | ~150 | ~350 | 0.56 | 0.67 | 0.43-0.67 |
| PD02-329 | 229.7 | ~80 | ~200 | ~650 | 0.57 | 0.71 | 0.43-0.58 |

In conclusion, based on acceptable open dish stability and fast dissolution release profiles, as well as acceptable assay data demonstrated above, HSWG process was found to be a feasable manufacturing process to meet critical quality attributes of the drug product.

7.8 Excipient Range Finding Study for Compound 1 HBr Formulation

To identify the quantitative composition of the Compound 1 HBr drug product for pivotal studies, the impacts of the levels of selected intra-granular excipients on manufacturability and quality attributes of capsules were determined. The study design comprised of a 23 full factorial DoE with 2 center point batches as shown in the following table. The three variables in the study were MCC, HPMC and SSG levels. The API level was fixed at 0.653% w/w to obtain the capsules strengths (0.4-1.6 mg) by varying the fill weight. The extra-granular stearic acid level was also fixed at 4% w/w in this study. The mannitol level was adjusted to add up to 100%.

TABLE 12

Study design of Excipient Range study

| MCC PH101 | HPMC E5 | SSG Type B | Mannitol 50C w/w % | Stearic Acid | Compound 1 HBr | Total | Batch Number |
|---|---|---|---|---|---|---|---|
| 10 | 3 | 3 | 79.347 | 4 | 0.653 | 100 | PD02-401 |
| 30 | 7 | 7 | 51.347 | 4 | 0.653 | 100 | PD02-402 |
| 20 | 5 | 5 | 65.347 | 4 | 0.653 | 100 | PD02-403 |
| 30 | 3 | 3 | 59.347 | 4 | 0.653 | 100 | PD02-404 |
| 10 | 7 | 3 | 75.347 | 4 | 0.653 | 100 | PD02-405 |
| 30 | 7 | 3 | 55.347 | 4 | 0.653 | 100 | PD02-406 |
| 10 | 3 | 7 | 75.347 | 4 | 0.653 | 100 | PD02-407 |
| 30 | 3 | 7 | 55.347 | 4 | 0.653 | 100 | PD02-408 |
| 10 | 7 | 7 | 71.347 | 4 | 0.653 | 100 | PD02-409 |
| 20 | 5 | 5 | 65.347 | 4 | 0.653 | 100 | PD02-410 |

Particle size distribution of the milled granules and bulk and tapped density of final blends are listed in the following table. In general, the batches containing higher proportion of HPMC as a binder have resulted in granules with larger average particle size; whereas, batches containing a combination of highest levels of MCC and lowest levels of HPMC have yielded the lowest average particle size (PD02-404 and PD02-408), respectively. The trend analysis showed that all the assessed variables exerted statistically significant impact on the physical properties of the granules with p-values of 0.00038 and 0.00302 for MCC and PMC, respectively. For the individual components, the level of MCC had a negative co-relation with the PSD and density where an increase in the levels of MCC was found to produce smaller granules with lower density. On the contrary, a positive co-relation on density and PSD was established with an increase in the level of HPMC. Similarly, the level of SSG studied demonstrated no substantial impact on the PSD, but on density with a P-value of 0.026.

TABLE 13

Particle Size Distribution of the Milled Granules and Density of the Final Blend

| Batch Number | Average Particle Size (μm) | D10 (μm) | D50 (μm) | D90 (μm) | BD (g/mL) | TD (g/mL) |
|---|---|---|---|---|---|---|
| PD02-401 | 178.5 | ~50 | ~200 | ~480 | 0.63 | 0.82 |
| PD02-402 | 157.1 | ~75 | ~190 | ~380 | 0.50 | 0.61 |
| PD02-403 | 160.9 | ~50 | ~200 | ~400 | 0.56 | 0.68 |
| PD02-404 | 109.4 | ~50 | ~120 | ~280 | 0.53 | 0.67 |
| PD02-405 | 213.6 | ~80 | ~250 | ~550 | 0.59 | 0.75 |
| PD02-406 | 168.6 | ~100 | ~220 | ~380 | 0.54 | 0.66 |
| PD02-407 | 109.3 | ~30 | ~100 | ~320 | 0.57 | 0.71 |

TABLE 13-continued

Particle Size Distribution of the Milled Granules and Density of the Final Blend

| Batch Number | Average Particle Size (μm) | D10 (μm) | D50 (μm) | D90 (μm) | BD (g/mL) | TD (g/mL) |
|---|---|---|---|---|---|---|
| PD02-408 | 109.9 | ~50 | ~140 | ~280 | 0.50 | 0.64 |
| PD02-409 | 234.4 | ~90 | ~250 | ~650 | 0.59 | 0.80 |
| PD02-410 | 159.4 | ~80 | ~180 | ~400 | 0.54 | 0.67 |

Sticking assessment of selected final blends demonstrated low propensity of the final blends to stick to tamping pin face during the encapsulation process.

The flow assessment on final blends from all the batches were conducted using a ring shear cell tester. The flow data indicate that all the batches fall under free-flowing regimen (ffc>10). The impact of powder flow on capsule weight variability was anticipated to be very low.

To ascertain the risk of salt disproportionation to free base in the formulation, the slurry pH on the final blends was measured. The slurry pH of all the blends ranged between 4.43 and 4.72. Theoretically, the extent of disproportionation could be ~1% at the microenvironmental pH range of 4.43-4.72 of the formulation (API pKa is 6.62).

To assess the homogeneity of the granulation, sieve cut assay was performed on milled granules of selected batches. Mean sieve cut assay of the tested batches varied between ~93-98% and RSDs were less than 15%. Based on the results, the tested granulations demonstrated acceptable homogeneity and CU risks were considered low.

Capsules were sampled at a regular interval during the encapsulation process for stratified content uniformity testing. All the batches exhibited good capsule weight control; the mean capsule weights of the batches were within 100±1% range and % RSD varied between 0.95% to 2.45%. All the batches exhibited acceptable content uniformity; mean CU values varied between 100±2% range, RSDs were 4.7% or less, and the AV values were less than 7 except for the batch PD02-405 (AV 11.4, RSD 4.7%). Individual capsule potencies of all the batches varied within 93-107%. The high CU variability of the batch PD02-405 could be attributed to its relatively higher weight variability (RSD 2.45%). After weight correction, the CU RSD value decreased from 4.7% to 3%. Optimization of the encapsulation parameters would further improve the capsule weight variability and thus the CU variability. A trend analysis demonstrated that the formulation variables (the levels of MCC, IPMC or SSG) did not significantly impact the weight corrected CU mean and RSD.

The dissolution performance of 1.6 mg capsules of the batches PD02-403, 406, 407 was evaluated at pH 4.5 (medium volume 500 mL) using USP Type-II dissolution apparatus at 50 rpm. The results (FIG. 8) show that the dissolution profiles of the three batches were similar, but PD02-407, the extreme batch with the lowest levels of MCC and IPMC and highest level of low pH SSG, demonstrated overall faster dissolution when compared with the other two batches.

A two-week open dish accelerated stability study at 50° C./0% RH and 50° C./75% RH was conducted to assess the impact of formulation variables on chemical and chiral stability. Three batches PD02-401, 402, 403 were evaluated. The data showed that the excipients level ranges evaluated in this study did not impact chemical or chiral stability of the formulations.

The excipient range DoE study demonstrated that the excipient levels evaluated in this study did not have any practical impacts on the product quality attributes such as CU, dissolution, and chemical and chiral stability. The center point batches were reproducibly manufactured and exhibited good stability and dissolution profile. Based on these observations, the center point formulation listed in the following table was proposed as the drug product for the human bioavailability (BA) study. The drug substance level could vary between 0.164 and 0.653% and the mannitol level will be adjusted accordingly. The potential capsule strengths, 0.1 mg to 1.6 mg, could be achieved by varying the capsule fill weights between 70-280 mg.

TABLE 14

Selection of Optimized Formulation Composition by HSWG Process Based on Excipient Range DoE Study for Human BA Study

| Ingredients | Quantity (w/w %) 0.164% DL | 0.653% DL |
|---|---|---|
| Compound 1 HBr | 0.164 | 0.653 |
| Mannitol 50C | 65.836 | 65.347 |
| MCC PH101 | 20 | 20 |
| HPMC E5 | 5 | 5 |
| Low pH SSG | 5 | 5 |
| Stearic acid | 4 | 4 |
| Total | 100% | 100% |
| Potential Dosage Strength (mg) | 0.1 to 0.4 | 0.4 to 1.6 |
| Fill weight (mg) | 70-280 | 70-280 |

7.9 Description of the Manufacturing Process

The intragranular ingredients API, mannitol, MCC, low pH SSG and HPMC were dispensed according to the Bill of Materials and loaded into a granulator bowl. The materials were dry mixed and granulated by adding a predetermined amount of water onto the powder bed in the granulator bowl. Wet granules were then conveyed to the fluid bed dryer and dried at a preset inlet air temperature. Inlet air volume was adjusted to maintain acceptable fluidized bed height. Dried granules were passed through a comil and the milled granules were further mixed with the pre-sieved stearic acid in a bin blender to obtain the final blend. The final blend was then filled into Vcaps Plus HPMC capsule shells at a predetermined fill weight. Capsules were finally dedusted and weight sorted.

Development of Compound 1 Free Base Formulation

The following Compound 1 free base formulations are previously described in U.S. application Ser. No. 16/737,721, the entirety of which is incorporated herein by reference. For convenience of reference, these formulations are referred hereafter in some embodiments as direct blend (DB) free base (FB) formulation with fumaric acid (FA).

TABLE 15

Free Base Formulation Compositions at 0.13%, 0.5% and 1% DL by Direct Blend Process

| Ingredients | 0.1 mg % w/w | 0.5 mg % w/w | 2 mg % w/w |
|---|---|---|---|
| Compound 1 | 0.133 | 0.5 | 1.0 |
| Silica Dimethyl Silylate (Aerosil R972) | 0.5 | | |
| Colloidal Silicon dioxide (Aerosil 200 Pharma) | | 1.0 | 2.0 |
| Mannitol (Pearlitol 200 SD) | 92.37 | 91.5 | 90.0 |
| Fumaric Acid Pharmaceutical grade (Powder) | 3.0 | 3.0 | 3.0 |
| Stearic Acid (Hystrene 5016 Veg) | 4.0 | 4.0 | 4.0 |
| Total Fill Weight | 100.00 | 100.00 | 100.00 |

The ICH stability study in conjunction with ASAP modeling demonstrated that both the 0.1 and 0.5 mg capsules of the free base formulations that were manufactured by the direct blending process would have acceptable stability when packaged in HDPE bottles with 2 g desiccant. Surprisingly, the 2 mg strength capsules with a higher DL as well as a higher Aerosil 200 level as an anti-adherent (or glidant) demonstrated the worst stability. This observation is counter intuitive and was appeared to be contributed by the Aerosil level in the formulation. In addition, the Aerosil grade used in the 0.1 mg capsules does not have global market acceptability.

Several studies were conducted to assess the impacts of the excipients or their levels on product quality (stability, dissolution, etc.) or manufacturability (e.g., sticking) and identity potential alternate excipients.

7.10 Evaluate Effects of Colloidal Silicon Dioxide

To evaluate the feasibility of removing Aerosil from the formulation, manufacturability of batches without Aerosil was assessed. In absence of Aerosil in the formulation, sticking of powder to the tamping pin was observed during the encapsulation process and the capsule assay was low. An alternate anti-adherent, Cab-O-Sil M5P did not improve the stability profile in an accelerated open dish study.

7.11 Evaluate Alternate Lubricants

To mitigate the potential sticking issue of the formulation without Aerosil, manufacturability of the formulations with more efficient lubricants such as SSF and magnesium stearate was assessed. As a surrogate, sticking assessment of formulations at the highest (2.56% w/w) projected drug loading with 4% SA, 4% SSF or 2% magnesium stearate was conducted using a compaction simulator. A higher level of SA (8% w/w) was also assessed. The compositions are indicated in the following table.

TABLE 16

Prototype Free Base Formulations with Fumaric Acid by Direct Blending Process - Evaluate Alternate Lubricants for Sticking Potential

| Ingredient | Batch Number<br>PD01-408-A % w/w | PD01-408-B % w/w | PD01-408-C % w/w | PD01-408-D % w/w |
|---|---|---|---|---|
| Compound 1 | 2.56 | 2.56 | 2.56 | 2.56 |
| Mannitol (Pearlitol 200 SD) | 90.44 | 86.44 | 90.44 | 92.44 |
| Fumaric acid pharmaceutical grade (powder) | 3.00 | 3.00 | 3.00 | 3.00 |
| Stearic acid (Hystrene 5016 Veg grade) | 4 | 8 | | |
| Sodium Stearyl Fumarate (PRUV) | | | 4 | |
| Magnesium Stearate (Hyqual Veg Grade) | | | | 2 |
| Total | 100.00 | 100.00 | 100.00 | 100.00 |

To assess sticking/filming potential, 10 compacts were made in succession using 9 mm flat face tooling at each compression force (100 N, 500 N, and 2500 N). The punch face was examined under a magnified lens and rank ordered for filming or sticking based on the following criteria: No haze appears virtually clean (rank 0); Light dust (minimal haze/powder, sharp reflections) (rank 1); Slight haze (slightly diffused reflections) (rank 2); Moderate haze (notably diffuse & reduced reflection) (rank 3); Heavy haze (effectively no light reflection) (rank 4); Slight waxy build-up (<1 $mm^2$) (rank 5); Moderate waxy build-up (1~2 $mm^2$) (rank 6); Extensive waxy build-up across multiple areas of debossing (rank 7); Debossing mostly covered by build-up (rank 8); No debossing visible (rank 9); Sticking affects tablet weight (rank 10). The ranking of sticking/filming observations are summarized in the following table. The results suggested that 4% SSF appeared to be only slightly better than the other three compositions.

TABLE 17

Summary of Sticking/Filming tendency after compacting 10 Successive Compacts using Prototype Formulations

| Force (Newtons) | PD01-408-A (4% SA) | PD01-408-B (8% SA) | PD01-408-C (4% SSF) | PD01-408-D (2% Mg Stearate) |
|---|---|---|---|---|
| 100 | 3 or 4 | 1 or 2 | 1 | 1 or 2 |
| 500 | 4 | 3 | 2 or 3 | 3 or 4 |
| 2500 | 6 | 6 | 5 | 5 or 6 |

In an open dish accelerated stability study, 0.1 mg strength capsules of prototype formulations with SSF (PD01-405A) or Mg Stearate (PD01-405B) manufactured by direct blending process exhibited better stability than the 0.1 mg direct blend capsules with Aerosil 972 (Cap-16). However, as stated earlier, the later formulation and the 0.5 mg direct blend capsules with Aerosil 200 have good stability in packaged configurations. The stability results suggest that with appropriate packaging configuration, any one of these three lubricants can be used in the direct blend formulations.

TABLE 18

Prototype Free Base Formulations by DB Process using Alternate Lubricants (PD01-405-A/B) at 0.14% DL

| Ingredient | Batch Number<br>PD01-405-A % w/w | PD01-405-B % w/w | Cap-16 % w/w |
|---|---|---|---|
| Compound 1 | 0.14 | 0.14 | 0.13 |
| Mannitol (Pearlitol 200 SD) | | | 91.87 |
| Mannitol (Pearlitol Flash)* | 92.86 | 94.86 | |
| Fumaric acid pharmaceutical grade (powder) | 3.00 | 3.00 | 3.00 |
| Silica dimethyl silylate (Aerosil ® R972) | | | 2.00 |
| Stearic acid (Hystrene 5016 Veg grade) | | | 3.00 |
| Sodium Stearyl Fumarate (PRUV) | 4.000 | | |
| Magnesium Stearate (Hyqual Veg Grade) | | 2.00 | |
| Total | 100.00 | 100.00 | 100.00 |

*Pearlitol Flash is a co-processed mixture of mannitol and pregelatinized starch (~80%-20% w/w).

7.12 Evaluate Level of Acidifier

Prototype free base formulations with varying levels (0-4% w/w) of FA were manufactured using a dry blending process. The formulation compositions are listed in the following table. The formulations contained Pearlitol flash as a diluent and no Aerosil. Slurry pH of the formulation ranged from 4.3 at 0% FA to 2.2 at 4% FA. In an accelerated open dish study, even at a high temperature and high humidity condition, the overall stability of formulations containing up to 3% FA were better than the direct blend free base formulation Cap-16. The compositions are shown in the following table.

TABLE 19

Prototype Free Base Formulation manufactured by Direct Blending - Evaluate FA Levels

| Ingredient | PD01-403-A % w/w | PD01-403-B % w/w | PD01-403-C % w/w | PD01-403-D % w/w | PD01-403-E % w/w | PD01-403-F % w/w |
|---|---|---|---|---|---|---|
| | Batch Number | | | | | |
| Compound 1 | 0.133 | 0.133 | 0.133 | 0.133 | 0.133 | 0.133 |
| Mannitol (Pearlitol Flash)* | 95.867 | 95.367 | 94.867 | 93.867 | 92.867 | 91.867 |
| Fumaric acid pharmaceutical grade (powder) | | 0.500 | 1.000 | 2.000 | 3.000 | 4.000 |
| Stearic Acid (Hystrene 5016 Veg) | 4.000 | 4.000 | 4.000 | 4.000 | 4.000 | 4.000 |
| Total | 100.00 | 100.00 | 100.00 | 100.00 | 100.00 | 100.00 |

*Pearlitol Flash is a co-processed mixture of mannitol and pregelatinized starch (~80%-20% w/w).

7.13 Evaluate Alternate Diluents

During the clinical batch manufacture, the DB process was not found to be robust due to variations in CU, especially for low drug loading (0.13% w/w) batch. Considering the inherent CU risk of direct blend process to manufacture low dose products, alternate manufacturing platform(s) like HSWG, FBG, RC were assessed to mitigate the potential CU risk.

Alternate diluents such as mannitol, MCC, starch, co-processed mannitol/starch combination (Pearlitol flash) that are conducive to the manufacturing processes were evaluated. The formulation compositions evaluated are listed in the following table. Batch PD01-403A with Pearlitol flash was manufactured using a direct compression process, whereas, batch PD01-596 containing mannitol 50C, MCC PH101, and pregelatinized starch was manufactured by a HSWG process. Despite the differences in manufacturing processes, diluents and even lubricants, both formulations exhibited good stability.

TABLE 20

Prototype Free Base Compositions manufactured by direct blending and HSWG process - Evaluate Alternate Diluents

| Ingredient | PD01-403-A % w/w | PD01-596 % w/w |
|---|---|---|
| | Batch Number | |
| Compound 1 | 0.133 | 0.14 |
| Mannitol (Pearlitol 50C) | | 56.86 |
| Mannitol (Pearlitol Flash)* | 95.867 | |
| Microcrystalline cellulose (Avicel PH 101) | | 20.00 |
| Partially pregelatinized starch (Starch-1500) | | 20.00 |
| Stearic acid (Hystrene 5016 Veg) | 4.000 | |
| Sodium stearyl fumarate (PRUV) | | 3.00 |
| Total | 100.00 | 100.00 |

*Pearlitol Flash is a co-processed mixture of mannitol and pregelatinized starch (~80%-20% w/w).

In vitro dissolution of the MCC containing batch PD01-596 was evaluated. In pH 2.0 medium, the drug release was incomplete, only ~85% to 90% release at 60-minute for the initial capsule sample and after storage for three months at 40° C./75% RH. The incomplete drug release from the MCC containing formulation may potentially impact the bio-performance.

7.14 Evaluate SSG as a Disintegrant

To mitigate the incomplete dissolution of the MCC containing formulation, effect of SSG as a disintegrant on dissolution of capsules was evaluated as it was compatible with compound 1 free base. Compositions of the four formulations evaluated in this study are shown in the following table. Batches PD01-597, 597A, 660, and 660A were manufactured with no SSG, extra-granular SSG only, both intra- and extra-granular SSG, and intragranular SSG only, respectively. The drug loading was 2.72% to obtain 2 mg strength capsules for the dissolution study. All the batches were manufactured by HSWG process.

TABLE 21

Prototype Free Base Formulations manufactured by HSWG Process - Evaluate Impacts of Disintegrant

| Ingredient | PD01-597 % w/w | PD01-597-A % w/w | PD01-660 % w/w | PD01-660-A % w/w |
|---|---|---|---|---|
| | Batch Number | | | |
| Intra-granular Excipients | | | | |
| Compound 1 | 2.72 | 2.72 | 2.77 | 2.77 |
| Mannitol (Pearlitol 50C) | 54.28 | 44.28 | 51.23 | 53.23 |
| Partially Pregelatinized starch (Starch 1500) | 20.00 | 20.00 | 20.00 | 20.00 |
| Microcrystalline Cellulose (Avicel MCC, PH-101) | 20.00 | 20.00 | 20.00 | 20.00 |
| Sodium starch glycolate (Explotab ®) | | | 3.00 | 3.00 |
| Extra-granular Excipients | | | | |
| Sodium starch glycolate (Explotab ®) | | 10.00 | 2.00 | |
| Sodium Stearyl Fumarate (PRUV) | 3.00 | 3.00 | 1.00 | 1.00 |
| Total | 100.00 | 100.00 | 100.00 | 100.00 |

The dissolution profiles in pH 2 medium of all four batches are shown in FIG. 9. Dissolution of the batch without SSG (PD0-597) was incomplete, the overall release was only ~80% at 60 minutes time point. Incorporation of extra-granular SSG only did not improve the dissolution profile (PD01-597A). In contrast, the addition of intragranular only SSG (PD01-660A) and both intra- and extra-granular SSG (PD01-660) significantly improved the release rate; the overall release was ~93% at 60 minutes. The results suggested that if an MCC containing formulation were to develop, SSG could be added, at least intra-granularly, to improve the dissolution profile.

7.15 Manufacturing Process Development

To identify a suitable manufacturing process that was not only scalable, but must also retain all the critical quality attributes of the drug product, different manufacturing platforms, viz., Direct Blending, Roller Compaction and High Shear Wet Granulation were evaluated. As shown in FIG. 10A, chemical and chiral stability of the free base formulation using same composition (see table below) for each process were found to be significantly better for HSWG/FBD and DB processes when compared to RC process. Manufacturability (high assay recovery and tight CU control) could be achieved using HSWG/FBD process when compared to either DB or RC process. As shown in FIG. 10B, in vitro dissolution of the higher drug loading formulation (see table below) was superior and complete when manufactured using the HSWG/FBD process. The overall rank order of the manufacturing platforms was HSWG/FBD>DB>RC.

TABLE 22

Free base Formulation Compositions for DB/RC/HSWG process evaluation

| HSWG batch # | PD01-511 | PD01-599 |
|---|---|---|
| RC Batch # | PD01-521A/B | PD01-522 A/B |
| DB Batch # | PD01-521 C | PD01-522 C |
| Ingredients | Amount (% w/w) | Amount (% w/w) |
| Compound 1 | 0.13 | 2.7 |
| Mannitol | 76.87 | 74.3 |
| Starch | 20 | 20 |
| SSF | 3 | 3 |
| Total | 100 | 100 |

A = low force,
B = high force

7.16 Excipient Range Finding Study

As discussed above, high shear wet granulation (HSWG) in combination with fluid bed drying (FBD) was identified as the viable manufacturing process for Compound 1 capsules. The drug loading range in the formulation was approximately 0.13% to 2.7% w/w to achieve the anticipated dose range of 0.1 mg to 10 mg capsules strength in capsule size not larger than size 0.

In order to optimize the formulation for the HSWG/FBD process, prototype formulations comprising of MNT/starch/SSF and MNT/starch/MCC/SSF formulations were further evaluated at 3 kg batch size. Factors such as, the type of granulation fluid (water or 15% starch slurry), granulation fluid level, spray rate, and wet massing time, etc. were also evaluated. SSF (lubricant) level was kept constant at 1% for all the evaluated formulations during final blending. The obtained granules were of good quality and possessed good flow which in turn resulted in capsules with tight weight variability. No sticking on-to the face of tamping pins was observed during encapsulation. Both formulations (MNT/starch & MNT/starch/MCC) resulted in good CU; however, the mean label claim values were about 5-8% higher for the manufactured batches. Dissolution at T=0 was faster for MNT/starch formulation than for the MCC containing formulations. Open dish stability study showed good chemical and chiral stability for both the evaluated formulations. Spraying either water or starch slurry also had no impact on the obtained granules. From the preliminary results, MCC was found to be not critical for either granulation growth or to control end point of granulation. In addition, it negatively impacted the in-vitro dissolution performance. Based on the above findings, MNT/starch/SSF based formulation was selected as the lead prototype formulation for the HSWG/FBD process.

To identify the quantitative composition of the MNT/starch/SSF based formulation by HSWG process, the impacts of the levels of the excipients on the product quality attributes were evaluated. The detailed excipient range study compositions are listed in the following table. Batches were manufactured using HSWG/FBD process at 3 kg scale where water was sprayed as the granulation fluid.

TABLE 23

Formulation Composition for Excipient Range Study for the HSWG process

| | Batch Number | | | | | |
|---|---|---|---|---|---|---|
| Ingredient | PD01-692 % w/w | PD01-693 % w/w | PD01-696 % w/w | PD01-697 % w/w | PD01-701 % w/w | PD01-702 % w/w |
| Intra-granular Excipients | | | | | | |
| Compound 1 | 0.133 | 0.133 | 0.667 | 0.667 | 2.667 | 2.667 |
| Mannitol (Pearlitol 50C) | 88.867 | 68.867 | 78.333 | 78.333 | 66.333 | 86.333 |
| Partially Pregelatinized starch (Starch 1500) | 10.00 | 30.00 | 20.00 | 20.00 | 30.00 | 10.00 |
| Purified Water* | 18.65 | 30.67 | 27.84 | 26.50 | 32.46 | 15.22 |

TABLE 23-continued

Formulation Composition for Excipient Range Study for the HSWG process

| Ingredient | PD01-692 % w/w | PD01-693 % w/w | PD01-696 % w/w | PD01-697 % w/w | PD01-701 % w/w | PD01-702 % w/w |
|---|---|---|---|---|---|---|
| | Batch Number | | | | | |
| Extra-granular Excipients | | | | | | |
| Sodium Stearyl Fumarate (PRUV) | 1.00 | 1.00 | 1.00 | 1.00 | 1.00 | 1.00 |
| Total | 100.00 | 100.00 | 100.00 | 100.00 | 100.00 | 100.00 |

*Purified water was removed upon drying

The obtained granules were found to be of good quality with flow properties ranging between easy flowing and free flowing. The physical characterization summary of the final blends is listed in the following table.

TABLE 24

Summary of Physical Characterization of the Excipient Range DoE Formulations using the Final Blends

| Batch Number | Average Particle Size (μm) | D10 | D50 | D90 | BD (g/mL) | TD (g/mL) |
|---|---|---|---|---|---|---|
| PD01-692 | 144.6 | ~NMT 75 μm | ~165 μm | ~NMT 375 μm | 0.63 | 0.83 |
| PD01-693 | 175.8 | ~NMT 87 μm | ~212 μm | ~NMT 430 μm | 0.65 | 0.87 |
| PD01-697 | 173.7 | ~NMT 60 μm | ~230 μm | ~NMT 430 μm | 0.62 | 0.86 |
| PD01-696 | 193.9 | ~NMT 90 μm | ~245 μm | ~NMT 490 μm | 0.63 | 0.88 |
| PD01-701 | 197.4 | ~NMT 88 μm | ~200 μm | ~NMT 560 μm | 0.64 | 0.87 |
| PD01-702 | 125.6 | ~NMT 70 μm | ~135 μm | ~NMT 350 μm | 0.63 | 0.83 |

The encapsulation of all the batches resulted in capsules with tight control over capsule weights. As listed in the following table, the CU mean of all the investigated batches was slightly higher (101.6-104.3%), although the CU RSDs were tight and all the AV values were within the acceptable range.

TABLE 25

Content Uniformity Summary of Formulation Range DoE Batches

| | Dose (mg) | | | | | |
|---|---|---|---|---|---|---|
| | 0.1 | | 0.5 | | 2 | |
| | Batch # | | | | | |
| | PD01-692 | PD01-693 | PD01-697 | PD01-696 | PD01-701 | PD01-702 |
| MEAN | 101.6 | 103.1 | 104.3 | 104.2 | 103.0 | 101.8 |
| % RSD | 2.6 | 1.7 | 1.1 | 1.2 | 1.9 | 2.0 |
| STD DEV. | 2.6 | 1.7 | 1.2 | 1.2 | 1.9 | 2.1 |
| AV | 6.3 | 5.8 | 5.7 | 5.7 | 6.1 | 5.2 |

Dissolution release at pH 2.0 (T=0) of all the manufactured batches also demonstrated fast and complete release profiles as shown in FIG. 11. The open dish chemical (FIG. 12A) and chiral (FIG. 12B) stability at 70° C./0% RH and 60° C./75% RH demonstrated stable drug product upon storage for 3 days and 7 days, respectively. Moreover, stability of the drug product followed a linear relationship with the drug loading where the higher DL formulations demonstrated better chemical and chiral stability. However, the 0.13% DL batches with 30% w/w starch demonstrated relatively higher level of RRT 0.41 impurity profile.

From the excipient range DoE study, it can be inferred that none of the evaluated parameters demonstrated any significant impact on the product attributes (CU, Dissolution, and RI/Chiral stability); however, the batches with 10% starch offered narrow granulation end point window when compared to batches with either 20% w/w or 30% w/w starch. Based on these observations, the formulation with 20% starch was selected for further development.

7.17 Free Base Formulation Compositions

Based on the prototype formulation screening and formulation range finding studies, a composition comprising of mannitol-starch-SSF was selected for further study with a DL of 0.13%, 0.26%, 0.5% and 1.33% that could yield different dose strengths, e.g., as listed in the following table.

TABLE 26

| Unit Formula of Compound 1 at 0.13%, 0.27%, 0.5% and 1.33% Drug Loading | | | | | | | | |
|---|---|---|---|---|---|---|---|---|
| Intragranular Ingredients | % w/w | | % w/w | | % w/w | | % w/w | |
| Compound 1 | 0.13 | | 0.27 | | 0.5 | | 1.33 | |
| Mannitol 50C | 78.87 | | 78.73 | | 78.50 | | 77.67 | |
| Partially pregelatinized starch (Starch 1500) | 20.00 | | 20.00 | | 20.00 | | 20.00 | |
| Purified Water | Q.S | | Q.S | | Q.S | | Q.S | |
| Extragranular Ingredients | % w/w | | % w/w | | % w/w | | % w/w | |
| Sodium stearyl fumarate (Pruv) | 1.00 | | 1.00 | | 1.00 | | 1.00 | |
| Total (% w/w) | 100.00 | | 100.00 | | 100.00 | | 100.00 | |
| Total Capsule Fill weight (mg) | 75 | 300 | 75 | 300 | 80 | 300 | 75 | 300 |
| Dose Strength (mg) | 0.1 | 0.4 | 0.2 | 0.8 | 0.4 | 1.5 | 1.0 | 4.0 |
| HPMC Vcaps Plus Capsule Shell | 4 | 1 | 4 | 1 | 4 | 1 | 4 | 1 |

*Purified Water was removed upon drying

7.18 Multi-Media Dissolution Study

The goal of the study was to develop an in vitro predictive tool that may predict in vivo performance with changes in formulation components (for convenience of reference, referred hereafter as HSWG free base formulation) and its manufacturing process when compared to the free base formulation manufactured using the direct blending (DB) process. In-vitro multi-media dissolution studies were conducted at pH 2.0, 4.5, and 6.8.

To assess the impact of multi-media dissolution medias, the dose strength of 2 mg was assessed. The results from this study are demonstrated in FIG. 13. At pH 2.0, both the DB and HSWG free base formulations were found to be comparable, whereas, when the pH was shifted to 4.5 and 6.8, dissolution profiles of the HSWG free base formulation were found to be slower when compared to the DB formulation.

A two-stage dissolution test was also performed to assess precipitation risk upon the transition of the physiological pH from 1.2 (0 to 30 minutes) in the stomach to 6.8 (30 to 90 minutes) in the intestine. Capsules of both the DB and HSWG free base formulations, at 0.5 mg dose, were evaluated. Based on the results from the two-stage dissolution test as shown in FIG. 14, it can be inferred that the risk of precipitation was anticipated to be low.

7.19 Prototype Free Base Formulation with Fumaric Acid

As discussed above, the proposed HSWG free base formulation was found to be slower in bio-relevant dissolution media. An alternate formulation with 1% and 3% fumaric acid was manufactured at 2 mg dose strength. The compositions are listed in the following table. The rationale for addition of fumaric acid in the formulation was to maintain the micro-environment pH in acidic range as the drug substance is soluble at lower pH due to its pH dependent solubility nature. The in vitro dissolution performance was assessed at pH 4.5, as it was found to incorporate maximum discriminatory power over other dissolution medias.

TABLE 27

| Composition of the HSWG Free Base Formulation with FA for Monkey PK Studies at 2 mg Dose Strength | | | | |
|---|---|---|---|---|
| | Product Description | | | |
| | 2 mg DB free base formulation (with 3% FA) | 2 mg HSWG free base formulation with 1% FA | 2 mg HSWG free base formulation with 3% FA | 2 mg HSWG Free base formulation (without FA) |
| | Product Batch No | | | |
| | 1354-8-2-4 | PD01-874 | PD01-873 | PD01-870 |
| | API PSD $D_{50/90}$ (SSA) | | | |
| | 15/31 um (0.94 $m^2/g$) | | 22/49 um (1.04 $m^2/g$) | |
| Ingredients | mg/Capsule (or wt %) | mg/Capsule (or wt %) | mg/Capsule (or wt %) | mg/Capsule (or wt %) |
| Compound 1 API* | 1.00 | 1.333 | 1.333 | 1.333 |
| Mannitol (Pearlitol 50C)** | 0.00 | 76.667 | 74.667 | 77.667 |
| Mannitol (Pearlitol SD 200)** | 90.00 | 0.00 | 0.00 | 0.00 |
| Starch 1500 (Partially pregelatinized Maize Starch) | 0.00 | 20.00 | 20.00 | 20.00 |
| Fumaric acid (Penta-powder) | 3.00 | 1.00 | 3.00 | 0.00 |
| Colloidal silicon dioxide (Aerosil 200) | 2.00 | 0.00 | 0.00 | 0.00 |
| Stearic acid (Hystrene 5016 Veg) | 4.00 | 0.00 | 0.00 | 0.00 |
| Sodium stearyl fumarate (PRUV) | 0.00 | 1.00 | 1.00 | 1.00 |
| Total | 100.00 | 100.00 | 100.00 | 100.00 |

*Based on theoretical potency of DS; Amount was corrected for as-is potency.

**Amount varied to compensate for difference in API amount based on actual potency.

The dissolution release performance of the HSWG FB formulations with, 100 and 300 FA was found to be significantly faster and higher when compared to either DB FB formulation with FA or the HSWG FB formulation without FA as shown in FIG. 15. This study corroborated the hypothesis that incorporation of fumaric acid was aiding in higher drug dissolution by maintaining favorable micro-environmental pH conducive for higher drug solubility.

7.21 Evaluate Hydrobromic Acid Salt Option as an Alternate HSWG Formulation

To assess the impact of the HBr salt of the Compound 1 on in vitro performance, an alternate HSWG formulation of the HBr salt without fumaric acid was manufactured. The composition of the HSWG HBr formulation at 0.5 mg dose strength is listed in the following table.

TABLE 28

Composition of the 0.5 mg Capsules for monkey PK Study-2: DB FB formulation, HSWG FB formulation, and HSWG FB formulation with 3% FA, and HSWG HBr formulation

| | Product Description | | | |
|---|---|---|---|---|
| | DB FB formulation (0.5 mg) | HSWG FB formulation with 3% FA (0.5 mg) | HSWG HBr formulation (0.5 mg) | HSWG FB formulation (0.5 mg) |
| | Product Batch No | | | |
| | 19B0011 | PD02-016 | PD02-029 | PD01-869 |
| | API PSD $D_{50/90}$ (SSA) | | | |
| Ingredients | 19/64 um (0.84 $m^2/g$) mg/Capsule (or wt %) | 22/49 um (1.04 $m^2/g$) mg/Capsule (or wt %) | Data Unavailable mg/Capsule (or wt %) | 22/49 um (1.04 $m^2/g$) mg/Capsule (or wt %) |
| Compound 1 API* | 0.5 | 0.5 | 0.57 | 0.5 |
| Mannitol (Pearlitol 50C)** | 0 | 75.5 | 78.43 | 78.5 |
| Mannitol (Pearlitol SD 200)** | 91.5 | 0 | 0 | 0 |
| Starch 1500 (Partially pregelatinized Maize Starch) | 0 | 20 | 20 | 20 |
| Fumaric acid (Penta-powder) | 3 | 3 | 0 | 0 |
| Colloidal silicon dioxide (Aerosil 200) | 1 | 0 | 0 | 0 |
| Stearic acid (Hystrene 5016 Veg) | 4 | 0 | 0 | 0 |
| Sodium stearyl fumarate (PRUV) | 0 | 1 | 1 | 1 |
| Total | 100 | 100 | 100 | 100 |

*Based on theoretical potency of DS; Amount was corrected for as-is potency.

**Amount varied to compensate for difference in API amount based on actual potency.

7.20 Animal PK Study-I

An animal PK study in male monkeys was carried out to find out if there is any correlation between the pH 4.5 dissolution and the PK profiles in monkey. Each co-hort was dosed with 2 mg capsules of the following formulations: DB FB formulation (300 FA), HSWG FB formulation without FA, HSWG FB formulation with 1% FA, and HSWG FB formulation with 3% FA.

A cross-over study design comprising 4 male monkeys per cohort (at-least 1-week washout period) received the different formulations. Moreover, the monkeys were fasted overnight and 4 hours post-administration. PK samples were collected up-to 24-hours post dosing. The HSWG FB formulation without FA demonstrated the lowest exposure (AUC) and higher variability followed by the DB FB formulation with 3% FA, whereas, the HSWG FB formulations with 1% and 3% FA demonstrated similar and significantly higher exposures as shown in FIG. 16.

Likewise, the in vitro dissolution rank order was found to be similar to in vivo AUC rank order qualitatively indicating a good in vitro-in vivo correlation. Based on the in vitro dissolution at pH 4.5 and in vivo Monkey AUC data, the formulations were rank ordered as following: HSWG FB formulation with 3% FA≥HSWG FB formulation with 1% FA>>>DB FB formulation (3% FA)>HSWG FB formulation (without FA).

The HSWG HBr composition was not optimized, instead, to make a head-on comparison of the drug substance form (free base vs. HBr salt), the composition and the manufacturing process were left unaltered.

The dissolution performance of the HSWG HBr formulation at 0.5 mg dose strength was assessed against the DB FB and HSWG FB formulation, and HSWG FB formulation with 3% FA at pH 4.5 as shown in FIG. 17.

The HSWG HBr formulation demonstrates faster and almost complete dissolution when compared to either DB FB, or HSWG FB or HSWG FB with 3% FA formulations in pH 4.5 media.

7.22 Animal PK Study-II

Another monkey PK study was designed for 0.5 mg dose strength comprising the following four co-horts (four monkeys per co-hort): DB FB, HSWG FB, HSWG FB with 3% FA, and HSWG HBr formulations. The compositions of all the formulations are specified in the section above.

From this study, the HSWG HBr formulation and HSWG FB formulation with 3% FA demonstrated much higher absorption than the DB FB and HSWG FB formulations; wherein the HSWG HBr formulation demonstrated the highest AUC among all the formulations. It was observed that both the DB FB and HSWG FB formulations demonstrated comparable bio-performance as shown in FIG. 18. The formulation rank order based on the AUC is as following: HSWG HBr formulation>HSWG FB formulation with 3% FA>>>DB FB formulation with 3% FA=HSWG FB formulation.

TABLE 29

| Monkey (male) PK Data Summary following Oral Administration 0.5 mg Dose Strengths | | | | |
|---|---|---|---|---|
| Formulation | $T_{max}$ (hr) | $C_{max}$ (ng/mL) | $AUC_t$ (ng*hr/mL) | HSWG/DB Ratio |
| DB FB formulation (3% FA) | 2.8 (1-4) | 1.5 (44) | 6.0 (39) | — |
| HSWG FB formulation (w/o FA) | 2.5 (2-4) | 1.4 (62) | 7.3 (38) | $C_{max}$ 7% lower & $AUC_t$ 20% higher than DB FB |
| HSWG FB formulation with 3% FA | 1.8 (1-2) | 7.1 (41) | 27.5 (42) | $C_{max}$ & $AUC_t$ ~4.5 folds higher than DB FB |
| HSWG HBr formulation | 2.0 (2) | 8.7 (43) | 33.1 (37) | $C_{max}$ & $AUC_t$ ~5.5 folds higher than DB FB |

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A pharmaceutical composition comprising 1) a hydrobromide salt of Compound 1:

1

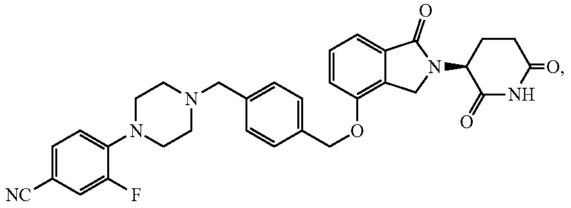

2) A mixture of mannitol and cellulose or a mixture of mannitol and starch, 3) hydroxypropyl methylcellulose (HPMC), 4) sodium starch glycolate (SSG), and 5) stearic acid.

2. The pharmaceutical composition of claim 1, comprising: 1) a hydrobromide salt of Compound 1 at an amount of from about 0.05 to about 3% w/w; 2) a carrier or diluent at an amount of from about 70 to about 98% w/w; 3) HPMC at an amount of from about 0.5 to about 10% w/w; 4) SSG at an amount of from about 0.5 to about 10% w/w; and 5) stearic acid at an amount of from about 0.5 to about 8% w/w; and wherein the carrier or diluent is a mixture of mannitol and cellulose or a mixture of mannitol and starch.

3. The pharmaceutical composition of claim 2, wherein the hydrobromide salt of Compound 1 is a crystalline hydrobromide salt of Compound 1.

4. The pharmaceutical composition of claim 2, wherein the hydrobromide salt of Compound 1 is characterized by an XRPD pattern comprising peaks at approximately 10.3, 19.3, and 24.0° 2θ.

5. The pharmaceutical composition of claim 2, wherein the amount of the hydrobromide salt of Compound 1 is from about 0.16 to about 0.65% w/w.

6. The pharmaceutical composition of claim 2, wherein the component 2) is a mixture of mannitol and cellulose.

7. The pharmaceutical composition of claim 6, wherein the cellulose is microcrystalline cellulose (MCC).

8. The pharmaceutical composition of claim 2, wherein the component 2) is a mixture of mannitol and starch.

9. The pharmaceutical composition of claim 8, wherein the starch is partially pregelatinized starch.

10. The pharmaceutical composition of claim 2, wherein the amount of the mixture of mannitol and cellulose or the mixture of mannitol and starch is from about 85 to about 86% w/w.

11. The pharmaceutical composition of claim 2, wherein the amount of the mannitol is from about 50 to about 80% w/w, and the amount of the cellulose or starch is from about 10 to about 30% w/w.

12. The pharmaceutical composition of claim 11, wherein the amount of the mannitol is from about 65 to about 66% w/w, and the amount of the cellulose or starch is about 20% w/w.

13. The pharmaceutical composition of claim 2, wherein the weight ratio of the cellulose or starch to the mannitol is from about 1:1.7 to about 1:8.

14. The pharmaceutical composition of claim 13, wherein the weight ratio of the cellulose or starch to the mannitol is about 1:3.3.

15. The pharmaceutical composition of claim 2, wherein the HPMC is HPMC E5.

16. The pharmaceutical composition of claim 2, wherein the amount of the HPMC is about 5% w/w.

17. The pharmaceutical composition of claim 2, wherein the SSG is low pH SSG.

18. The pharmaceutical composition of claim 2, wherein the amount of the SSG is about 5% w/w.

19. The pharmaceutical composition of claim 2, wherein the amount of stearic acid is about 4% w/w.

20. The pharmaceutical composition of claim 1, comprising: 1) a hydrobromide salt of Compound 1 at an amount of about 0.16% w/w; 2) mannitol at an amount of about 65.84% w/w and microcrystalline cellulose an amount of about 20% w/w; 3) HPMC E5 at an amount of about 5% w/w; 4) low pH SSG at an amount of about 5% w/w; and 5) stearic acid at an amount of about 4% w/w.

21. The pharmaceutical composition of claim 1, comprising: 1) a hydrobromide salt of Compound 1 at an amount of about 0.65% w/w; 2) mannitol at an amount of about 65.35% w/w and microcrystalline cellulose an amount of about 20% w/w; 3) HPMC E5 at an amount of about 5% w/w; 4) low pH SSG at an amount of about 5% w/w; and 5) stearic acid at an amount of about 4% w/w.

22. A method of treating multiple myeloma comprising administering a therapeutically effective amount of the pharmaceutical composition of claim 2 to a patient having multiple myeloma.

* * * * *